(12) United States Patent
Schuerch, Jr.

(10) Patent No.: US 10,842,700 B2
(45) Date of Patent: Nov. 24, 2020

(54) ADJUSTABLE POSITION LIMB SUPPORT FOR SURGICAL TABLES, INCLUDING QUICK-CONNECT UNIVERSAL BOOT MOUNT

(71) Applicant: Peter E. Schuerch, Jr., Quincy, MA (US)

(72) Inventor: Peter E. Schuerch, Jr., Quincy, MA (US)

( * ) Notice: Subject to any disclaimer, the term of this patent is extended or adjusted under 35 U.S.C. 154(b) by 717 days.

(21) Appl. No.: 15/477,393

(22) Filed: Apr. 3, 2017

(65) Prior Publication Data

US 2017/0296417 A1 Oct. 19, 2017

Related U.S. Application Data

(63) Continuation-in-part of application No. 15/442,074, filed on Feb. 24, 2017, which is a continuation-in-part
(Continued)

(51) Int. Cl.
*A61G 13/12* (2006.01)
*A61F 5/37* (2006.01)
*A61G 13/10* (2006.01)

(52) U.S. Cl.
CPC .......... *A61G 13/129* (2013.01); *A61F 5/3761* (2013.01); *A61G 13/101* (2013.01); *A61G 13/125* (2013.01); *A61G 13/1245* (2013.01)

(58) Field of Classification Search
CPC .............. A61G 13/1245; A61G 13/125; A61G 13/1205; A61G 13/101; A61G 13/0036; A61G 13/0063; A61G 13/128
(Continued)

(56) References Cited

U.S. PATENT DOCUMENTS 333,220 A 12/1885 Hildebrand
357,694 A 2/1887 Kiein
(Continued)

FOREIGN PATENT DOCUMENTS

CN 201870867 6/2011
GB 743130 1/1956

OTHER PUBLICATIONS

Trimano Support Arm, 2011, Arthrex GmbH.
(Continued)

*Primary Examiner* — Kari K Rodriquez
(74) *Attorney, Agent, or Firm* — Pandiscio & Pandisciso

(57) ABSTRACT

A surgical boot mount for mounting a surgical boot to a support rod of a limb holder, the surgical boot mount comprising: a projection having a first section and a second section, wherein the first section is attached to the sole of the surgical boot, wherein the first section comprises a first diameter and the second section comprises a second diameter, and further wherein the second diameter is larger than the first diameter; and a releasable locking mechanism mounted to the support rod of the limb holder, wherein the releasable locking mechanism comprises a first key comprising a first keyway and a second key comprising a second keyway, wherein the second key is slidably connected to the first key, wherein the first key is biased away from the second key, wherein the first keyway and the second keyway overlap to form an opening at least as large as the second diameter when an inwardly-directed force is applied to the first key so as to overcome the bias, and further wherein the opening is reduced to a size smaller than the second diameter when the inwardly-directed force is released from the first key.

16 Claims, 53 Drawing Sheets

Related U.S. Application Data of application No. 14/056,857, filed on Oct. 17, 2013, now Pat. No. 9,801,771.

(60) Provisional application No. 61/715,028, filed on Oct. 17, 2012, provisional application No. 62/299,277, filed on Feb. 24, 2016, provisional application No. 62/316,851, filed on Apr. 1, 2016.

(58) Field of Classification Search
USPC .......... 248/230.3, 229.12, 286.1, 218.4, 214
See application file for complete search history.

(56) References Cited

U.S. PATENT DOCUMENTS

| | | |
|---|---|---|
| 358,513 A | 3/1887 | Walton |
| 541,863 A | 7/1895 | Loomis |
| 548,024 A | 10/1895 | Adams |
| 574,877 A | 1/1897 | Blomiley |
| 979,091 A | 12/1910 | Pickart |
| 988,923 A | 4/1911 | Bauerfeind |
| 1,134,720 A | 4/1915 | Bradley |
| 1,279,120 A | 9/1918 | Kellogg |
| 1,446,811 A | 2/1923 | Rowland |
| 1,697,121 A | 1/1929 | Knebel |
| 1,776,167 A | 9/1930 | Stenshoel |
| 1,858,144 A | 5/1932 | Fariello |
| 1,894,739 A | 1/1933 | Gilbert |
| 1,919,908 A | 7/1933 | Schmidt et al. |
| 2,250,026 A | 7/1941 | Laukhuff |
| 2,442,916 A | 6/1948 | Buchanan |
| 2,528,048 A | 10/1950 | Gilleland |
| 2,642,250 A | 6/1953 | Kasnowich |
| 2,651,725 A | 9/1953 | Margaret |
| 2,711,872 A | 6/1955 | Lampke |
| 2,898,068 A | 8/1959 | Warren |
| 2,933,567 A | 4/1960 | Yale |
| 3,046,072 A | 7/1962 | Douglass, Jr. et al. |
| 3,268,922 A | 8/1966 | Moxley |
| 3,277,501 A | 10/1966 | Frisz et al. |
| 3,329,978 A | 7/1967 | Porter et al. |
| 3,452,978 A | 7/1969 | Creelman |
| 3,810,462 A | 5/1974 | Szpur |
| 3,817,512 A | 6/1974 | Torrey |
| 3,829,914 A | 8/1974 | Treat |
| 3,849,813 A | 11/1974 | Neilson |
| 4,012,799 A | 3/1977 | Rutherford |
| 4,034,574 A | 7/1977 | Kugler |
| 4,067,079 A | 1/1978 | Buchman |
| 4,085,818 A | 4/1978 | Swager |
| 4,299,213 A | 11/1981 | Violet |
| D262,237 S | 12/1981 | Stauber |
| 4,308,419 A | 12/1981 | Fredriksson |
| 4,373,709 A | 2/1983 | Whitt |
| 4,426,071 A | 1/1984 | Klevstad |
| 4,457,302 A | 7/1984 | Caspari et al. |
| 4,547,092 A | 10/1985 | Vetter et al. |
| 4,564,179 A | 1/1986 | Hollingsworth |
| 4,564,180 A | 1/1986 | Agee et al. |
| 4,796,846 A | 1/1989 | Meier et al. |
| 4,913,413 A | 4/1990 | Raab |
| 5,010,898 A | 4/1991 | De Kanawati et al. |
| D322,532 S | 12/1991 | Kumar et al. |
| 5,135,210 A | 8/1992 | Michelson |
| 5,275,176 A | 1/1994 | Chandler |
| 5,276,927 A | 1/1994 | Day |
| 5,281,001 A | 1/1994 | Bergsten et al. |
| 5,369,827 A | 12/1994 | Parke et al. |
| D370,061 S | 5/1996 | Shirley |
| 5,538,215 A | 7/1996 | Hosey |
| 5,544,968 A | 8/1996 | Goeliner |
| 5,560,577 A | 10/1996 | Keselman |
| 5,571,072 A | 11/1996 | Kronner |
| 5,582,379 A | 12/1996 | Keselman et al. |
| 5,597,146 A | 1/1997 | Putman |
| 5,775,334 A | 7/1998 | Lamb et al. |
| 5,802,641 A | 9/1998 | Van Steenburg |
| 5,829,077 A | 11/1998 | Neige |
| 5,836,559 A | 11/1998 | Ronci |
| 5,888,197 A | 3/1999 | Mulac et al. |
| 5,918,330 A | 7/1999 | Navarro et al. |
| 5,926,876 A | 7/1999 | Haigh et al. |
| 5,961,085 A | 10/1999 | Navarro et al. |
| 5,961,512 A | 10/1999 | Purnell |
| D419,673 S | 1/2000 | Schattner |
| 6,023,800 A | 2/2000 | Stickley |
| 6,029,669 A | 2/2000 | Hammock |
| 6,058,534 A | 5/2000 | Navarro et al. |
| 6,138,970 A | 10/2000 | Sohrt et al. |
| 6,250,712 B1 | 6/2001 | Livington et al. |
| 6,263,531 B1 | 7/2001 | Navarro et al. |
| 6,276,651 B1 | 8/2001 | Dolan |
| 6,315,260 B1 | 11/2001 | Lees |
| D455,831 S | 4/2002 | Koros et al. |
| 6,499,158 B1 | 12/2002 | Easterling |
| 6,557,195 B2 | 5/2003 | Dinkler |
| 6,564,406 B2 | 5/2003 | VanSteenburg et al. |
| 6,568,008 B2 | 5/2003 | Siepmann et al. |
| 6,622,980 B2 | 9/2003 | Boucher et al. |
| 6,663,055 B2 | 12/2003 | Boucher et al. |
| 6,704,959 B2 | 3/2004 | Schuerch |
| 7,003,827 B2 | 2/2006 | DeMayo |
| 7,020,917 B1 | 4/2006 | Kolody et al. |
| 7,159,832 B2 | 1/2007 | Easterling |
| 7,171,709 B2 | 2/2007 | Weismiller |
| 7,243,654 B2 | 7/2007 | Schuerch |
| D551,763 S | 9/2007 | Phillips et al. |
| 7,337,483 B2 * | 3/2008 | Boucher ............... A61G 13/12 5/621 |
| 7,422,016 B2 | 9/2008 | Klemm |
| D584,816 S | 1/2009 | Koros et al. |
| D606,832 S | 12/2009 | Wan et al. |
| RE41,412 E | 7/2010 | Van Steenburg |
| 7,857,271 B2 | 12/2010 | Lees |
| D633,208 S | 2/2011 | Mürner |
| 9,333,142 B2 | 5/2016 | Schuerch, Jr. |
| 9,782,316 B2 | 10/2017 | Schuerch, Jr. et al. |
| 9,801,771 B2 | 10/2017 | Schuerch, Jr. |
| 2001/0039680 A1 | 11/2001 | Boucher et al. |
| 2002/0128577 A1 * | 9/2002 | Smart .................. A61F 5/04 602/36 |
| 2003/0199738 A1 | 10/2003 | Yager |
| 2003/0229273 A1 | 12/2003 | Mulac et al. |
| 2004/0143243 A1 | 7/2004 | Wahrburg |
| 2006/0039750 A1 | 2/2006 | Thomke et al. |
| 2006/0225743 A1 | 10/2006 | Schuerch |
| 2008/0121765 A1 | 5/2008 | Fetzer |
| 2008/0215065 A1 | 9/2008 | Wang et al. |
| 2009/0236484 A1 | 9/2009 | Koch et al. |
| 2010/0030377 A1 | 2/2010 | Unsworth |
| 2012/0010629 A1 | 1/2012 | Mire et al. |
| 2012/0174318 A1 | 7/2012 | Vestergaard |
| 2012/0197182 A1 | 8/2012 | Millman et al. |
| 2012/0209291 A1 | 8/2012 | Anderson et al. |
| 2012/0253513 A1 | 10/2012 | Unsworth |
| 2017/0165143 A1 | 6/2017 | Schuerrt, Jr. |

OTHER PUBLICATIONS

Arthroscopy Limb Positioners, Limb Positioners for Hip, Knee, Distal Extremities and Shoulder, 2013, Arthrex Inc.

Bansbach, easy lift Configurator for Lockable Gas Springs, http://www.bansbach.de/Blockierfeder/en/index.html.

* cited by examiner

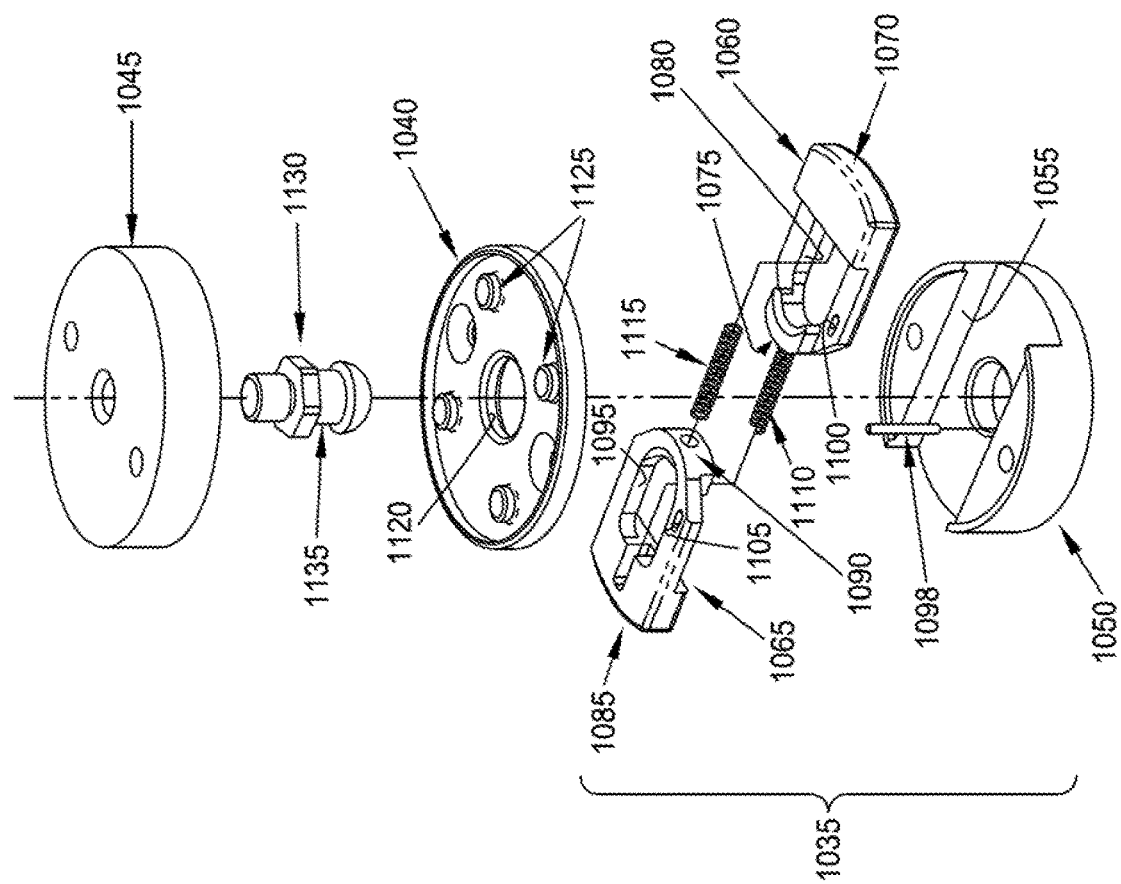

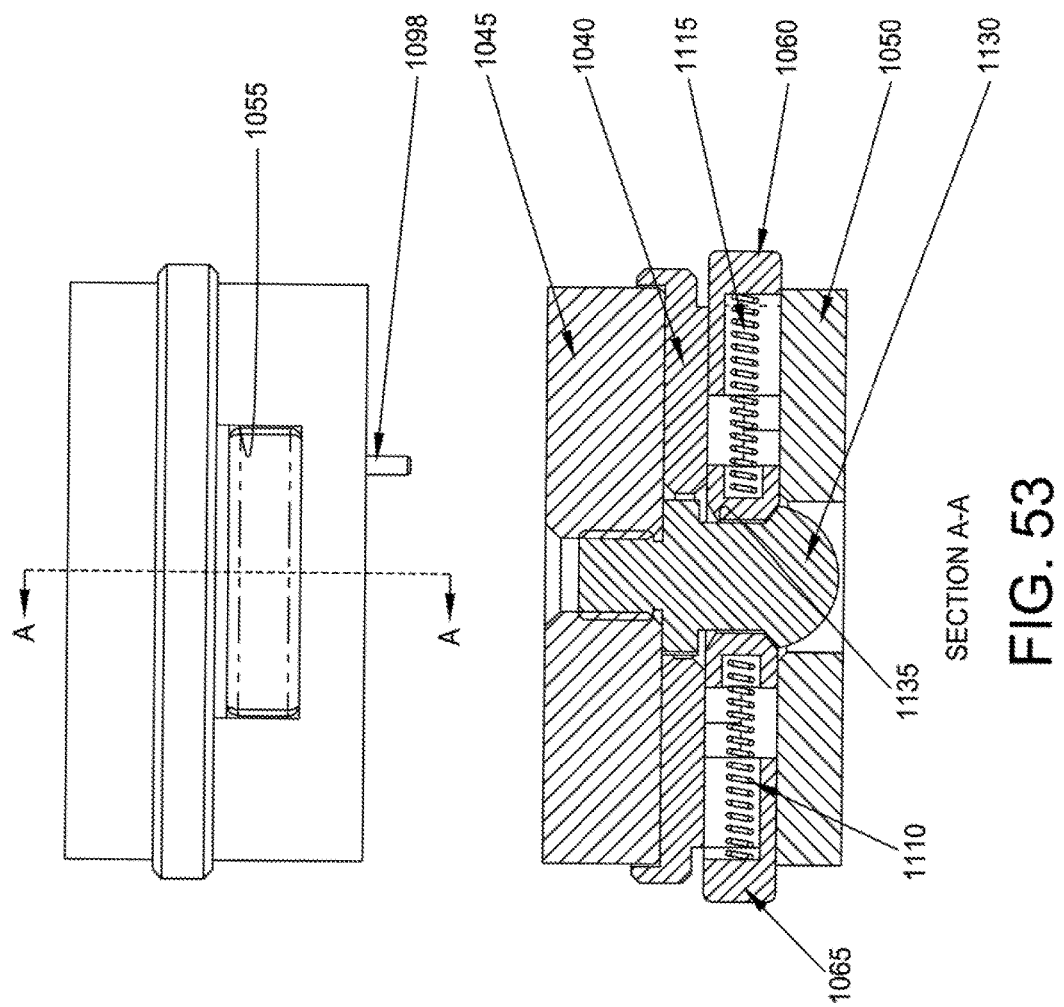

ADJUSTABLE POSITION LIMB SUPPORT FOR SURGICAL TABLES, INCLUDING QUICK-CONNECT UNIVERSAL BOOT MOUNT

REFERENCE TO PENDING PRIOR PATENT APPLICATIONS

This patent application:

(i) is a continuation-in-part of pending prior U.S. patent application Ser. No. 15/442,074, filed Feb. 24, 2017 by Peter E. Schuerch J R. for ADJUSTABLE POSITION LIMB SUPPORT FOR SURGICAL TABLES, which patent application in turn:

(a) is a continuation-in-part of pending prior U.S. patent application Ser. No. 14/056,857, filed Oct. 17, 2013 by Peter E. Schuerch, J R. for ADJUSTABLE POSITION LIMB SUPPORT FOR SURGICAL TABLES, which patent application in turn claims benefit of prior U.S. Provisional Patent Application Ser. No. 61/715,028, filed Oct. 17, 2012 by Peter Schuerch J R. for ADJUSTABLE POSITION LIMB SUPPORT FOR SURGICAL TABLES; and (b) claims benefit of prior U.S. Provisional Patent Application Ser. No. 62/299,277, filed Feb. 24, 2016 by Peter E. Schuerch J R. for ADJUSTABLE POSITION LIMB SUPPORT FOR SURGICAL TABLES; and (ii) claims benefit of prior U.S. Provisional Patent Application Ser. No. 62/316,851, filed Apr. 1, 2016 by Peter E. Schuerch J R. for ADJUSTABLE POSITION LIMB SUPPORT FOR SURGICAL TABLES.

The five (5) above-identified patent applications are hereby incorporated herein by reference.

FIELD OF THE INVENTION

This invention relates to medical devices in general, and more particularly to adjustable position limb supports for attachment to surgical tables for positioning and supporting a patient's limb.

BACKGROUND OF THE INVENTION

Patients undergoing a gynecologic, urologic or laparoscopic procedure must generally be properly positioned in order for the physician to carry out the procedure with maximum benefit. Properly positioning a patient for such a procedure typically requires that the patient lay in the supine position, with their knees raised up to varying degrees. This is known as the lithotomy position.

During the gynecologic, urologic or laparoscopic procedure, it is common for the lower legs of the patient to be supported in the desired position by a pair of leg stirrups.

Leg stirrups of the kind typically used for gynecologic, urologic or laparoscopic procedures are well known in the art. Such leg stirrups typically comprise an adjustable attachment mechanism at the proximal end of the stirrup which is configured to attach the stirrup to a surgical table, a support member extending distally away from the attachment mechanism (generally along the line of the patient's leg), and a padded "boot" section, configured to partially surround a calf and foot of a patient, slidably mounted to the support member so as to provide a comfortable contact or support surface for the patient's calf and heel. This padded boot section also serves to reduce or eliminate pressure on various nerves in the patient's leg, thereby further increasing patient comfort.

As noted above, a patient undergoing a gynecologic, urologic and/or laparoscopic procedure is typically put in the lithotomy position, with knees raised up to varying degrees. During the course of the procedure, it may be expedient or necessary for the physician to alter the position or orientation of the patient's leg(s). Such alteration requires the adjustment of the adjustable attachment mechanism located at the proximal end of the leg stirrup(s) proximate the patient's hip joint(s).

Early versions of such leg stirrups required the physician to adjust the position of a leg stirrup by direct manipulation of the adjustable attachment mechanism, which is located at the proximal end of the leg stirrup and hence quite close to the procedure site (e.g., in and around the patient's pelvic area). However, the adjustment of the leg stirrup at that location can be inconvenient for the physician, since the physician is typically located at the distal end of the leg stirrup. Accordingly, more recent versions of leg stirrups allow for the adjustment of the position of the leg stirrup by providing means at the distal end of the leg stirrup to manipulate the position of the leg stirrup.

These more recent versions of leg stirrups are still deficient, however, inasmuch as they fail to provide a full range of motion or adjustment for the patient's limb. For example, in some recent versions of leg stirrups, the stirrups may be adjusted only in the lithotomy (i.e., up and down) and abduction/adduction (i.e., side-to-side) directions, but do not allow adjustment in the supination/pronation direction. Also, the means to effect position adjustments on existing leg stirrups can be cumbersome to manipulate.

Accordingly, there is a need for an improved leg stirrup assembly wherein the position of the leg stirrup assembly may be easily adjusted at the distal end of the leg stirrup, and wherein the leg stirrup assembly may be moved in three distinct axes of rotation (i.e., lithotomy, abduction/adduction and supination/pronation), in a manner more like the natural motion of the human hip joint.

SUMMARY OF THE INVENTION

This invention comprises the provision and use of a stirrup-type leg holder of novel construction, independently adjustable in the lithotomy, abduction/adduction and supination/pronation dimensions, that is, along three distinct axes of rotation, through the action of a single control mechanism which may be located at the distal end of the leg stirrup.

In one preferred construction, the device comprises a means for attachment to a surgical table, to which is attached an element about which rotation may take place, and a means to control the amount of rotation in the three dimensions described.

A mechanism is provided which keeps the device in a locked position and, upon activation of a release mechanism, the device is free to move in any of the dimensions described, or in all three dimensions simultaneously.

The release mechanism is preferably operated by cable and may therefore be located anywhere on the device as desired, with the end distal to the proximally-located table attachment means being preferred for the location of the release mechanism, whereby to position at least a portion of the release mechanism at the distal end of the leg stirrup.

In one preferred form of the present invention, there is provided a stirrup-type leg holder which comprises a mounting bracket for attachment to a surgical table; a semi-ball for attachment to the mounting bracket; a clamping assembly comprising an upper jaw and a lower jaw for clamping engagement about the semi-ball; and a stirrup boot mounted to the clamping assembly via a support rod. A release mechanism is provided to selectively release the clamping assembly so as to allow the stirrup boot to be repositioned relative to the semi-ball (and hence repositioned relative to the surgical table). The release mechanism comprises an actuating mechanism (e.g., a handle and trigger) which controls a cam mechanism which can force the upper jaw and lower jaw apart, against the power of a spring, whereby to allow the upper jaw and lower jaw to rotate about the semi-ball, and hence allow the position of the stirrup boot to be adjusted relative to the surgical table. In one preferred construction, the semi-ball comprises an upper limiting pin and a lower limiting pin which cooperate with an upper limit surface on the upper jaw and a lower limit surface on the lower jaw to limit rotation of the upper and lower jaws about the semi-ball. A gas cylinder is also provided to assist in positioning the stirrup boot relative to the surgical table.

In another preferred form of the present invention, there is provided a limb holder comprising:
  a mounting bracket for attachment to a surgical table;
  a mounting element comprising a spheroidal surface for attachment to said mounting bracket;
  a clamping assembly for providing a clamping engagement about said spheroidal surface of said mounting element, said clamping assembly comprising an upper jaw and a lower jaw, wherein said upper jaw and said lower jaw are biased towards one another so as to provide said clamping engagement about said sphereoidal surface of said mounting element;
  a limb support element mounted to said clamping assembly via a support rod; and
  a release mechanism mounted to said support rod and connected to said clamping assembly for selectively releasing said clamping engagement of said clamping assembly about said sphereoidal surface of said mounting element, whereby to allow said limb support element to be repositioned relative to said mounting element and hence repositioned relative to the surgical table.

In another preferred form of the present invention, there is provided a method for supporting a limb adjacent to a surgical table, the method comprising:
  providing a limb holder comprising:
    a mounting bracket for attachment to a surgical table;
    a mounting element comprising a spheroidal surface for attachment to said mounting bracket;
    a clamping assembly for providing a clamping engagement about said spheroidal surface of said mounting element, said clamping assembly comprising an upper jaw and a lower jaw, wherein said upper jaw and said lower jaw are biased towards one another so as to provide said clamping engagement about said sphereoidal surface of said mounting element;
    a limb support element mounted to said clamping assembly via a support rod; and
    a release mechanism mounted to said support rod and connected to said clamping assembly for selectively releasing said clamping engagement of said clamping assembly about said sphereoidal surface of said mounting element, whereby to allow said limb support element to be repositioned relative to said mounting element and hence repositioned relative to the surgical table; and
  utilizing the release mechanism to reposition said limb support element relative to said mounting element and hence relative to the surgical table.

In another preferred form of the invention, a stirrup-type leg holder can be mounted to a surgical table by means of a ball-and-socket arrangement, wherein the "socket" is fixedly mounted to a surgical table and the "ball" is fixedly mounted to the proximal end of a leg support assembly, such that the leg support assembly can be moved along at least three (3) axes of rotation relative to the surgical table.

In one preferred form of the present invention, there is provided a limb holder comprising:
  a mounting element comprising a spheroidal surface;
  a support rod mounted to said mounting element;
  a limb support element for receiving a limb of a patient, said limb support element being configured for mounting to said support rod;
  a mounting bracket for attachment to a surgical table;
  a clamping assembly for providing a clamping engagement about said spheroidal surface of said mounting element, said clamping assembly being configured for attachment to said mounting bracket, and said clamping assembly comprising an upper jaw and a lower jaw, wherein said upper jaw and said lower jaw are biased towards one another so as to provide said clamping engagement about said sphereoidal surface of said mounting element; and
  a release mechanism mounted to said support rod and connected to said clamping assembly for selectively releasing said clamping engagement of said clamping assembly about said sphereoidal surface of said mounting element, whereby to allow said mounting element to be repositioned relative to said clamping assembly and hence allow said limb support element to be repositioned relative to the surgical table.

In another preferred form of the present invention, there is provided a method for supporting a limb adjacent to a surgical table, the method comprising:
  providing a limb holder comprising:
    a mounting element comprising a spheroidal surface;
    a support rod mounted to said mounting element;
    a limb support element for receiving a limb of a patient, said limb support element being configured for mounting to said support rod;
    a mounting bracket for attachment to a surgical table;
    a clamping assembly for providing a clamping engagement about said spheroidal surface of said mounting element, said clamping assembly being configured for attachment to said mounting bracket, and said clamping assembly comprising an upper jaw and a lower jaw, wherein said upper jaw and said lower jaw are biased towards one another so as to provide said clamping engagement about said sphereoidal surface of said mounting element; and
    a release mechanism mounted to said support rod and connected to said clamping assembly for selectively releasing said clamping engagement of said clamping assembly about said sphereoidal surface of said mounting element, whereby to allow said mounting element to be repositioned relative to said clamping assembly and hence allow said limb support element to be repositioned relative to the surgical table; and
  utilizing the release mechanism to reposition said mounting element relative to said clamping assembly and hence reposition said limb support element relative to the surgical table.

In another preferred form of the invention, a quick-connect universal boot mount can be provided for mounting a boot to the remainder of a limb holder.

In one preferred form of the present invention, there is provided a surgical boot mount for mounting a surgical boot to a support rod of a limb holder, the surgical boot mount comprising:

a projection having a first section and a second section, wherein the first section is attached to the sole of the surgical boot, wherein the first section comprises a first diameter and the second section comprises a second diameter, and further wherein the second diameter is larger than the first diameter; and a releasable locking mechanism mounted to the support rod of the limb holder, wherein the releasable locking mechanism comprises a first key comprising a first keyway and a second key comprising a second keyway, wherein the second key is slidably connected to the first key, wherein the first key is biased away from the second key, wherein the first keyway and the second keyway overlap to form an opening at least as large as the second diameter when an inwardly-directed force is applied to the first key so as to overcome the bias, and further wherein the opening is reduced to a size smaller than the second diameter when the inwardly-directed force is released from the first key.

In another preferred form of the present invention, there is provided a method of mounting a surgical boot to a support rod of a limb holder, the method comprising:

providing a surgical boot mount, the surgical boot mount comprising:
- a projection having a first section and a second section, wherein the first section is attached to the sole of the surgical boot, wherein the first section comprises a first diameter and the second section comprises a second diameter, and further wherein the second diameter is larger than the first diameter; and
- a releasable locking mechanism mounted to the support rod of the limb holder, wherein the releasable locking mechanism comprises a first key comprising a first keyway and a second key comprising a second keyway, wherein the second key is slidably connected to the first key, and further wherein the first key is biased away from the second key;

applying an inwardly-directed force to the first key so as overcome the bias and cause the first keyway and the second keyway to overlap to form an opening at least as large as the second diameter;

inserting the projection into the opening;

releasing the inwardly-directed force from the first key so that the opening is reduced to a smaller size than the second diameter of the projection, whereby to mount the surgical boot to the support rod of the limb holder.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 47-52 are schematic views of a novel quick-connect universal boot mount formed in accordance with the present invention; and FIG. 53 is a schematic view showing further details of the locking mechanism of the quick-connect universal boot mount shown in FIGS. 47-52.

DETAILED DESCRIPTION OF THE PREFERRED EMBODIMENTS

1. First Embodiment of the Invention

Figure 1:
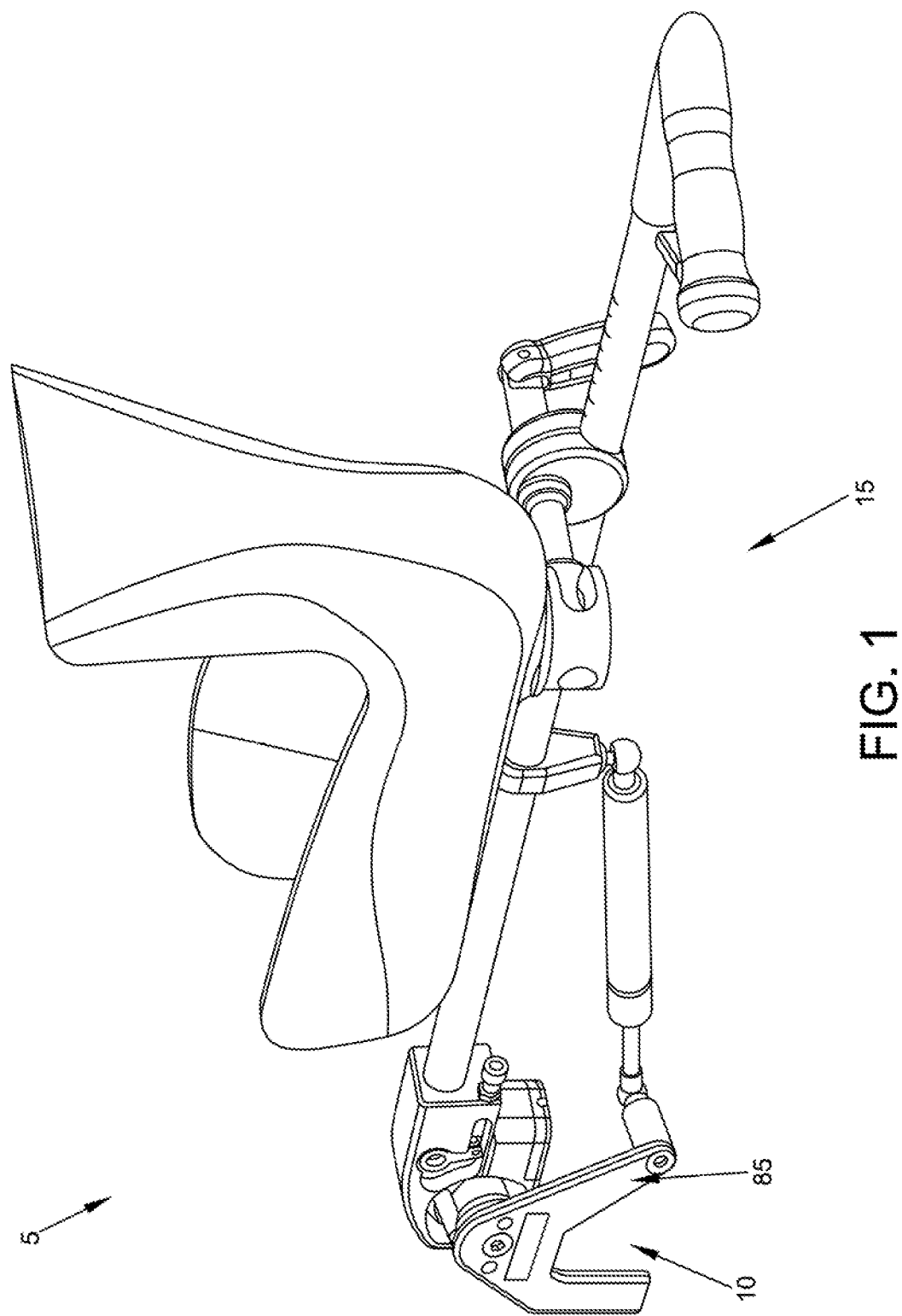
FIG. 1 is a schematic view of an adjustable leg holder formed in accordance with the present invention, wherein the cover of the adjustable leg holder has been removed to show internal structure.
Figure 2:
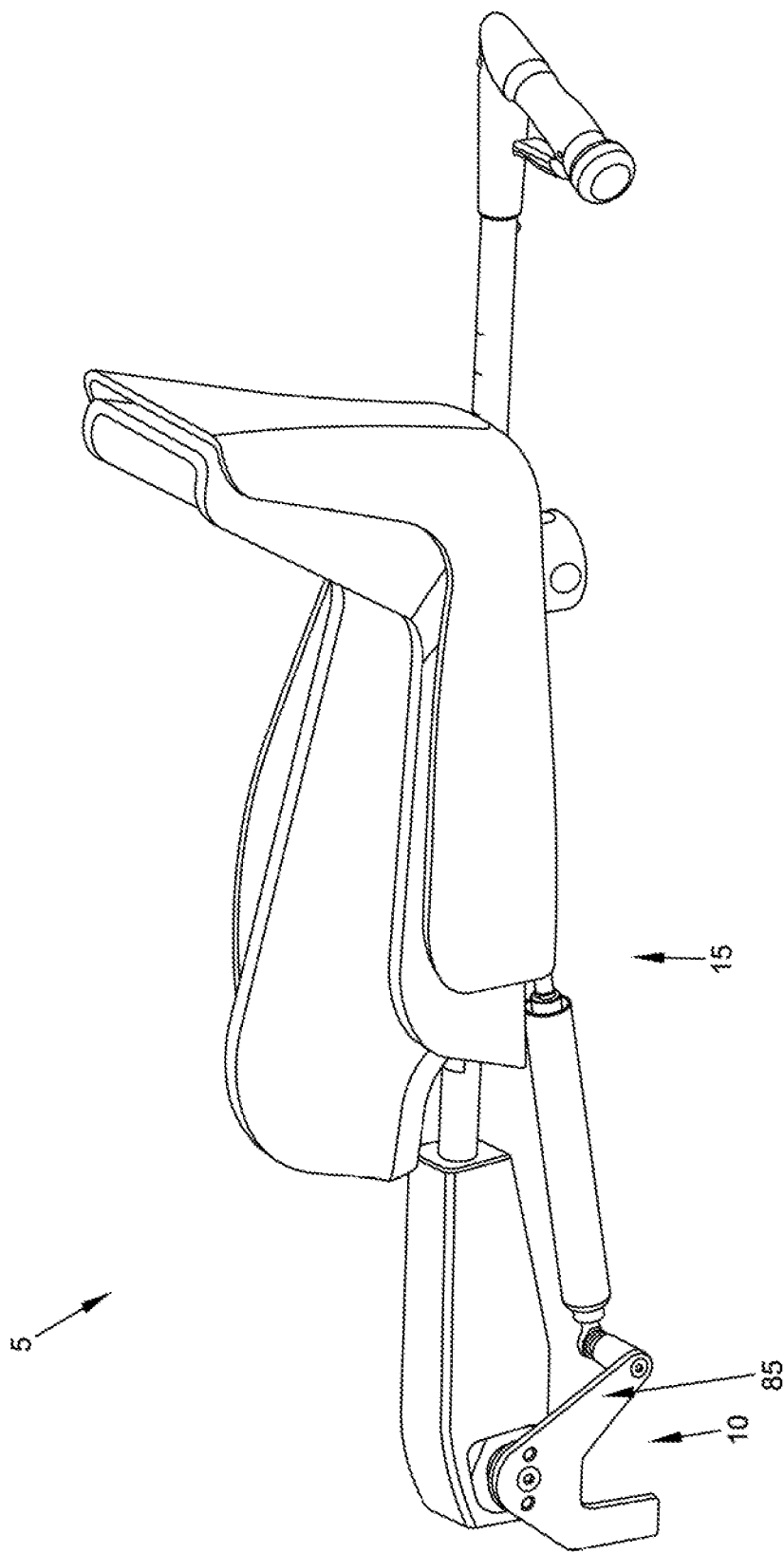
FIG. 2 is another schematic view of the adjustable leg holder shown in FIG. 1.
Figure 3:
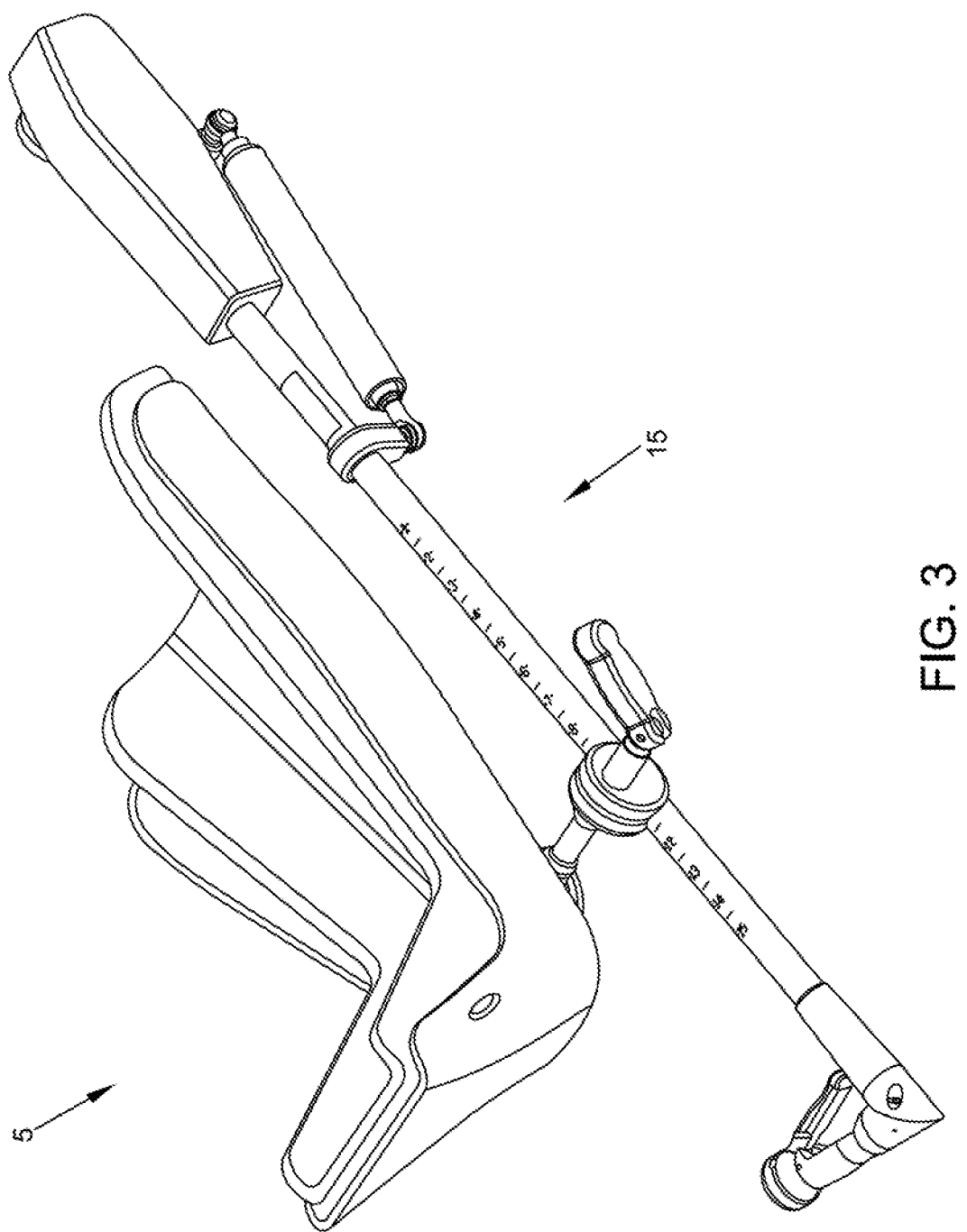
FIG. 3 is another schematic view of the adjustable leg holder shown in FIG. 1.

Looking first at FIGS. 1-3, there is shown a novel stirrup-type leg holder 5 (FIG. 1) formed in accordance with the present invention. Leg holder 5 is constructed so that it may be easily mounted to a surgical table and thereafter easily adjusted at the distal end of the leg stirrup in order to alter the position of the leg of a patient. More particularly, leg holder 5 generally comprises a mount assembly 10 (FIG. 1) for mounting leg holder 5 to a surgical table, and a leg support assembly 15 (FIG. 1) for supporting a patient's leg. Leg support assembly 15 is adjustably mounted to mount assembly 10 by a ball-and-socket arrangement as will hereinafter be discussed. As a result of this construction, a physician is able to move leg support assembly 15 along at least three (3) axes of rotation relative to mount assembly 10 (and hence relative to the surgical table). Consequently, in use, a physician is also able to move a patient's leg that is supported by leg support assembly 15 along at least three (3) axes of rotation relative to the surgical table.

1A. Mount Assembly

Figure 4:
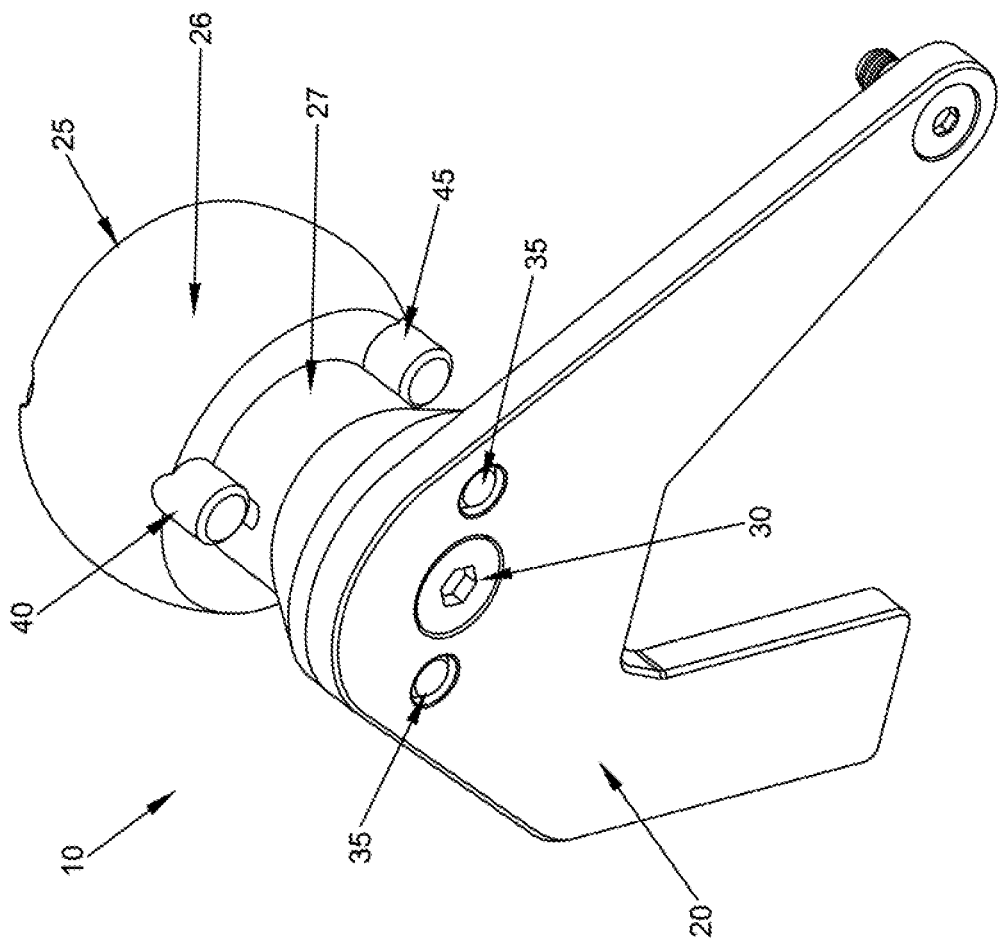
FIG. 4 is a schematic view of the mount assembly of the adjustable leg holder shown in FIG. 1.
Figure 5:
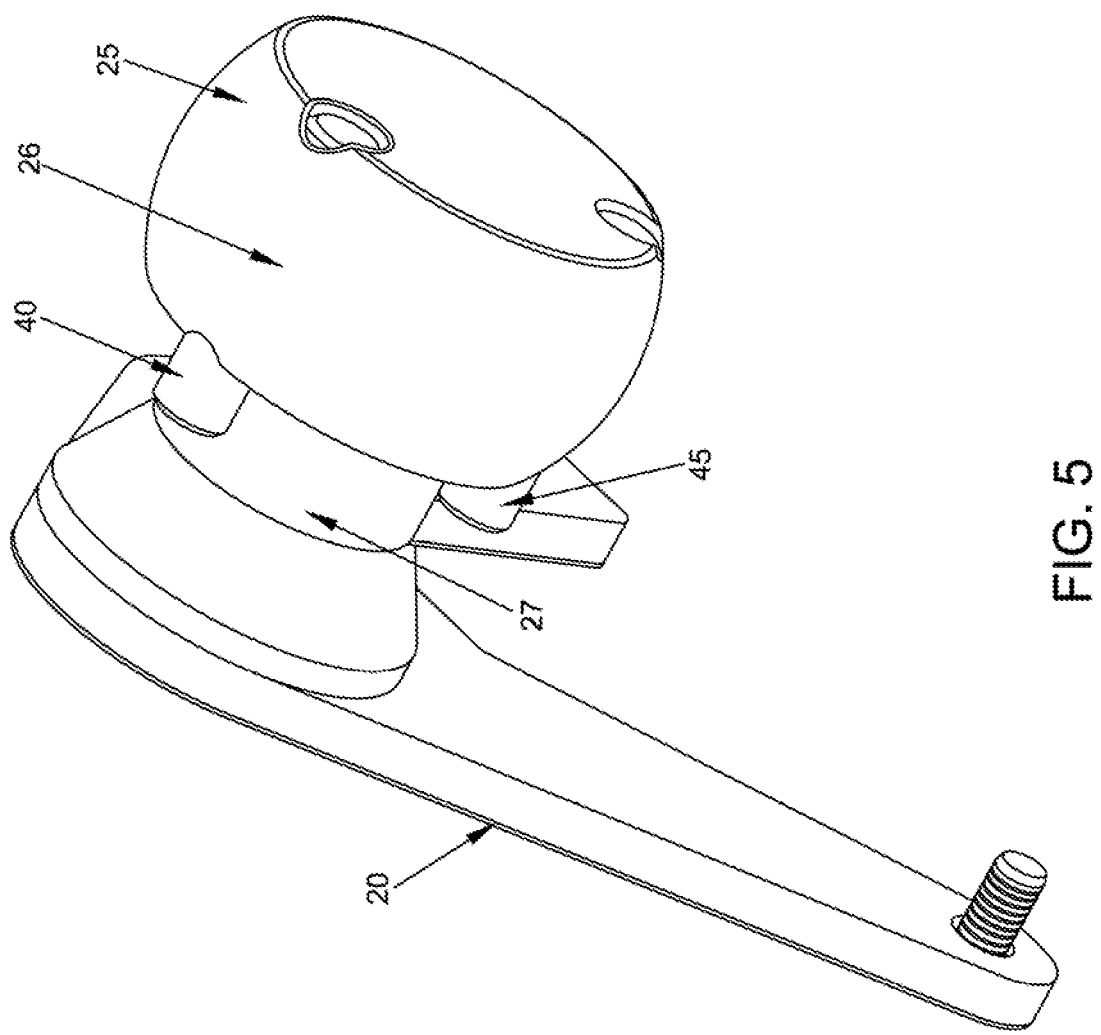
FIG. 5 is another schematic view of the mount assembly shown in FIG. 4.

In one preferred embodiment of the invention, and looking now at FIGS. 4 and 5, mount assembly 10 comprises a mounting bracket 20 (FIG. 4) and semi-ball 25 (FIG. 4). Semi-ball 25 comprises an outer surface 26 (FIG. 4) following a spheroidal geometry, and a neck 27 (FIG. 4) extending along the longitudinal axis of the semi-ball. Semi-ball 25 is fixedly attached to mounting bracket by a bolt 30 (FIG. 4) which extends into neck 27. Pegs 35 (FIG. 4) pass from neck 27 of semi-ball 25 into mounting bracket 20 so as to prevent rotation of semi-ball 25 with respect to mounting bracket 20. Semi-ball 25 also comprises an upper limiting pin 40 (FIG. 4) and a lower limiting pin 45 (FIG. 4) which limit the range of motion of leg support assembly 15 relative to mount assembly 10, as will hereinafter be discussed. Upper limiting pin 40 and lower limiting pin 45 extend parallel to neck 27.

1B. Leg Support Assembly

Turning now to FIGS. 6-15, leg support assembly 15 generally comprises a support rod 50 (FIG. 6) having a proximal end and a distal end, a clamping assembly 55 (FIG. 8) mounted to the proximal end of support rod 50, and a handle 60 (FIG. 6) and an actuating element or lever 65 (FIG. 6) mounted to the distal end of support rod 50. Leg support assembly 15 also comprises a stirrup boot 70 (FIG. 6) for receiving the lower leg and foot of a patient. Boot 70 may be mounted on slidable adjuster 75 (FIG. 7), which is itself slidably mounted on support rod 50 intermediate its proximal and distal ends. Slidable adjuster 75 allows boot 70 to be moved along the length of support rod 50 so as to accommodate the anatomy of differently-sized patients.

Figure 6:
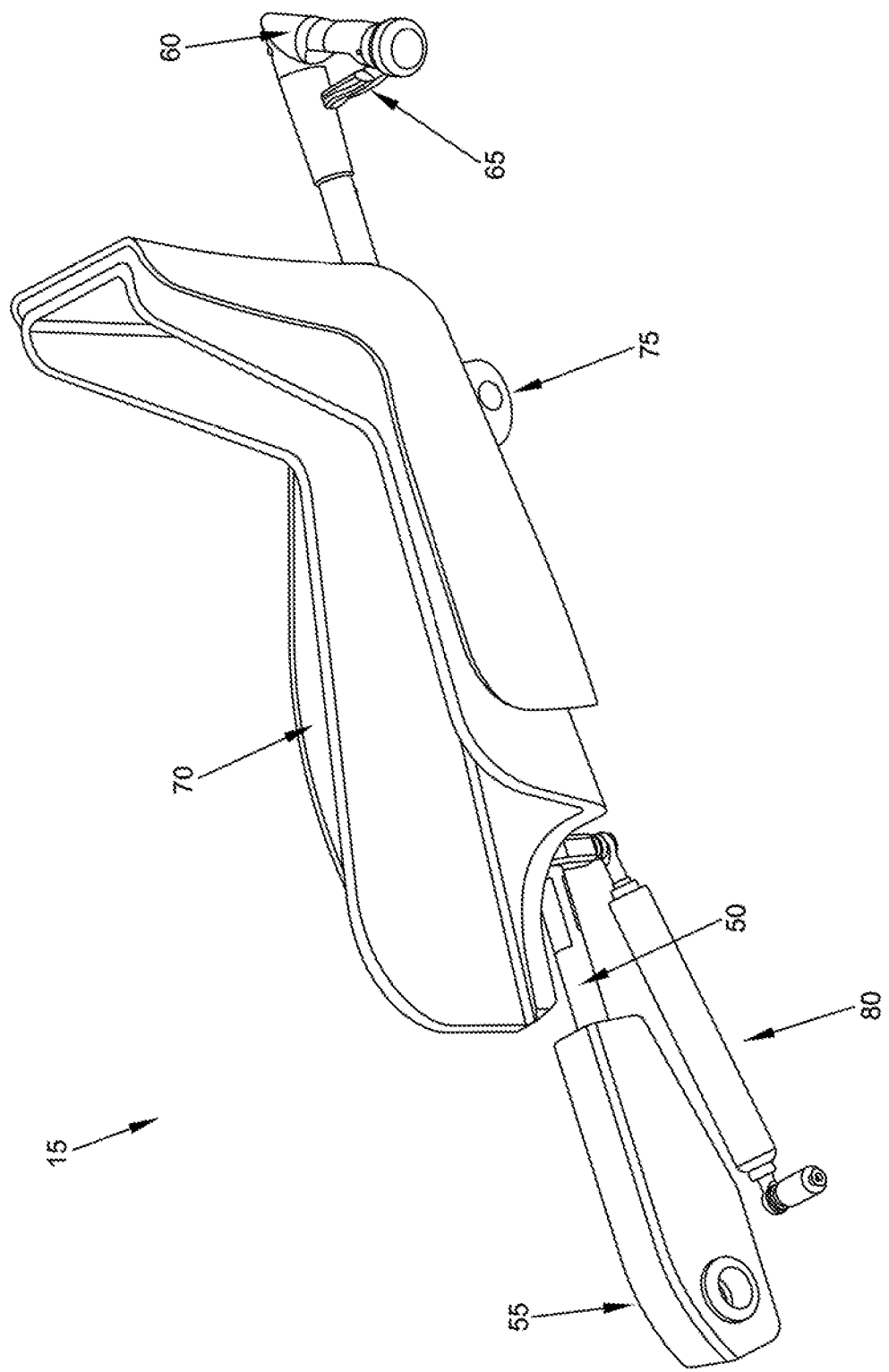
FIG. 6 is a schematic view of the leg support assembly of the adjustable leg holder shown in FIG. 1.
Figure 7:
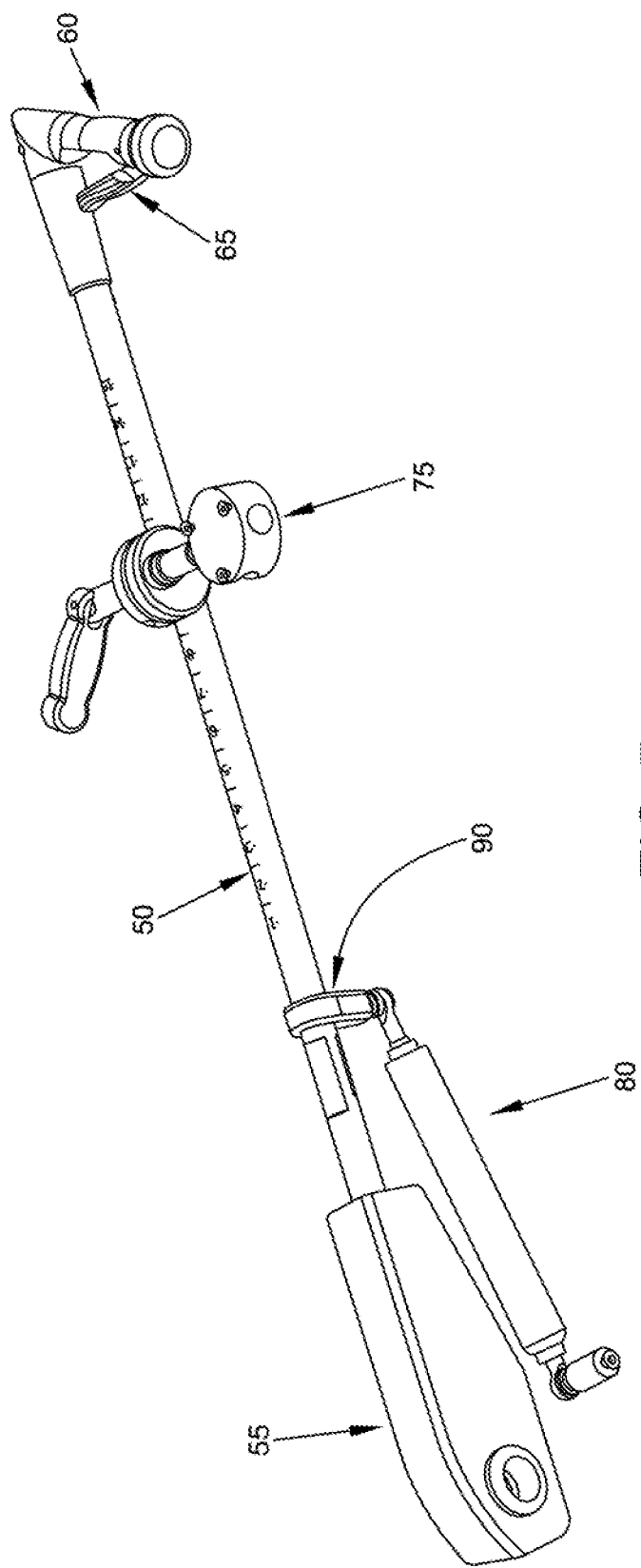
FIG. 7 is a schematic view of the leg support assembly shown in FIG. 6, but with the boot component removed.
Figure 8:
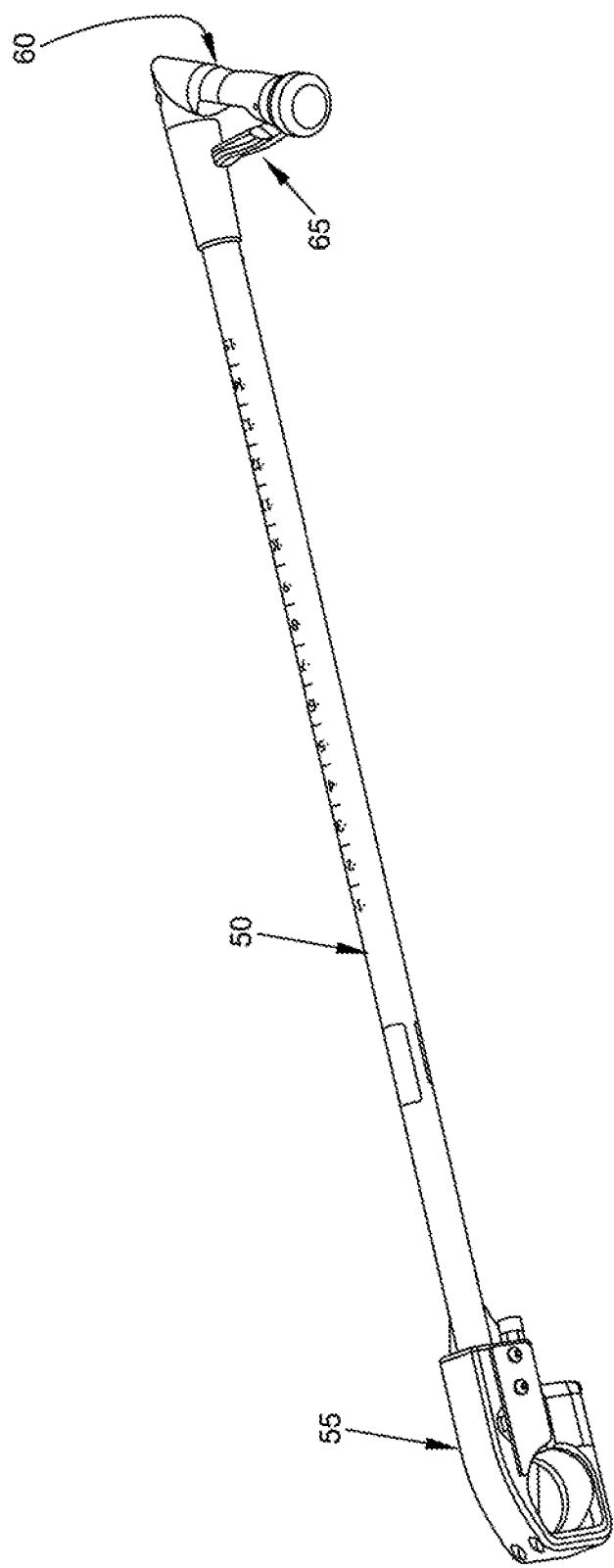
FIG. 8 is a schematic view of the leg support assembly with selected components removed, showing the support rod, the clamping assembly and the handle of the support rod.
Figure 9:
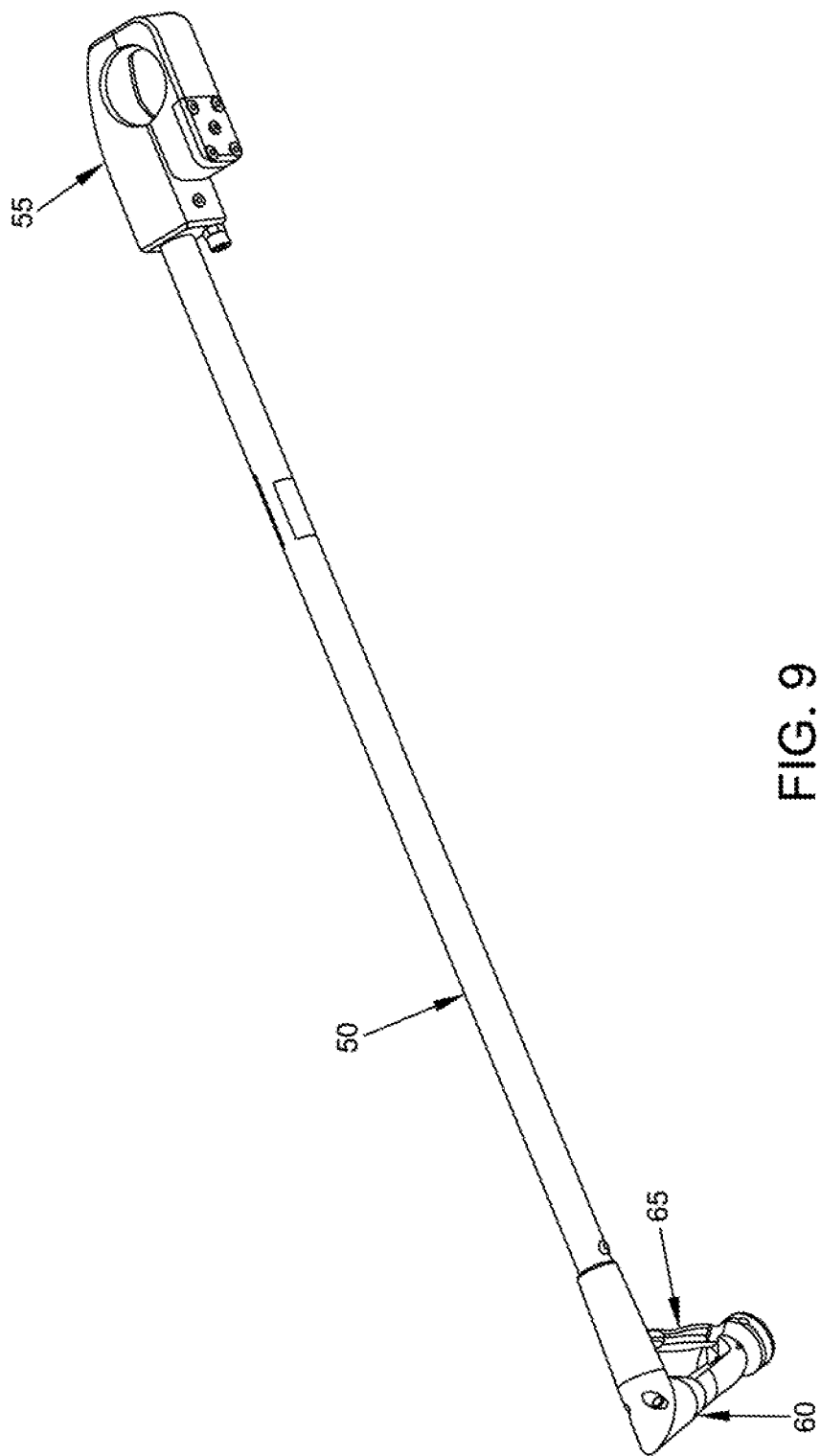
FIG. 9 is another schematic view showing the apparatus of FIG. 8.

Leg support assembly 15 preferably also comprises a gas cylinder 80 (FIG. 6). The proximal end of gas cylinder 80 is mounted to distal leg 85 (FIG. 1) of mounting bracket 20 (FIGS. 1 and 2) and the distal end of gas cylinder 80 is mounted to a collar 90 (FIG. 7) which is fixedly mounted to support rod 50. The air pressure inside gas cylinder 80 is preferably set so as to approximately offset the combined weight of leg support assembly 15 and a patient's leg so as to render movement of the apparatus relatively easy during use. In the present device, gas cylinder 80 may also be used to limit the travel in the lithotomy dimension, in the sense that clamping assembly 55 can move in the high lithotomy direction until gas cylinder 80 reaches its full extension length and clamping assembly 55 can move in the low lithotomy dimension until it reaches its full compression length. Accordingly, the force exerted by gas cylinder 80 allows a physician to easily move leg support assembly 15 (with a patient's leg disposed thereon) with one hand during use.

1C. Clamping Element

Figure 10:
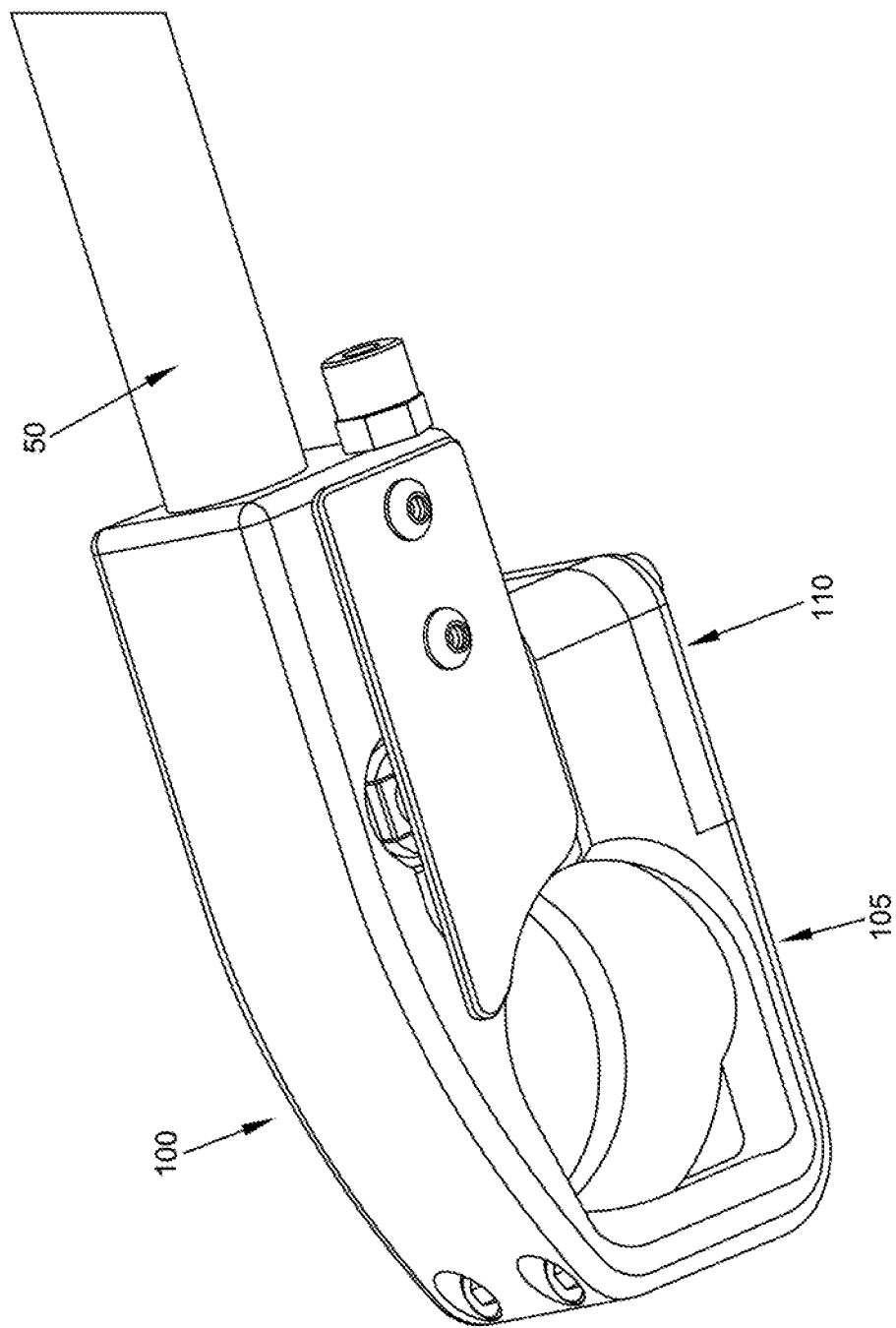
FIG. 10 is a schematic view of the clamping assembly portion of the leg support assembly.
Figure 11:
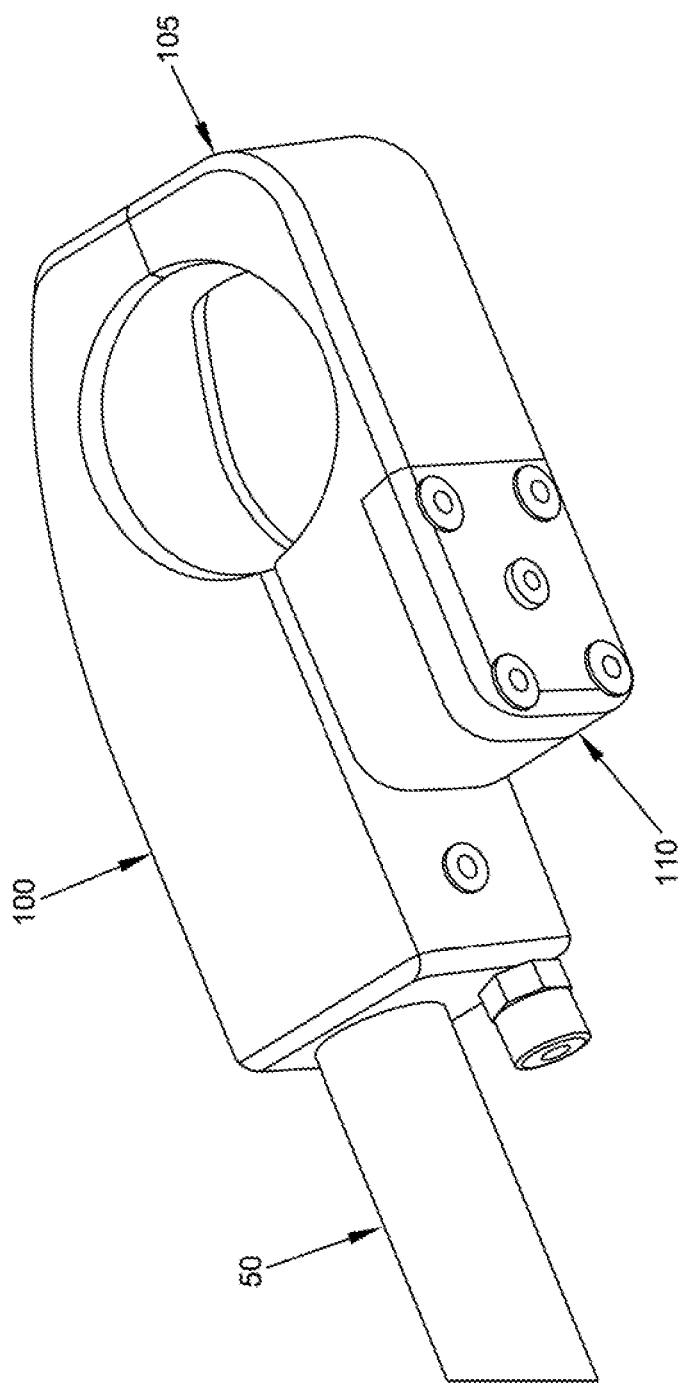
FIG. 11 is another schematic view of the clamping assembly shown in FIG. 10.
Figure 12:
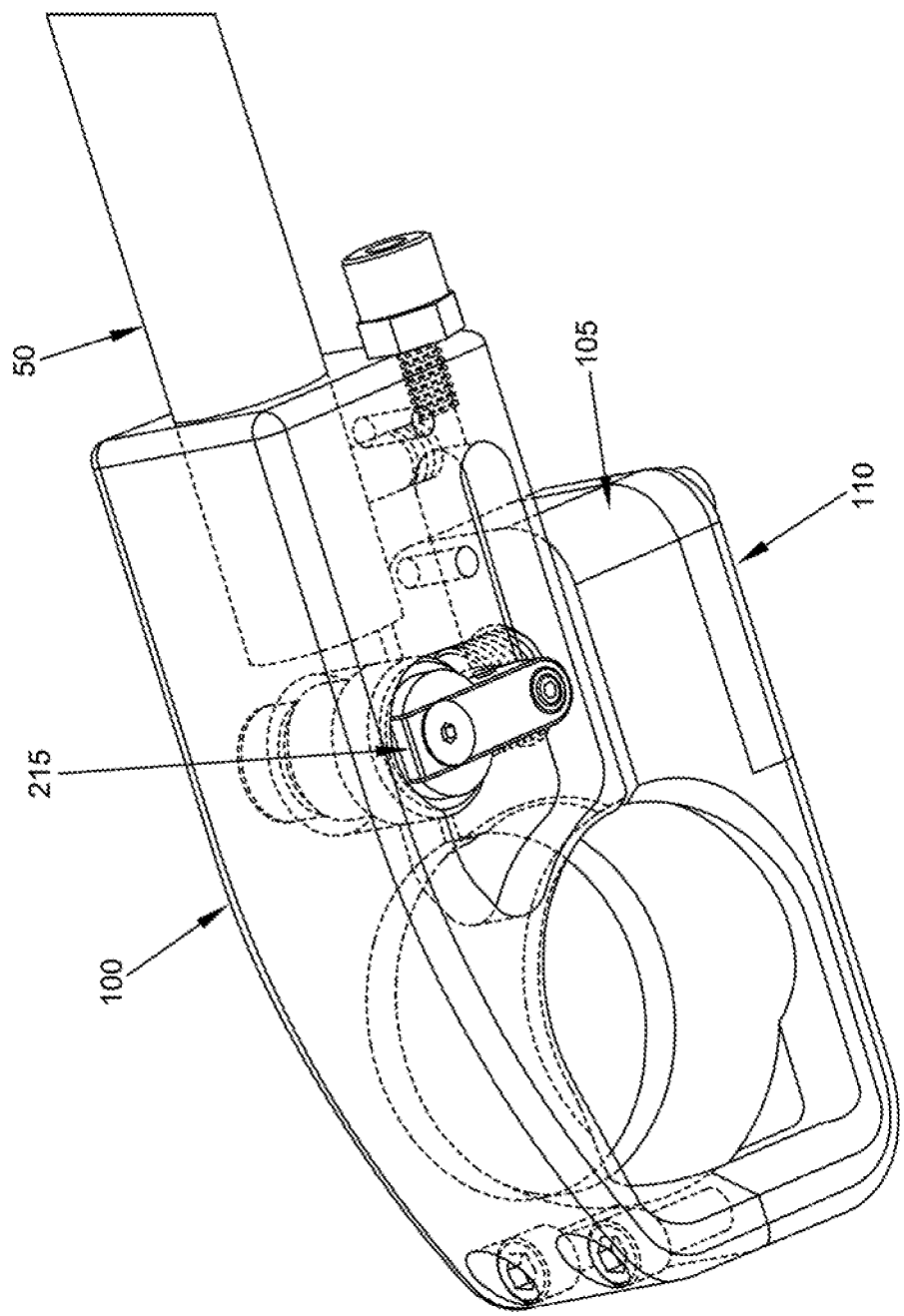
FIG. 12 is a schematic view similar to that shown in FIG. 10, but with the upper jaw of the clamping assembly rendered transparent so as to show internal structure.
Figure 13:
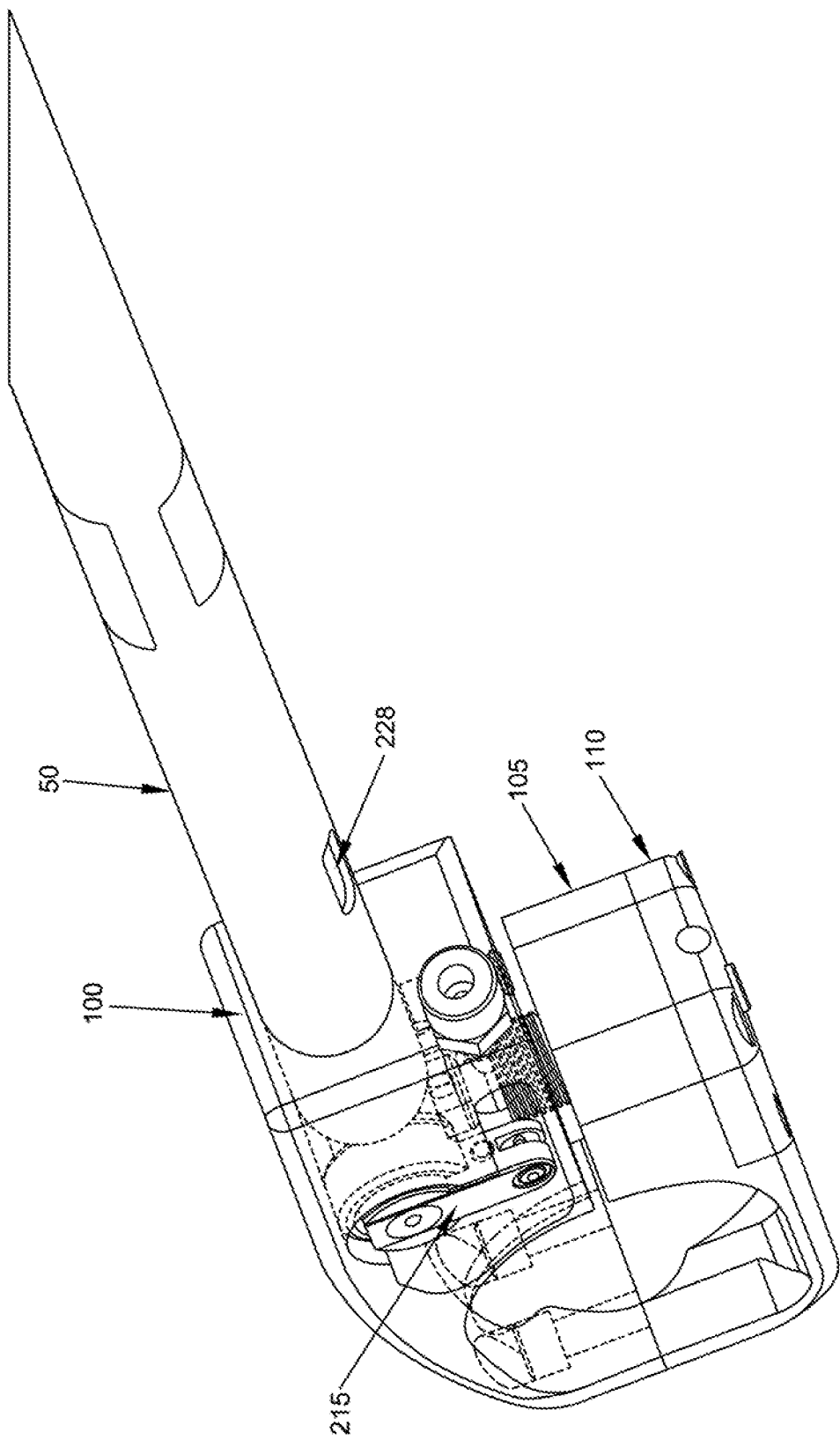
FIG. 13 is another schematic view of a portion of the leg support assembly with the upper jaw of the clamping assembly rendered transparent.
Figure 14:
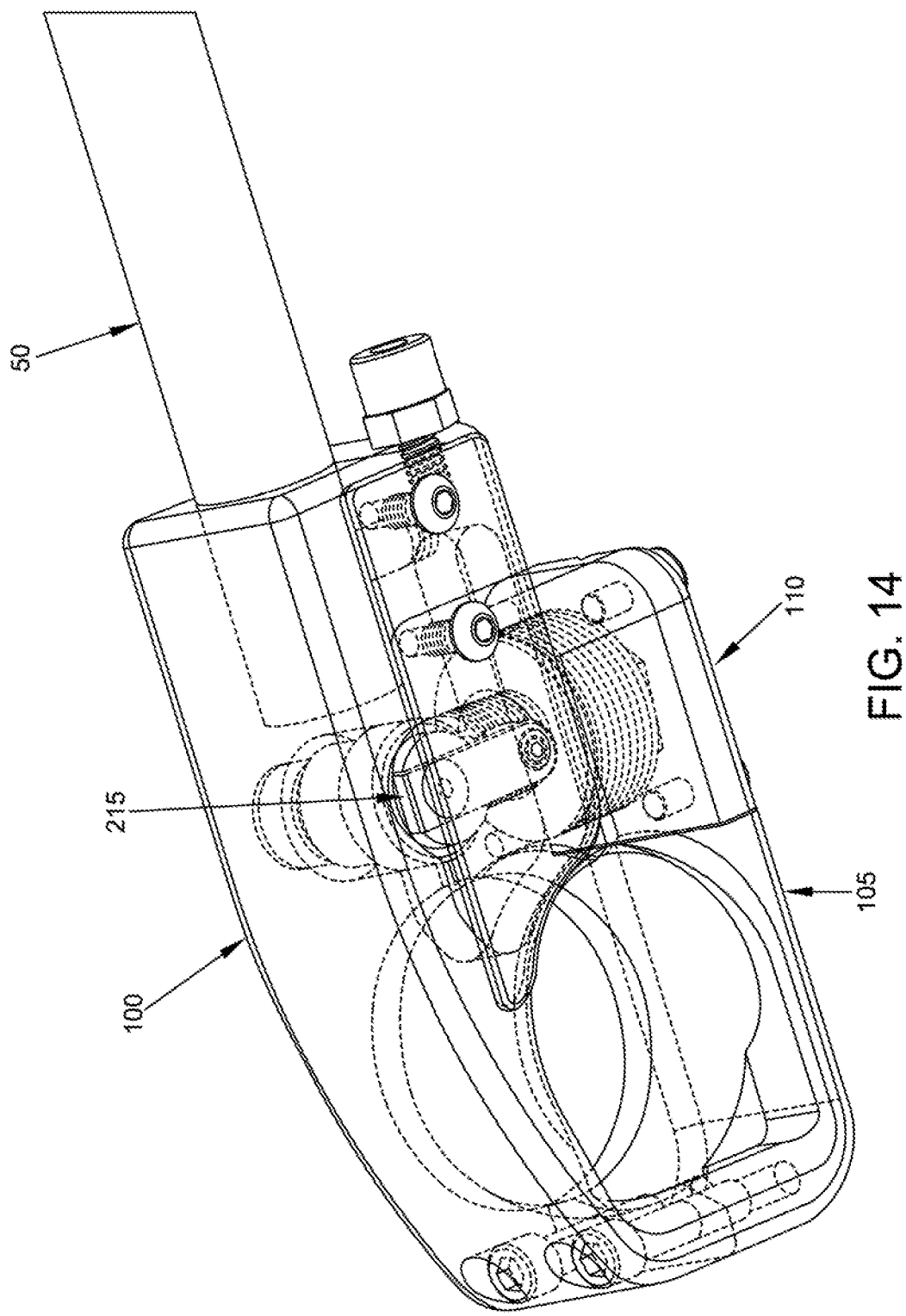
FIG. 14 is a schematic view similar to that shown in FIG. 12, but with the lower jaw also rendered transparent so as to show internal structure.
Figure 15:
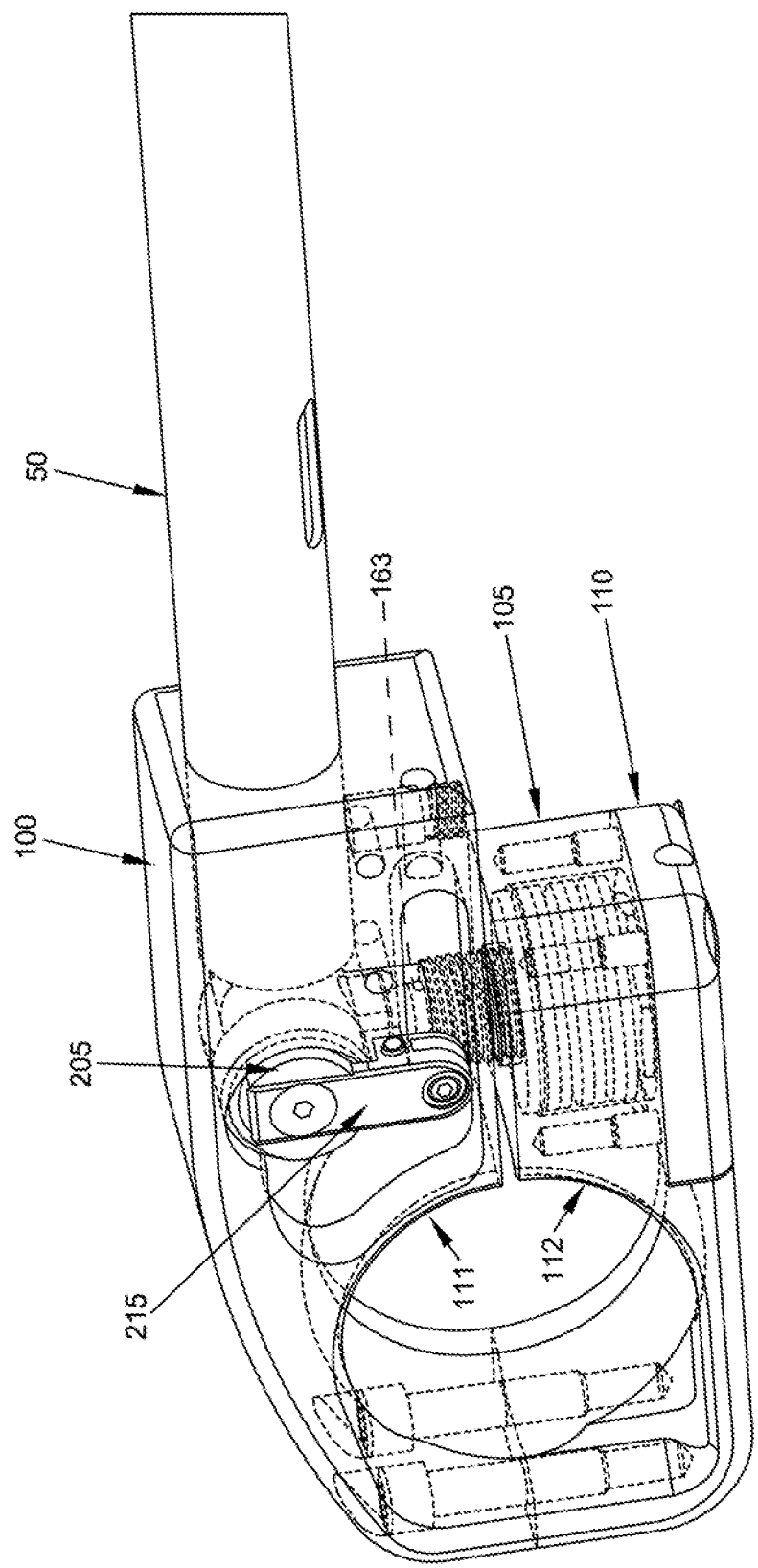
FIG. 15 is a schematic view of the clamping assembly with both the upper and lower jaws rendered transparent.

Looking now at FIGS. 8-17, clamping assembly 55 comprises an upper jaw 100 (FIG. 10), a lower jaw 105 (FIG. 10) and a bottom plate 110 (FIG. 10). Upper jaw 100 comprises a concave gripping surface 111 (FIG. 15) for engaging the spheroidal outer surface 26 of semi-ball 25, and lower jaw 105 comprises a concave gripping surface 112 (FIG. 15) for engaging the spheroidal outer surface 26 of semi-ball 25. A bore 115 (FIG. 17) and counter bore 116 (FIG. 17) extend through lower jaw 105. Bore 115 is of a first diameter near the top surface 120 (FIG. 16) of lower jaw 105 and counterbore 116 is of a second, larger diameter deep to top surface 120 of lower jaw 105. An annular shoulder 117 (FIG. 17) is disposed at the intersection of bore 115 and counterbore 116.

A cavity 125 (FIG. 17) that is coaxial with bore 115 and counterbore 116 extends into upper jaw 100 from the bottom surface 130 (FIG. 17) of upper jaw 100. A portion of cavity 125 is threaded so as to threadably engage the shaft of a spring compression bolt (see below).

A bore 135 (FIG. 17) and counterbore 136 (FIG. 17) extend through bottom plate 110. Bore 135 is of a first diameter from bottom surface 140 (FIG. 17) of bottom plate 110 until just below top surface 145 (FIG. 17) of bottom plate 110, and counterbore 136 is of a second, larger diameter. Bore 135 is threaded to engage a tension set screw (see below).

Figure 17:
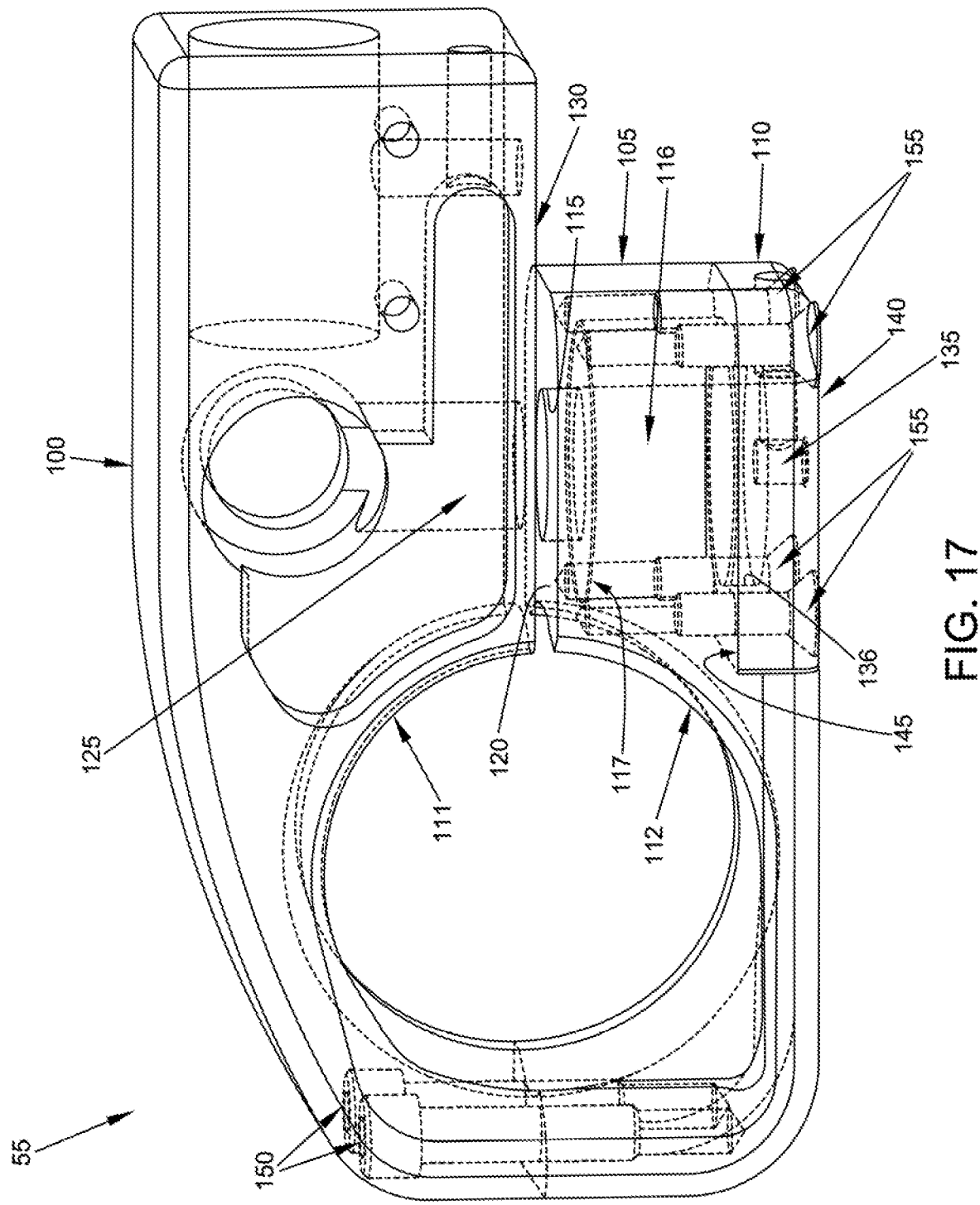
FIG. 17 is a schematic view of the clamping assembly with both the upper and lower jaws rendered transparent, with the bottom plate of the lower jaw rendered transparent, and with various internal components omitted for clarity.

Upper jaw 100 and lower jaw 105 are joined together at one side of clamping assembly 55 by screws 150 (FIG. 17). Bottom plate 110 is joined to lower jaw 105 by screws 155 (FIG. 17).

Figure 16:
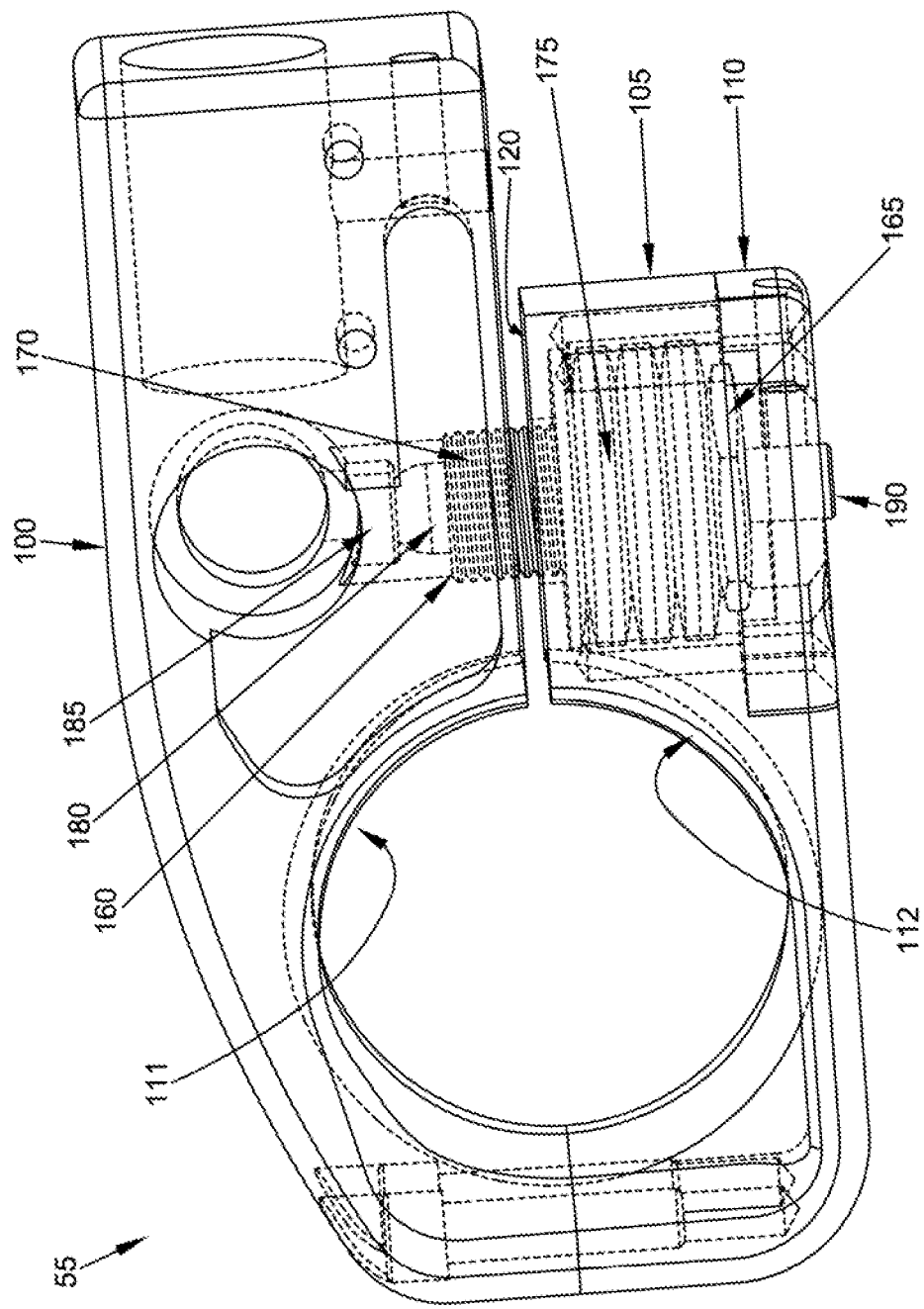
FIG. 16 is a schematic view of the clamping assembly with the upper and lower jaws rendered transparent, and with the bottom plate of the lower jaw rendered transparent.
Figure 22:
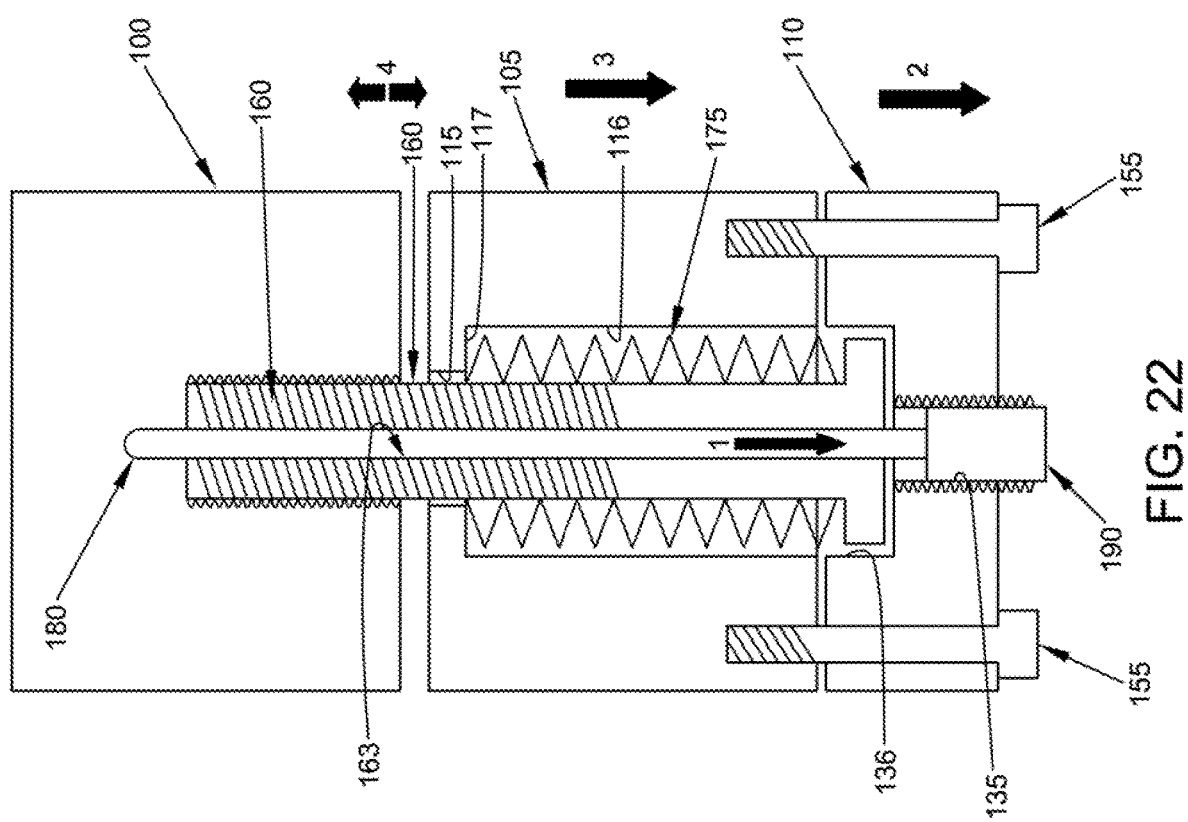
FIG. 22 is a simplified schematic view of selected components of the clamping assembly, showing the forces which act on the various components of the clamping assembly.

Turning now to FIG. 16, there is shown a spring compression bolt 160 (FIG. 16) having a head 165 (FIG. 16) and a shaft 170 (FIG. 16). Spring compression bolt 160 passes through bore 115 and counterbore 116 of lower jaw 105. A portion of shaft 170 is threaded. Spring compression bolt 160 is configured with a central bore 163 (FIGS. 15 and 22) extending therethrough. Shaft 170 of spring compression bolt 160 is threadably engaged in cavity 125 of upper jaw 100, whereby to secure spring compression bolt 160 to upper jaw 100. Head 165 of spring compression bolt 160 partially resides in counterbore 116 of lower jaw 105 and in counterbore 136 of bottom plate 110.

Counterbore 116 in lower jaw 105 is sized to accommodate spring element 175 (FIG. 16), which is arranged concentrically around the shaft 170 of spring compression bolt 160. Spring element 175 is captured in counterbore 116 in lower jaw 105, between head 165 of spring compression bolt 160 and the annular shoulder 117 created where counterbore 116 meets bore 115.

On account of the foregoing construction, spring element 175 normally biases head 165 of spring compression bolt 160 away from top surface 120 of lower jaw 105; inasmuch as the opposite threaded end of spring compression bolt 160 is secured to upper jaw 100, this action normally draws upper jaw 100 and lower jaw 105 together, whereby to draw the concave gripping surface 111 of upper jaw 100 and the concave gripping surface 112 of lower jaw 105 onto spheroidal outer surface 26 of semi-ball 25. In this way, clamping assembly 55 is spring-biased so that it normally grips semi-ball 25.

Spring release pin 180 (FIG. 16) extends through central bore 163 of spring compression bolt 160. The top end of spring release pin 180 stands proud of spring compression bolt 160. The top end of spring release pin 180 may have a hemispherical shape configured to mate with the bottom surface of a cam bearing block 185 (FIG. 16) (see below) which may have a complementary hemispherical cavity. Spring release pin 180 terminates in the bottom end of shaft 170 of spring compression bolt 160 just above head 165 of spring compression bolt 160.

Bottom plate 110 receives a tension set screw 190 (FIG. 16). Tension set screw 190 is threadably engaged in bore 135 of bottom plate 110 and engages the lower end of spring release pin 180, as will hereinafter be discussed.

1D. Cam Mechanism

Figure 18:
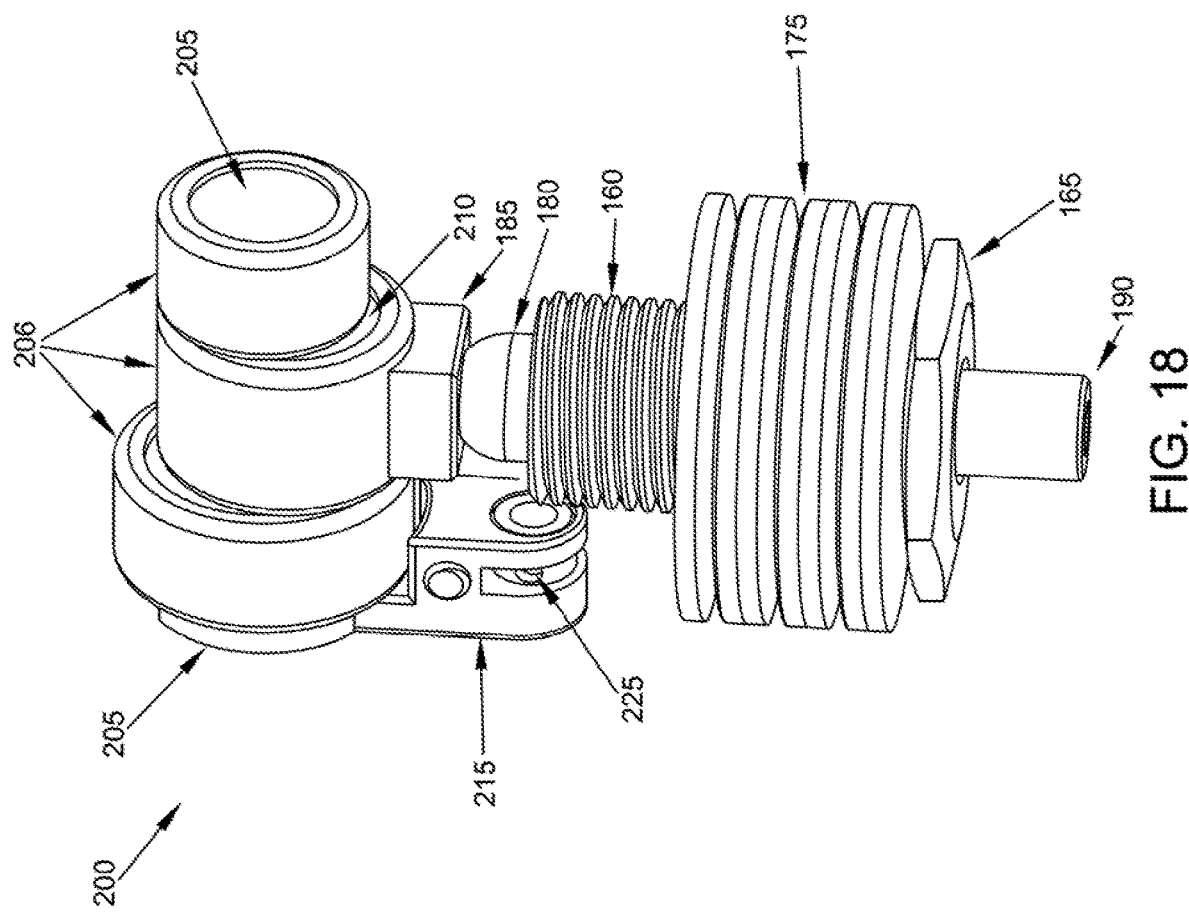
FIG. 18 is a schematic view of the cam mechanism and other selected internal components of the clamping assembly.
Figure 19:
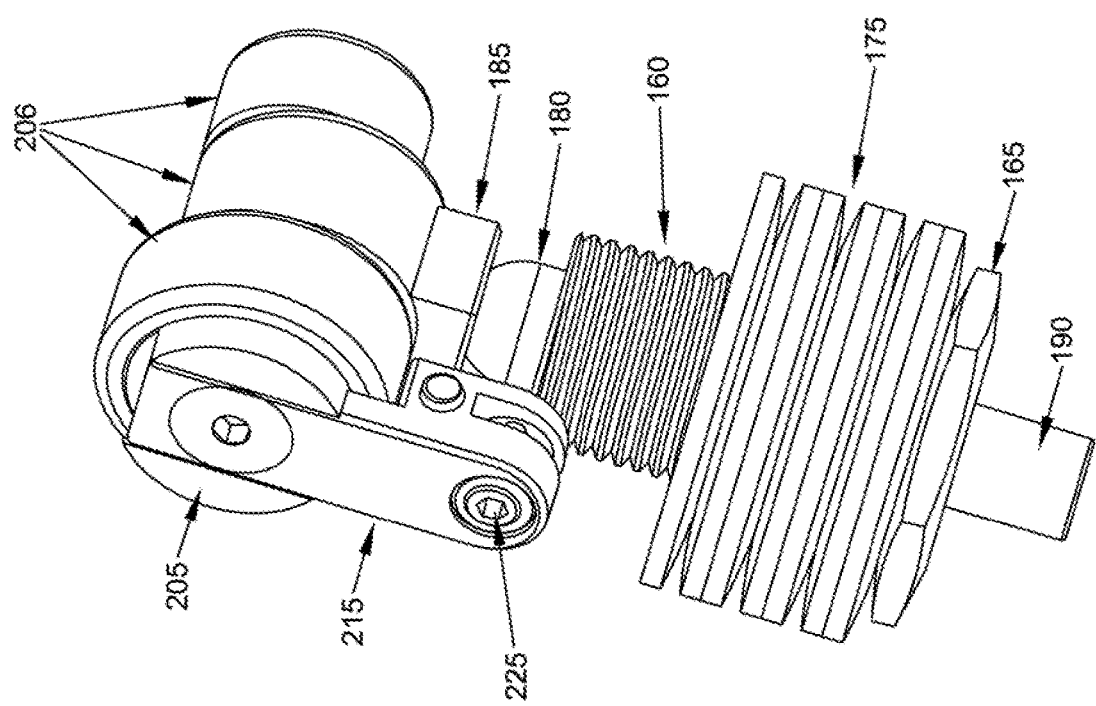
FIG. 19 is another schematic view of the components shown in FIG. 18.
Figure 20:
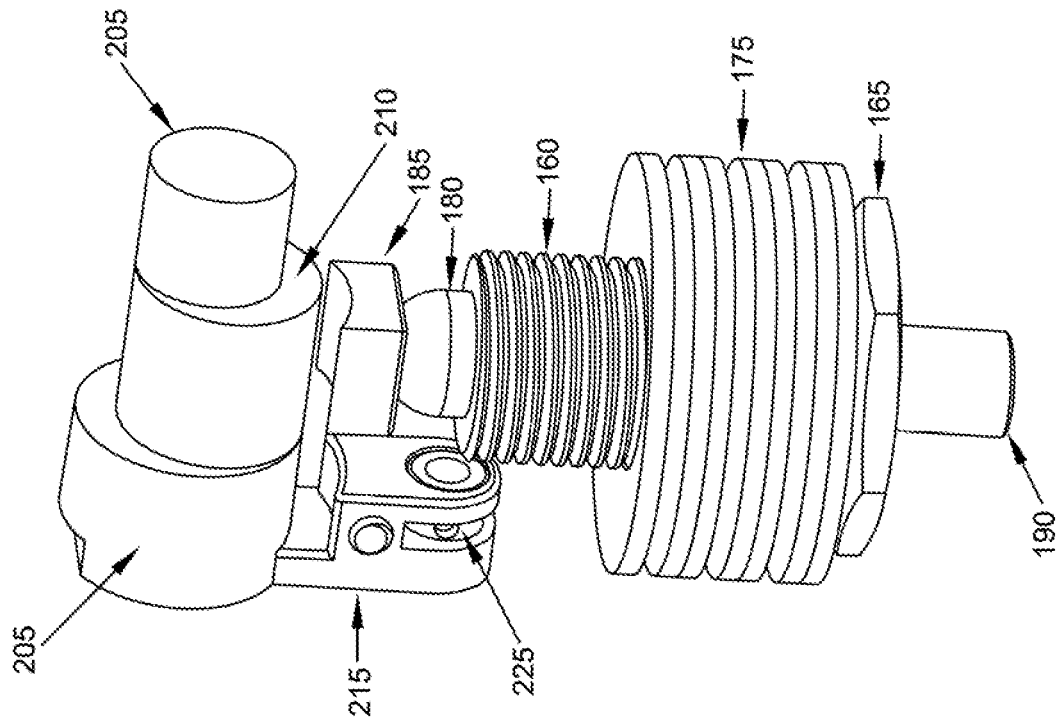
FIG. 20 is a view similar to that of FIG. 18, but with the cam bearings removed so that the entire cam is exposed.
Figure 21:
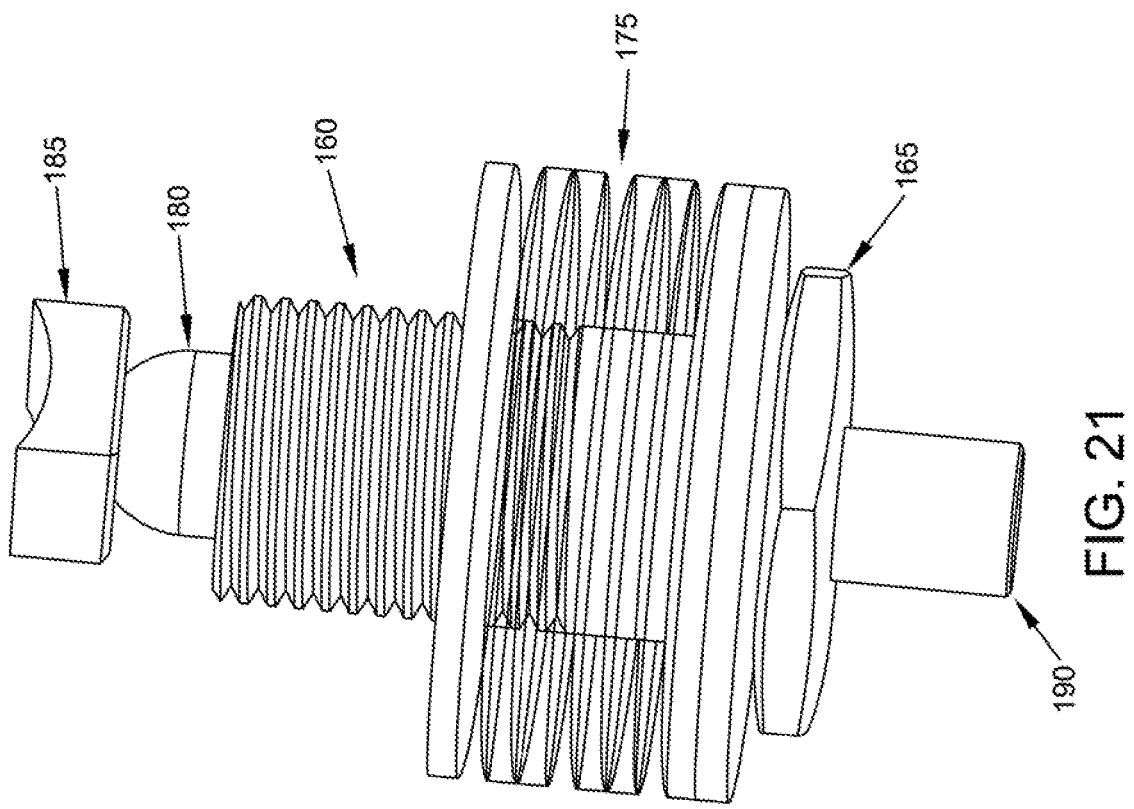
FIG. 21 is a schematic view of selected portions of the clamping assembly, with some components rendered transparent for clarity.
Figure 23:
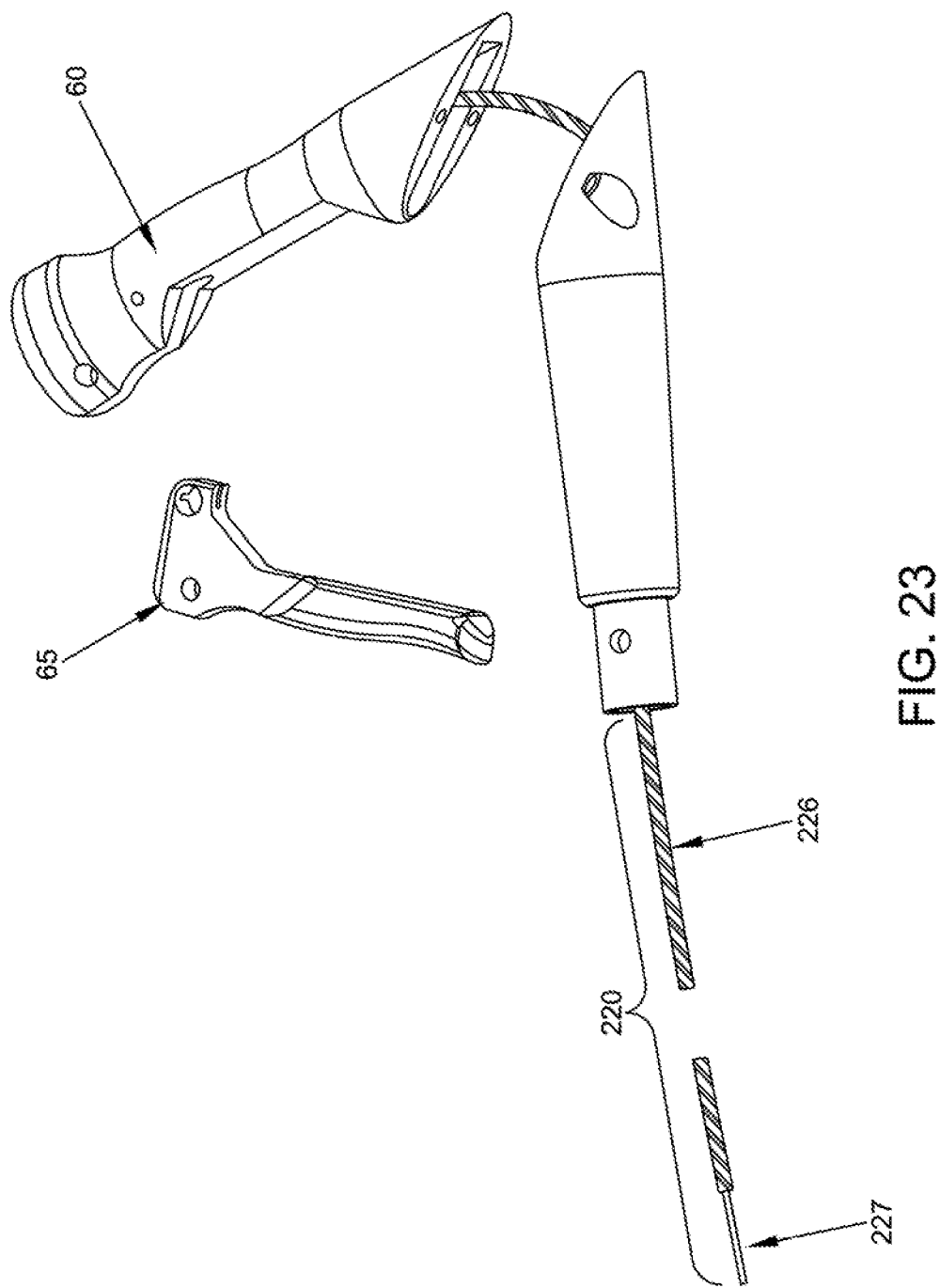
FIG. 23 is a schematic view of selected portions of the release mechanism for selectively releasing the clamping mechanism.

Looking now at FIGS. 12-16 and 18-23, there is shown a cam mechanism 200 (FIG. 18) for selectively opening clamping assembly 55. Cam mechanism 200 is disposed in upper jaw 100 (upper jaw 100 is omitted from FIGS. 18-21 for clarity) and comprises a cam 205 (FIG. 18) which is received in bearings 206 (FIG. 18). Cam 205 contains an eccentric 210 (FIG. 18) which exerts a downward force on cam bearing block 185 when cam 205 is rotated, as will hereinafter be discussed. Cam arm 215 (FIG. 18) is configured to receive one end of cable 220 (FIG. 23) at cable anchor 225 (FIG. 20). The other end of cable 220 is connected to actuating element or lever 65 (FIG. 23). Cam arm 215 is fixedly connected to cam 205.

As will hereinafter be discussed, when cable 220 is anchored to cam arm 215 and cable 220 is pulled (i.e., by pulling on actuating element or lever 65), it causes cam arm 215 to move, whereby to cause cam 205 to rotate. The rotation of cam 205, and the corresponding rotation of eccentric 210, causes eccentric 210 to push down on cam bearing block 185, which then pushes down on spring release pin 180. As will hereinafter be discussed, this action causes upper jaw 100 and lower jaw 105 to separate, whereby to allow clamping assembly 55 and any appendages attached thereto (e.g., support rod 50) to move relative to semi-ball 25 (and hence relative to the surgical table to which semi-ball 25 is attached).

Cam arm 215 is moved by the action of cable 220, which may be similar in construction to a brake cable, and generally comprises outer jacket 226 (FIG. 23) and an inner cable 227 (FIG. 23), although the exact configuration may be altered without changing the intention of this invention.

The provision of cable 220 as an actuating means, rather than providing a solid actuating means such as a rod, is advantageous, inasmuch as the cable allows the force applied to cam arm 215 to be routed in almost any direction desired by the physician.

Thus, the cable may route the force around bends and corners and allow the positioning of cable actuating element or lever 65 in a more comfortable and/or advantageous position for the physician. In one preferred embodiment of the invention, cable 220 is routed from cable anchor 225, through upper jaw 100, into support rod 50 via portal 228 (FIG. 13), and then back through support rod 50 to handle 60.

Actuating element or lever 65 itself may be configured in the manner of a brake lever (FIGS. 3, 6-9 and 23), and like cam arm 215, provides a force multiplier that, by decreasing the force necessary to open spring element 175 and thus release the clamping force of upper jaw 100 and lower jaw 105 from the semi-ball 25, improves the action of the device for the physician.

It is important to realize that when tension is applied to cable 220 by the physician through actuating element or lever 65, cam arm 215 applies a rotational force to cam 205 which forces lower jaw 105 to separate (against the biasing force of spring element 175) from upper jaw 100, whereby to cause clamping assembly 55 to open. This action releases the clamping force of concave gripping surface 111 of upper jaw 100 and the concave gripping surface 112 of lower jaw 105 on semi-ball 25, which then allows clamping assembly 55 to move about any and/or all of the axes of semi-ball 25.

1E. Further Details Regarding Opening and Closing of the Clamping Assembly

When eccentric 210 is not exerting force on cam bearing block 185 (i.e., when clamping assembly 55 is in its resting or non-actuated state), clamping assembly 55 is clamped around semi-ball 25. The force exerted on semi-ball 25 by upper jaw 100 and lower jaw 105 of clamping element 55 is sufficient to prevent relative movement between semi-ball 25 and clamping assembly 55.

More particularly, when clamping assembly 55 is in its resting or non-actuated state, spring element 175 is exerting a force on spring compression bolt 160 which pulls upper jaw 100 and lower jaw 105 toward one another. This force urges the concave gripping surface 111 of upper jaw 100 and the concave gripping surface 112 of lower jaw 105 against the spheroidal outer surface 26 of semi-ball 25. The force exerted on semi-ball 25 by concave gripping surface 111 of upper jaw 100 and concave gripping surface 112 of lower jaw 105 is sufficient to prevent relative movement between clamping assembly 55 and semi-ball 25. Thus, support rod 50 and all of the components attached thereto (e.g., boot 70) are similarly prevented from moving relative to semi-ball 25, resulting in the immobilization of leg support assembly 15 with respect to the surgical table.

When cam mechanism 200 is actuated (e.g., by pulling actuating element or lever 65), lower jaw 105 is forced (against the bias of spring element 175) to move away from upper jaw 100, thereby permitting clamping assembly 55 (and the components attached thereto) to move relative to semi-ball 25.

More particularly, cam mechanism 200 is actuated by rotating cam 205 (e.g., by pulling cable 220, which is connected to cam arm 215, which is connected to cam 205). When cam 205 is rotated, eccentric component 210 of cam 205 exerts a downward force on cam bearing block 185, which in turn exerts a downward force on spring release pin 180. This motion is represented by Arrow 1 shown in FIG. 22.

As previously discussed, spring release pin 180 runs through central bore 163 of spring compression bolt 160, and the downward force on spring release pin 180 causes it to contact and exert a downward force on tension set screw 190. Inasmuch as tension set screw 190 is fixed to bottom plate 110, the downward motion of spring release pin 180 applies a downward force to bottom plate 110. This motion is represented by Arrow 2 shown in FIG. 22.

The downward force applied to bottom plate 110 by spring release pin 180 is transmitted to lower jaw 105 by virtue of screws 155 which connect bottom plate 110 to lower jaw 105. This motion is represented by Arrow 3 shown in FIG. 22. As a result, lower jaw 105 is forced downward (against the bias of spring element 175) and hence away from upper jaw 100. This motion is represented by Arrow 4 shown in FIG. 22.

By increasing the distance between upper jaw 100 and lower jaw 105, concave gripping surface 111 of upper jaw 100 and concave gripping surface 112 of lower jaw 105 are each moved away from the spheroidal outer surface 26 of semi-ball 25. Accordingly, the force exerted by clamping assembly 55 on semi-ball 25 is reduced, allowing relative movement between the two components as discussed above.

Clamping assembly 55 may be restored to its initial state (i.e., that which prohibits relative movement between semi-ball 25 and clamping assembly 55) by discontinuing the application of force to the cam mechanism 200 (e.g., by discontinuing the application of force to cable 220 via actuating element or lever 65). By discontinuing the application of force to cam mechanism 200, the force exerted by cam 205 on spring release pin 180 will be overcome by the force exerted by spring element 175 (i.e., on head 165 of spring compression bolt 160 and annular shoulder 117 at the intersection of bore 115 and counterbore 116), which in turn exerts an upward force on lower jaw 105. This has the effect of reducing the distance between upper jaw 100 and lower jaw 105 and allowing clamping assembly 55 to again fit tightly around semi-ball 25, thereby preventing relative movement therebetween.

In addition, as lower jaw 105 and bottom plate 110 return upward, tension set screw 190 exerts an upward force on spring release pin 180, which accordingly pushes cam bearing block 185 upward and rotates cam 205 back to its initial position, with eccentric 210 not exerting downward force on cam bearing block 185.

1F. Use of the First Embodiment of the Invention

Looking now at FIGS. 24-29, to achieve a controlled simulation of a ball-and-socket arrangement of mechanical elements, the present invention uses the truncated or semi-ball 25 gripped by upper jaw 100 and lower jaw 105, i.e., gripped between concave gripping surface 111 of upper jaw 100 and concave gripping surface 112 of lower jaw 105 that fit around the spheroidal outer surface 26 of semi-ball 25 in a concentric manner.

The range of rotational movement that the device can make around the semi-ball's longitudinal axis is controlled by the compressed and extended length of gas cylinder 80 (see FIG. 6).

The device can move rotationally about two additional axes that are at right angles to each other, and to the previously-described longitudinal axis of semi-ball 25.

These additional rotational motions can be thought of as "pitch" and "yaw", and are controlled by the interaction between a limit surface 300 (FIG. 25) on upper jaw 100 against upper limiting pin 40 and the interaction between a limit surface 305 (FIG. 25) on lower jaw 105 against lower limiting pin 45.

Figure 24:
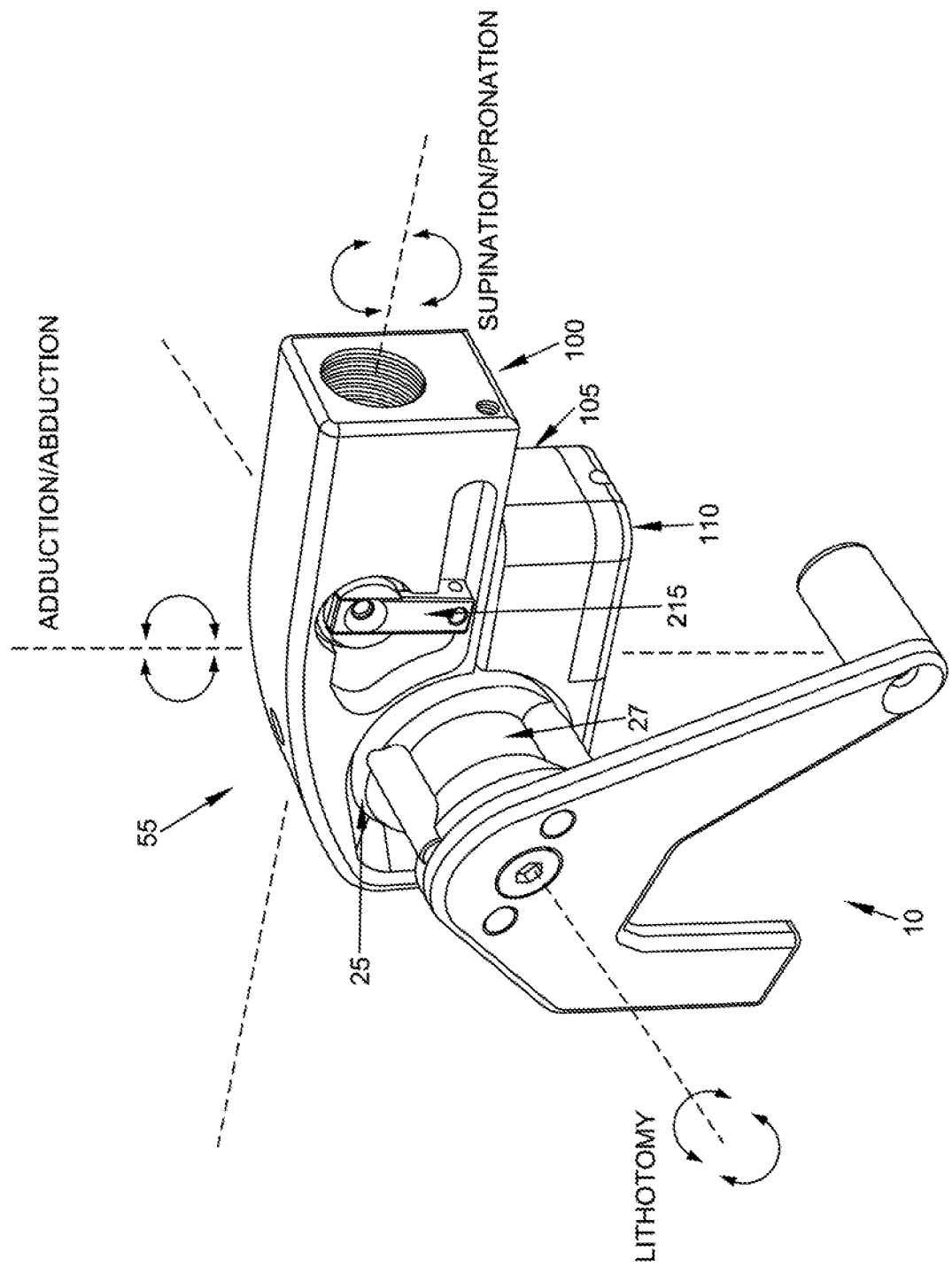
FIG. 24 is a schematic view of the clamping assembly coupled to the mount assembly.
Figure 25:
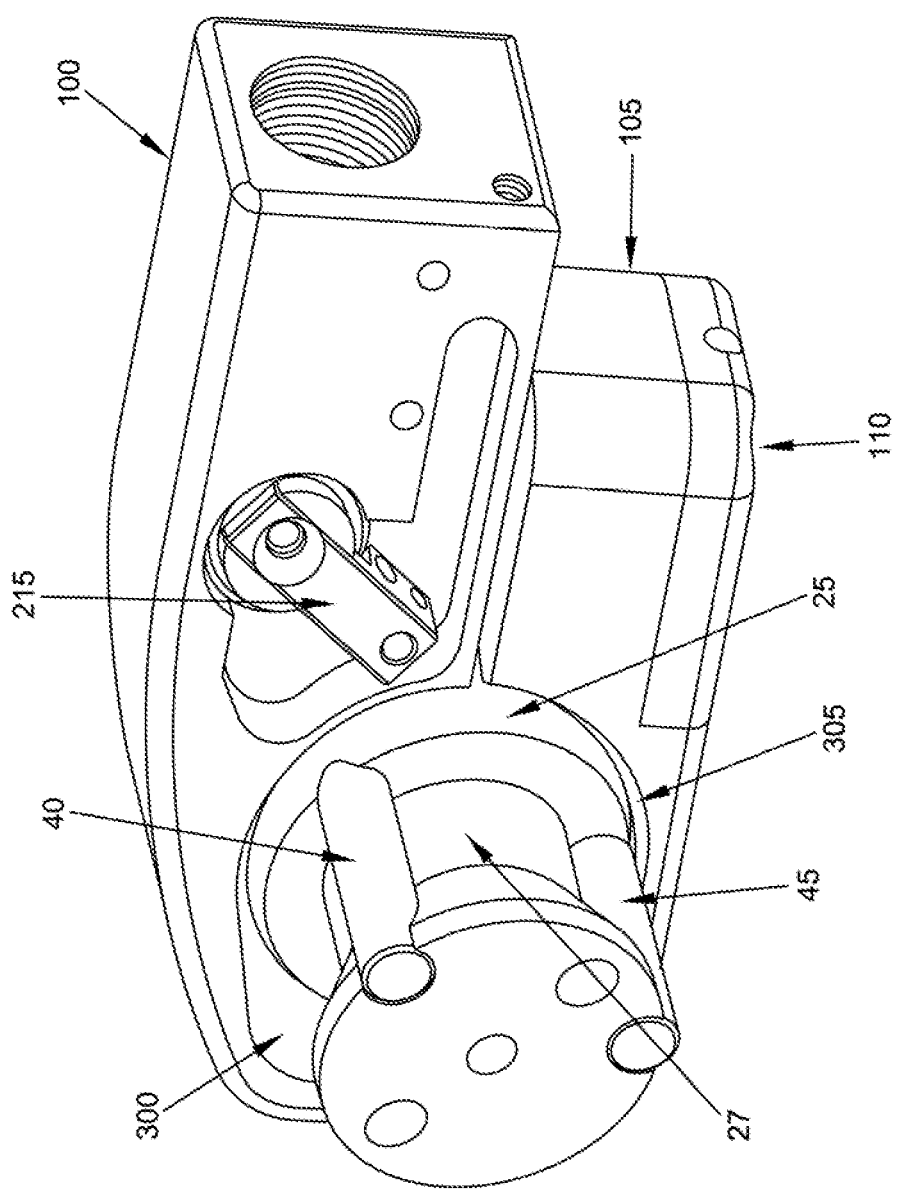
FIG. 25 is another schematic view of the clamping assembly mounted to the semi-ball of the mount assembly.
Figure 26:
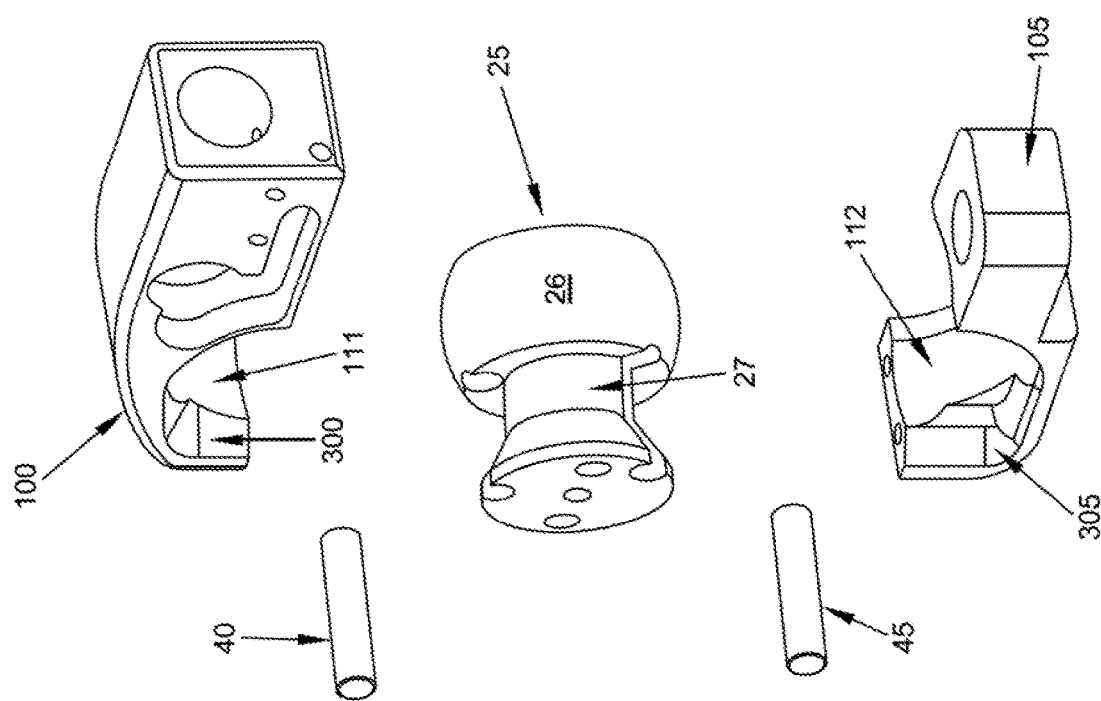
FIGS. 26-28 are schematic views showing further details of various elements shown in FIGS. 24 and 25.
Figure 27:
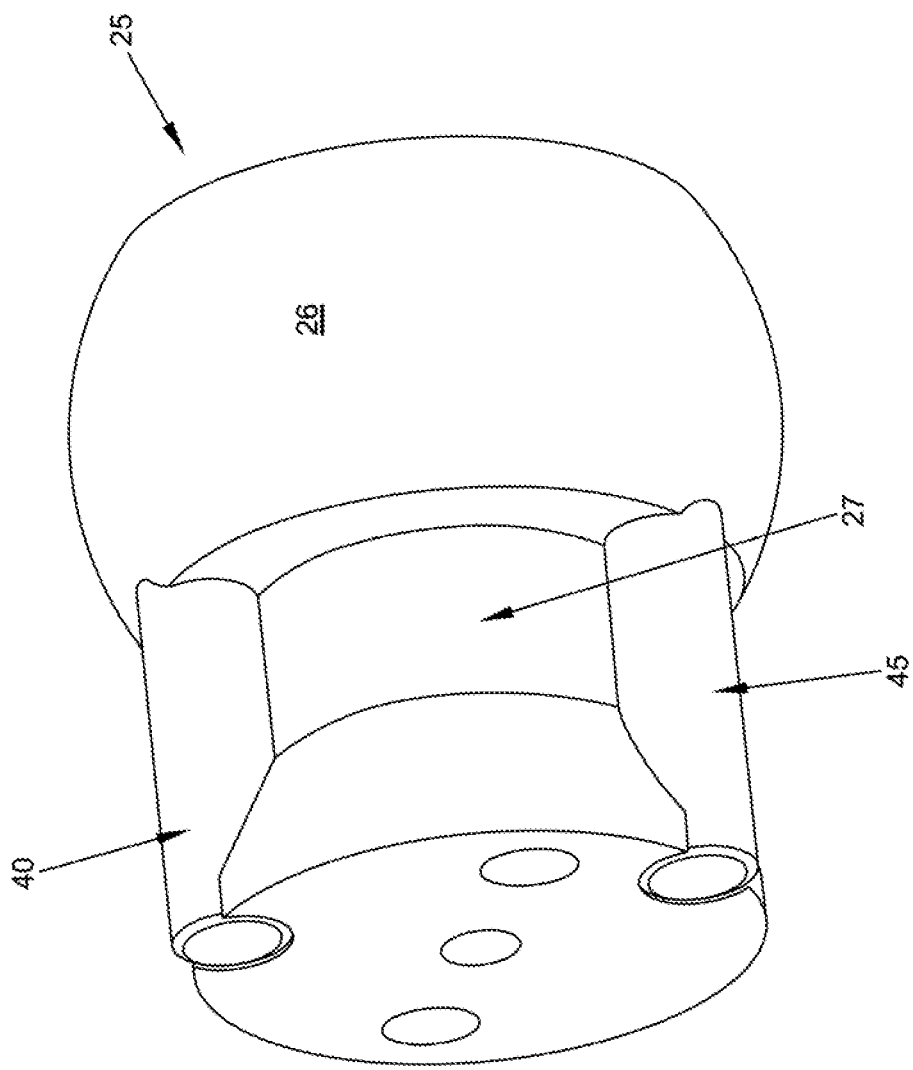
Figure 28:
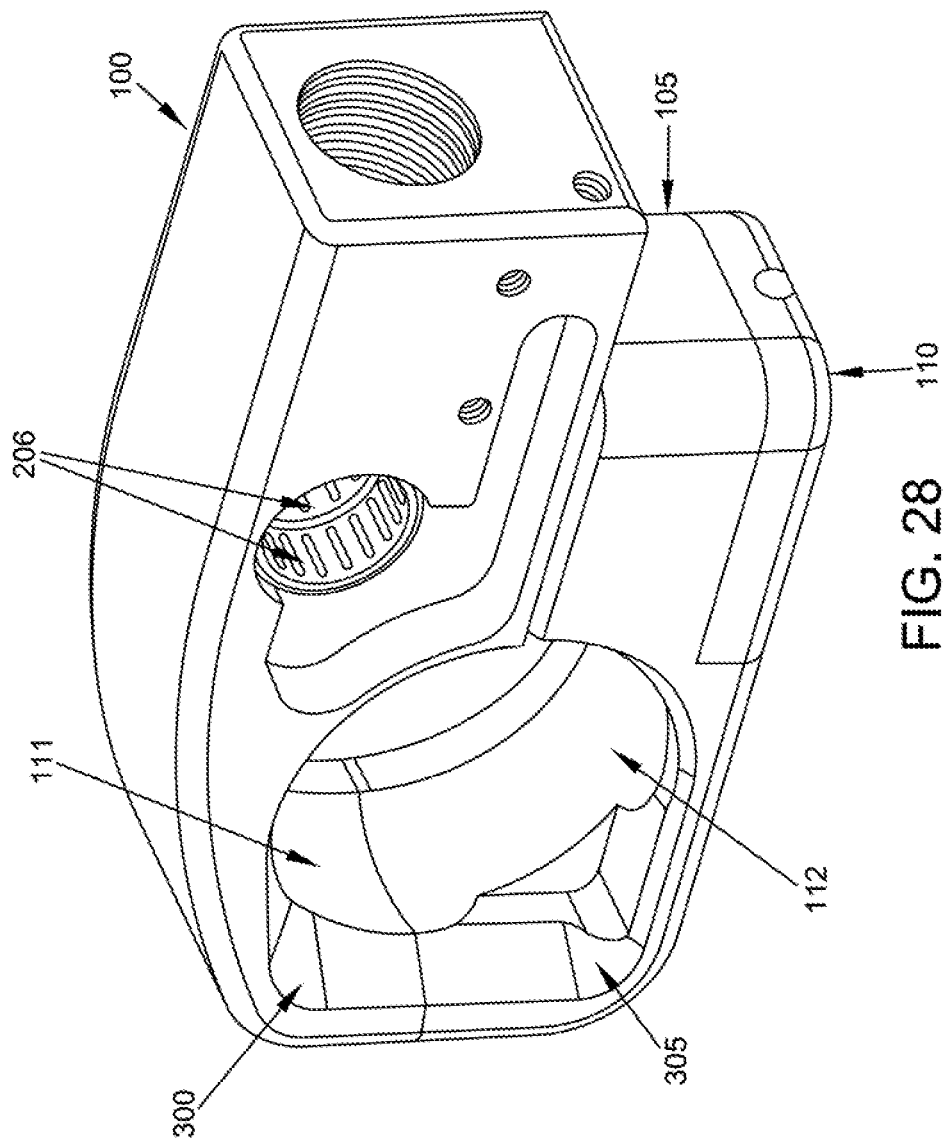
Figure 29:
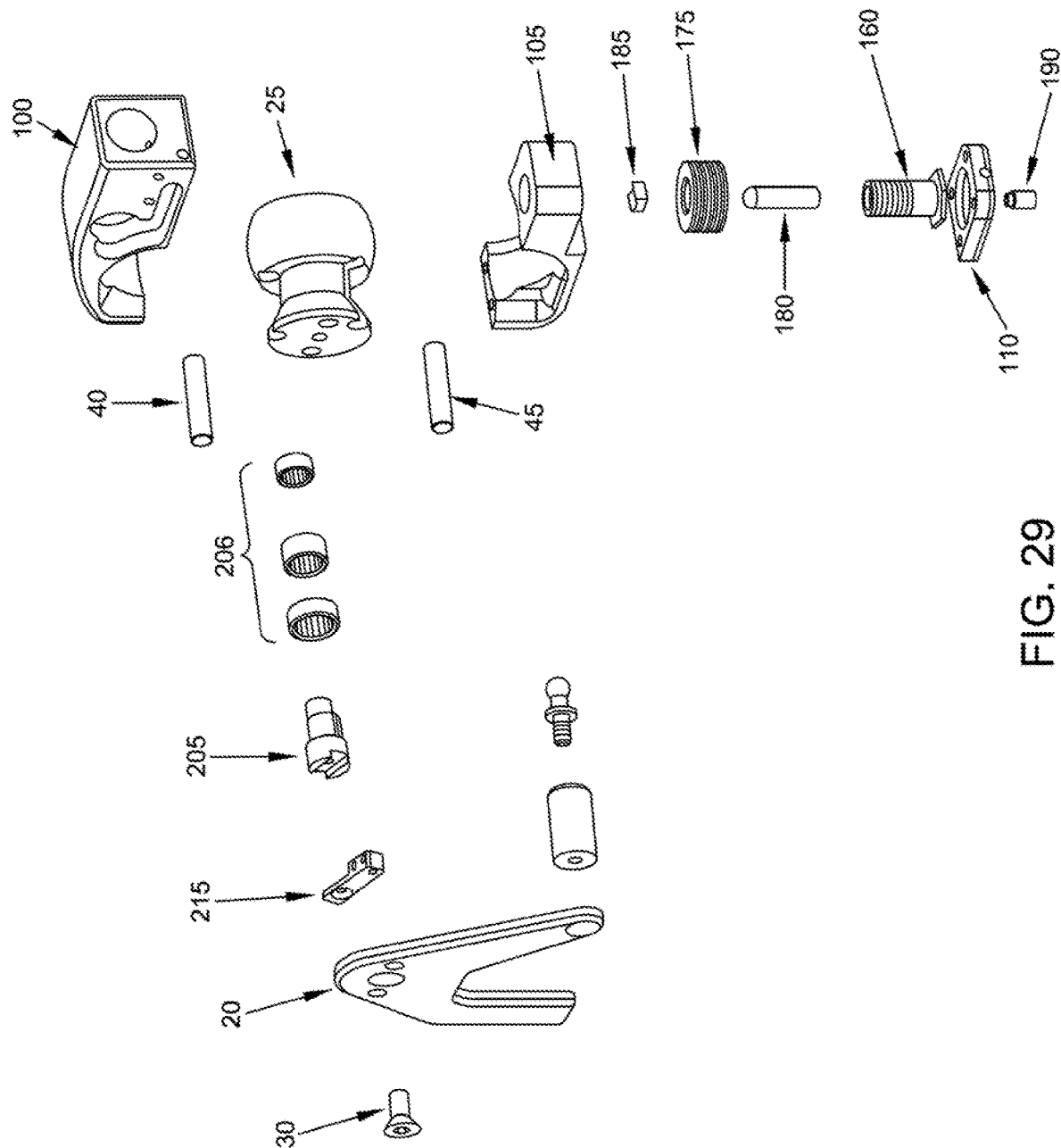
FIG. 29 is an exploded view showing various components of the adjustable leg holder of the present invention.

The "roll", "pitch" and "yaw" movements of clamping assembly 55 about semi-ball 25 correspond to the supination/pronation, lithotomy and abduction/adduction movement of the assembled device (see FIG. 24).

As discussed above, the ability of clamping assembly 55 to rotate about semi-ball 25 is controlled by upper jaw 100 and lower jaw 105 which act as a clamp around the semi-ball.

Normally upper jaw 100 and lower jaw 105 are held in the clamping position about semi-ball 25 by spring element 175 as previously discussed.

It will be understood that any spring configuration of sufficient force will prevent clamping assembly 55 from turning about any of the axes of semi-ball 25. Spring element 175 shown herein is intended to be illustrative and not limiting, and may be altered in many ways without changing the intention of this invention.

Still looking now at FIGS. 24-29, the combined interaction of several elements (i.e., upper limiting pin 40, lower limiting pin 45, upper limit surface 300 on upper jaw 100 and lower limit surface 305 on lower jaw 105) limits and refines the allowed motion of clamp assembly 55 and hence limits and refines the allowed motion of stirrup boot 70 attached to clamp assembly 55.

In a preferred embodiment, engagement of upper limit surface 300 and lower limit surface 305 with upper limiting pin 40 and lower limiting pin 45, respectively, restricts the adduction angle at high lithotomy to 9° and the adduction angle at low lithotomy to 9°.

Also, in a preferred embodiment, the contact of upper limit surface 300 and lower limit surface 305 with neck 27 of semi-ball 25 restricts the abduction angle in all positions to the 25° angle considered to be a maximum abduction angle in lithotomy positioning.

It will be appreciated that this description of the restrictions provided by upper limiting pin 40 and lower limiting pin 45, and upper limit surface 300 and lower limit surface 305, are illustrative of a preferred embodiment only, and that the same or similar elements, with differing dimensions, will produce differing restrictions without changing the sense of the invention.

Thus it will be seen that the present invention provides a stirrup-type leg holder 5, wherein the stirrup-type leg holder comprises a mounting bracket 20 for attachment to a surgical table; a semi-ball 25 for attachment to mounting bracket 20; a clamping assembly 55 comprising an upper jaw 100 and a lower jaw 105 for clamping engagement about semi-ball 25; and a stirrup boot 70 mounted to clamping assembly 55 via support rod 50. A release mechanism is provided to selectively release clamping assembly 55 so as to allow stirrup boot 70 to be repositioned relative to semi-ball 25 (and hence repositioned relative to the surgical table). The release mechanism comprises an actuating mechanism (e.g., a handle 60 and actuating element or lever 65) which controls a cam mechanism 200 which can force upper jaw 100 and lower jaw 105 apart, against the bias of spring element 175, whereby to allow upper jaw 100 and lower jaw 105 to rotate about semi-ball 25, and hence allow the position of stirrup boot 70 to be adjusted relative to the surgical table. In one preferred construction, semi-ball 25 comprises upper limiting pin 40 and lower limiting pin 45 which cooperate with upper limit surface 300 on upper jaw 100 and lower limit surface 305 on lower jaw 105 to limit rotation of the upper and lower jaws about the semi-ball. Gas cylinder 80 is also provided to assist in positioning the leg support assembly 15 relative to the surgical table.

In the foregoing description, mount assembly 10 is described as comprising a mounting bracket 20 and a semi-ball 25, wherein semi-ball 25 comprises an outer surface 26 following a spheroidal geometry, and a neck 27 extending along the longitudinal axis of the semi-ball. However, it should be appreciated that if desired, semi-ball 25 may be replaced by a different mounting element comprising an outer surface 26 following a spheroidal geometry, e.g., a substantially complete sphere, etc. Furthermore, if desired, neck 27 may be omitted and semi-ball 25 (and/or such alternative mounting element, e.g., a substantially complete sphere) may be mounted directly to mounting bracket 20.

It will be appreciated that numerous benefits are obtained by using the novel leg holder 5 of the present invention. First and foremost, the ball-and-socket type connection between mount assembly 10 and leg support assembly 15 allows for a greater range of motion along more axes of rotation, allowing the physician to place a patient's leg in the optimal position for a particular procedure. As a result, the physician is provided with a better operating environment, increasing the likelihood of better patient outcomes.

It should also be appreciated that the novel leg holder 5 may be reconfigured as a limb holder to provide support for different limbs, e.g., it may be reconfigured to provide support for the arms of a patient.

The present invention may also be used in connection with patient supports other than surgical tables, e.g., it may be used with gurneys, hospital beds, chairs, etc., and the present invention may be used for procedures other than surgical procedures, e.g., it may be used for examination procedures, physical therapy, etc.

2. Second Embodiment of the Invention

In the foregoing disclosure there is disclosed a novel sirrup-type leg holder 5 which can be mounted to a surgical table by means of a ball-and-socket arrangement, wherein the "ball" (i.e., semi-ball 25) is fixedly mounted to the surgical table and the "socket" (i.e., clamping assembly 55) is fixedly mounted to the proximal end of the leg support assembly 15, such that the leg support assembly can be moved along at least three (3) axes of rotation relative to the surgical table.

In an additional construction, and as will hereinafter be discussed, the "socket" can be fixedly mounted to the surgical table and the "ball" can be fixedly mounted to the proximal end of the leg support assembly of the leg holder.

More particularly, and looking now at FIGS. 30-33, there is shown a novel stirrup-type leg holder 405 (FIG. 30) formed in accordance with the present invention. Leg holder 405 is constructed so that it may be easily mounted to a surgical table and thereafter easily adjusted at the distal end of the leg stirrup in order to alter the position of the leg of a patient. More particularly, leg holder 405 generally comprises a mount assembly 410 (FIG. 30) for mounting leg holder 405 to a surgical table, and a leg support assembly 415 (FIG. 30) for supporting a patient's leg. Leg support assembly 415 is adjustably mounted to mount assembly 410 by a ball-and-socket arrangement as will hereinafter be discussed. As a result of this construction, a physician is able to move leg support assembly 415 along at least three (3) axes of rotation relative to mount assembly 410 (and hence relative to the surgical table). Consequently, in use, a physician is also able to move a patient's leg that is supported by leg support assembly 415 along at least three (3) axes of rotation relative to the surgical table.

2A. Mount Assembly

Figure 34:
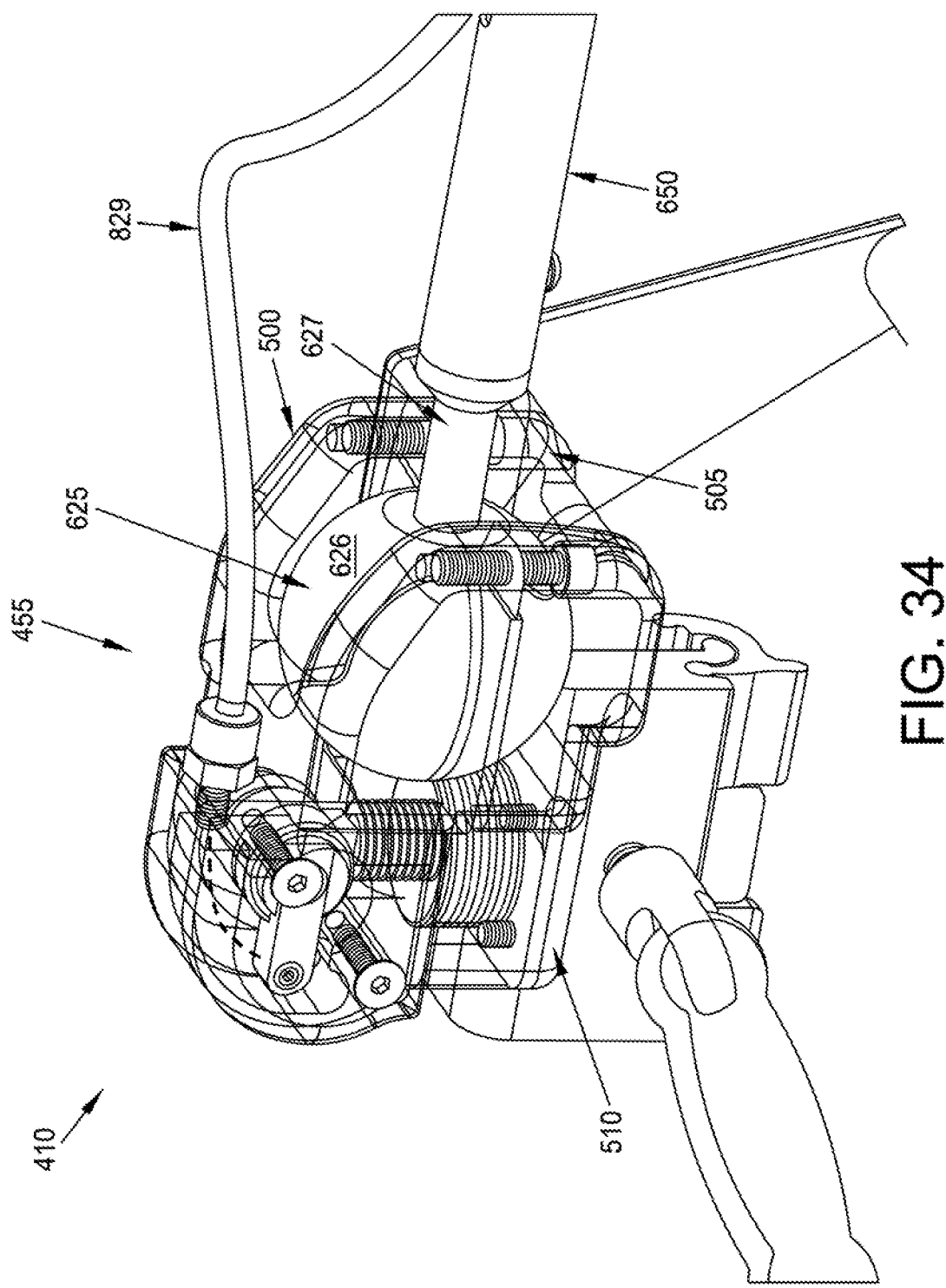
FIG. 34 is a schematic view of the mount assembly and the proximal end of the leg support assembly of the adjustable leg holder shown in FIG. 30.
Figure 35:
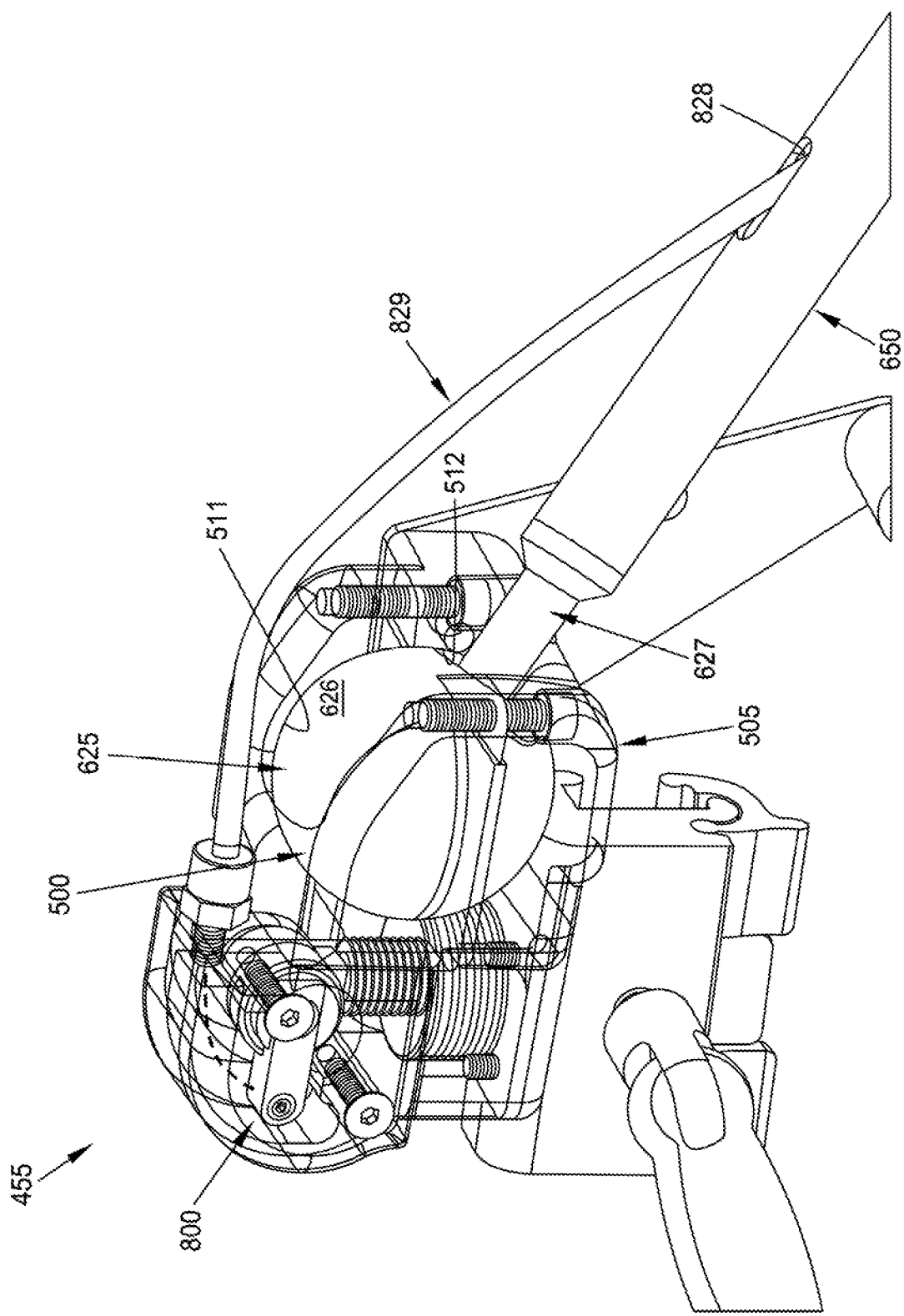
FIG. 35 is another schematic view of the mount assembly and the proximal end of the leg support assembly of the adjustable leg holder shown in FIG. 30.
Figure 36:
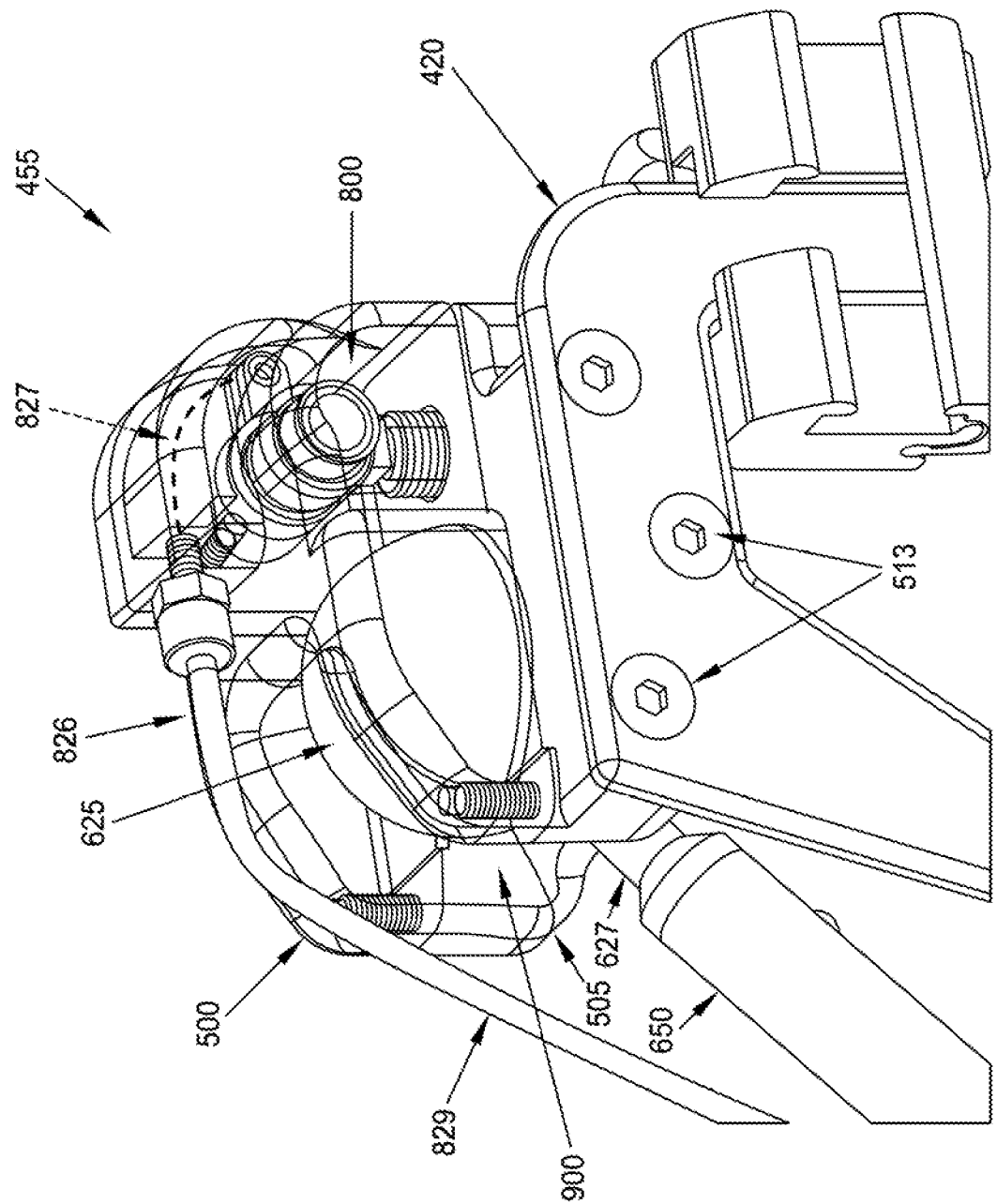
FIG. 36 is another schematic view of the mount assembly and the proximal end of the leg support assembly of the adjustable leg holder shown in FIG. 30.

In one preferred embodiment of the invention, and looking now at FIGS. 34-40, mount assembly 410 comprises a mounting bracket 420 (FIG. 36) and a clamping assembly 455 (FIG. 34) which is secured to mounting bracket 420. Clamping assembly 455 comprises an upper jaw 500 (FIG. 34), a lower jaw 505 (FIG. 34) and a bottom plate 510 (FIG. 34). Lower jaw 505 is secured to mounting bracket 420, e.g., by means of screws 513 (FIG. 36). Upper jaw 500 comprises a concave gripping surface 511 (FIG. 35) for engaging the spheroidal outer surface of a semi-ball, and lower jaw 505 comprises a concave gripping surface 512 (FIG. 35) for engaging the spheroidal outer surface 626 (FIG. 34) of a semi-ball as will hereinafter be discussed in greater detail. Upper jaw 500 and lower jaw 505 are cut away so as to provide a recess 900 (FIGS. 30 and 36) which accommodates the portion of leg support assembly 415 just distal to the semi-ball, whereby to allow leg support assembly 415 to articulate relative to clamping assembly 455. Note that recess 900 can be configured to selectively limit articulation of leg support assembly 415 relative to clamping assembly 455, as will hereinafter be discussed in greater detail. A bore 515 (FIG. 37) and a counter bore 516 (FIG. 37) extend through lower jaw 505. Bore 515 is of a first diameter near the top surface 520 (FIG. 37) of lower jaw 505 and counterbore 516 is of a second, larger diameter deep to top surface 520 of lower jaw 505. An annular shoulder 517 (FIG. 37) is disposed at the intersection of bore 515 and counterbore 516.

A cavity 525 (FIG. 37) that is coaxial with bore 515 and counterbore 516 extends into upper jaw 500 from the bottom surface 530 (FIG. 37) of upper jaw 500. A portion of cavity 525 is threaded so as to threadably engage the shaft of a spring compression bolt (see below).

Figure 42:
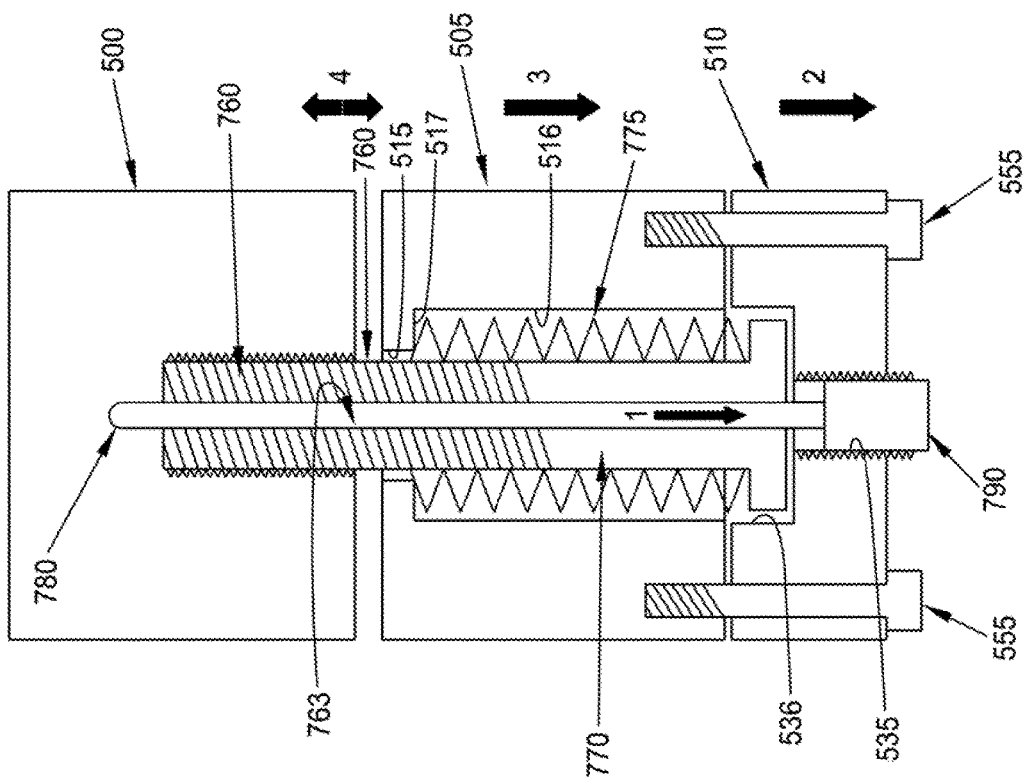
FIG. 42 is a simplified schematic view of selected components of the clamping assembly of the mount assembly of the adjustable leg holder shown in FIG. 30, showing the forces which act on the various components of the clamping assembly.
Figure 43:
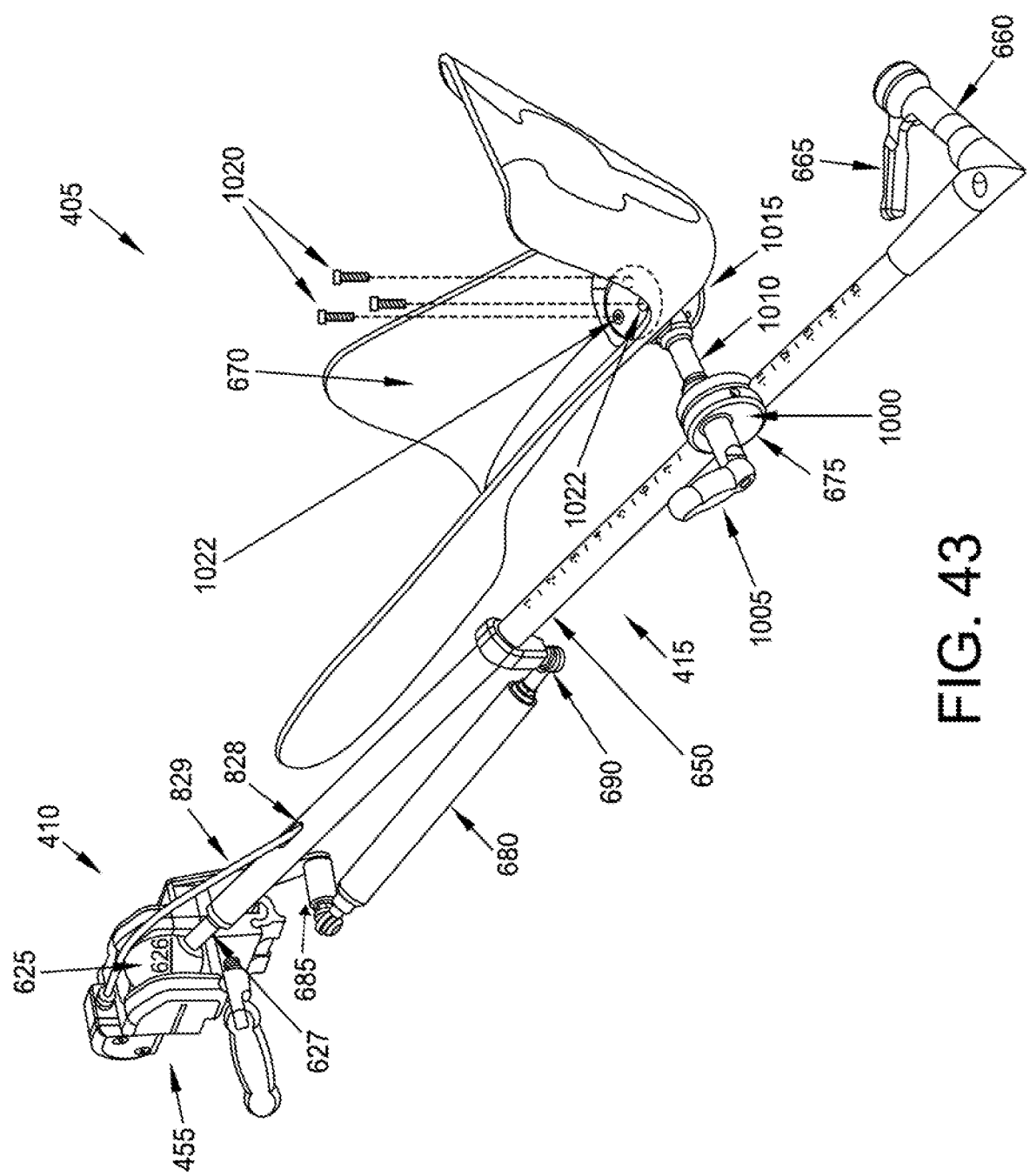
FIGS. 43-46 are schematic views of the adjustable leg holder shown in FIG. 30, showing how the boot is mounted to the adjustable leg holder.
Figure 44:
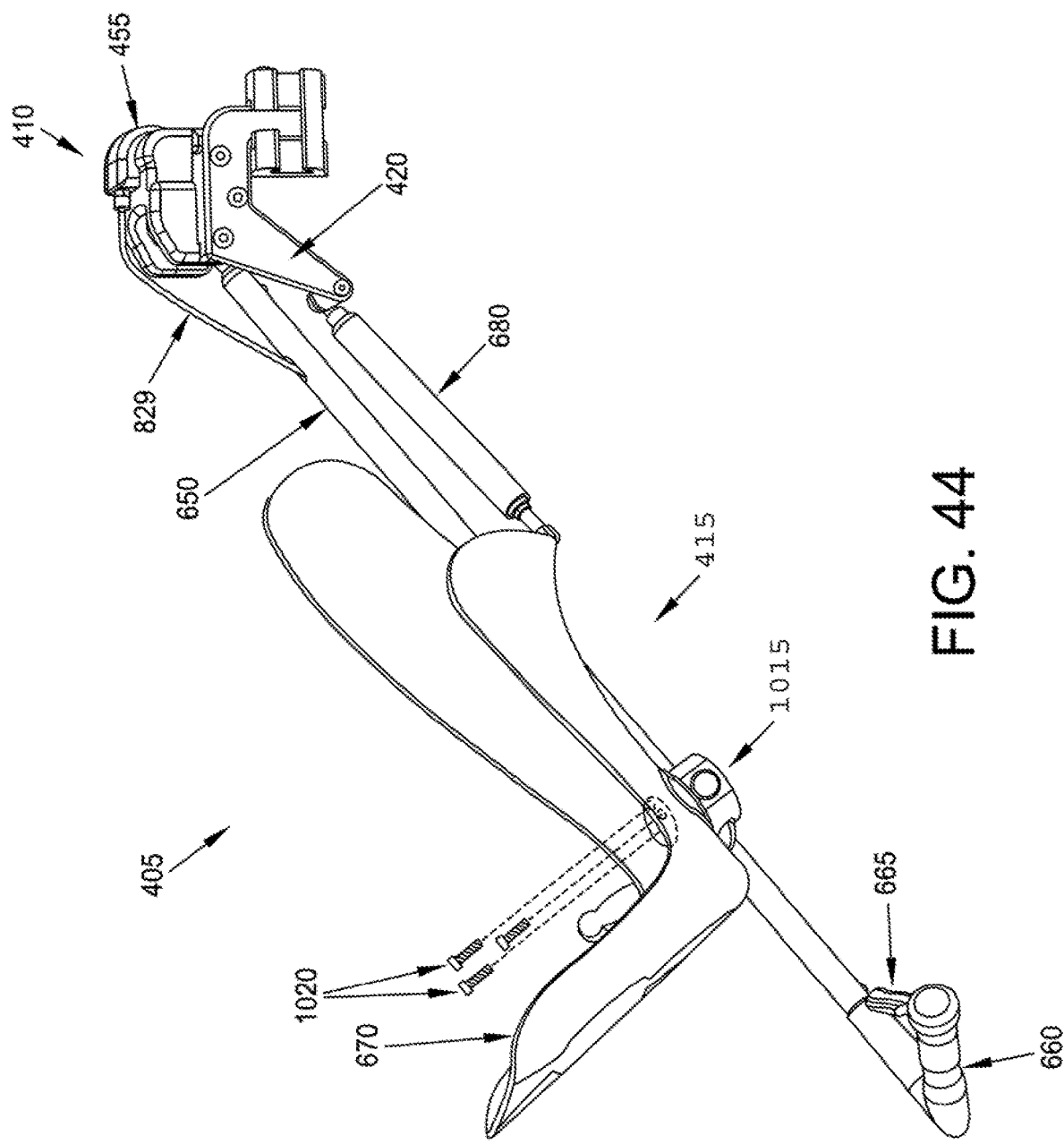
Figure 45:
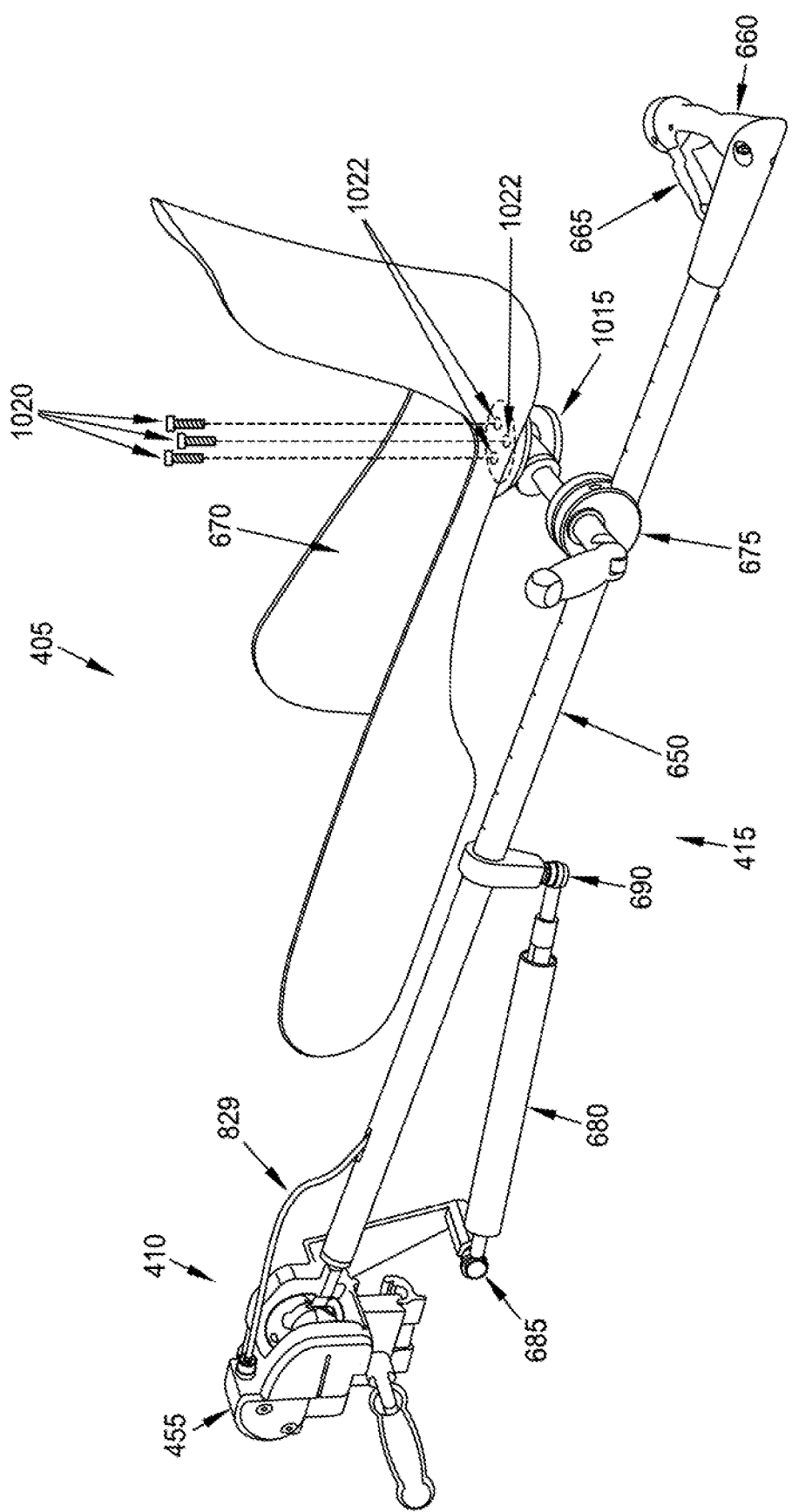
Figure 46:
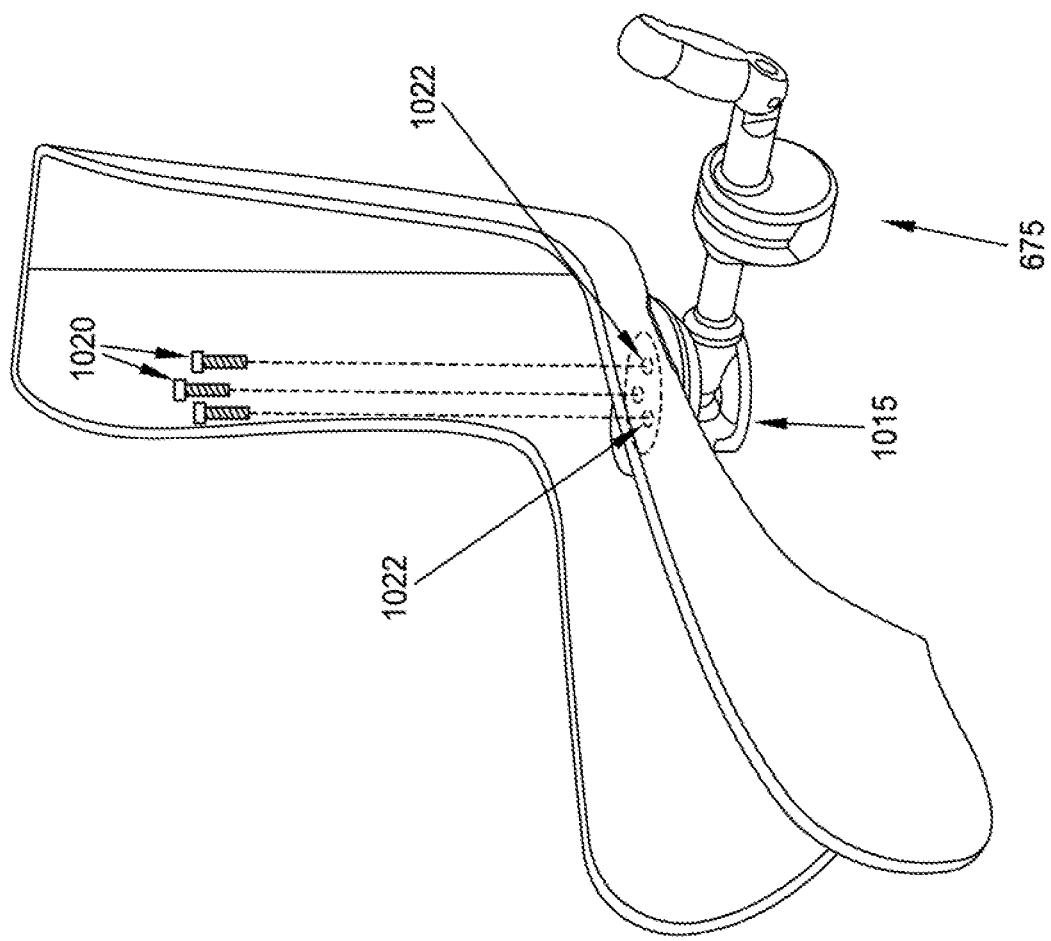
Figure 47:
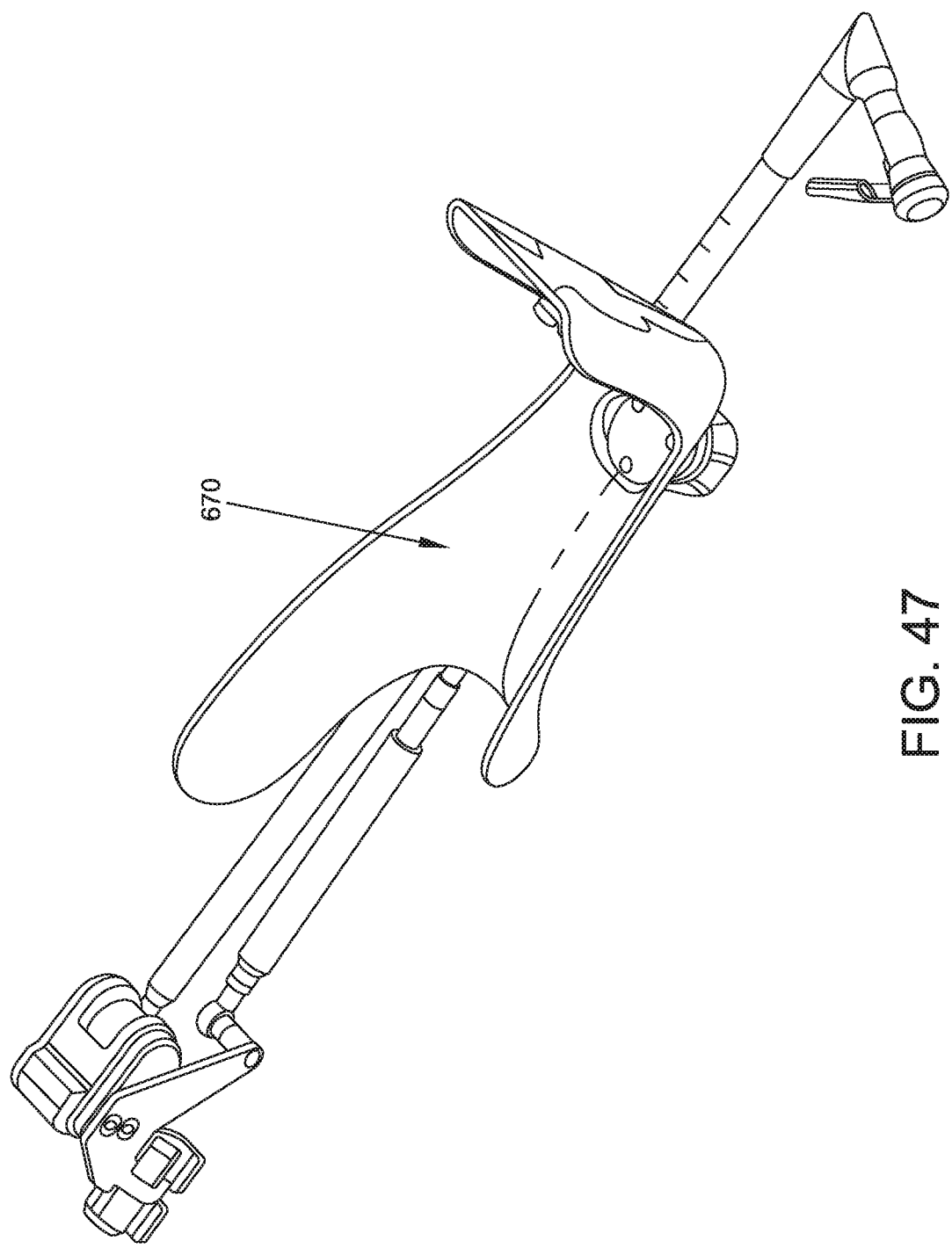
Figure 48:
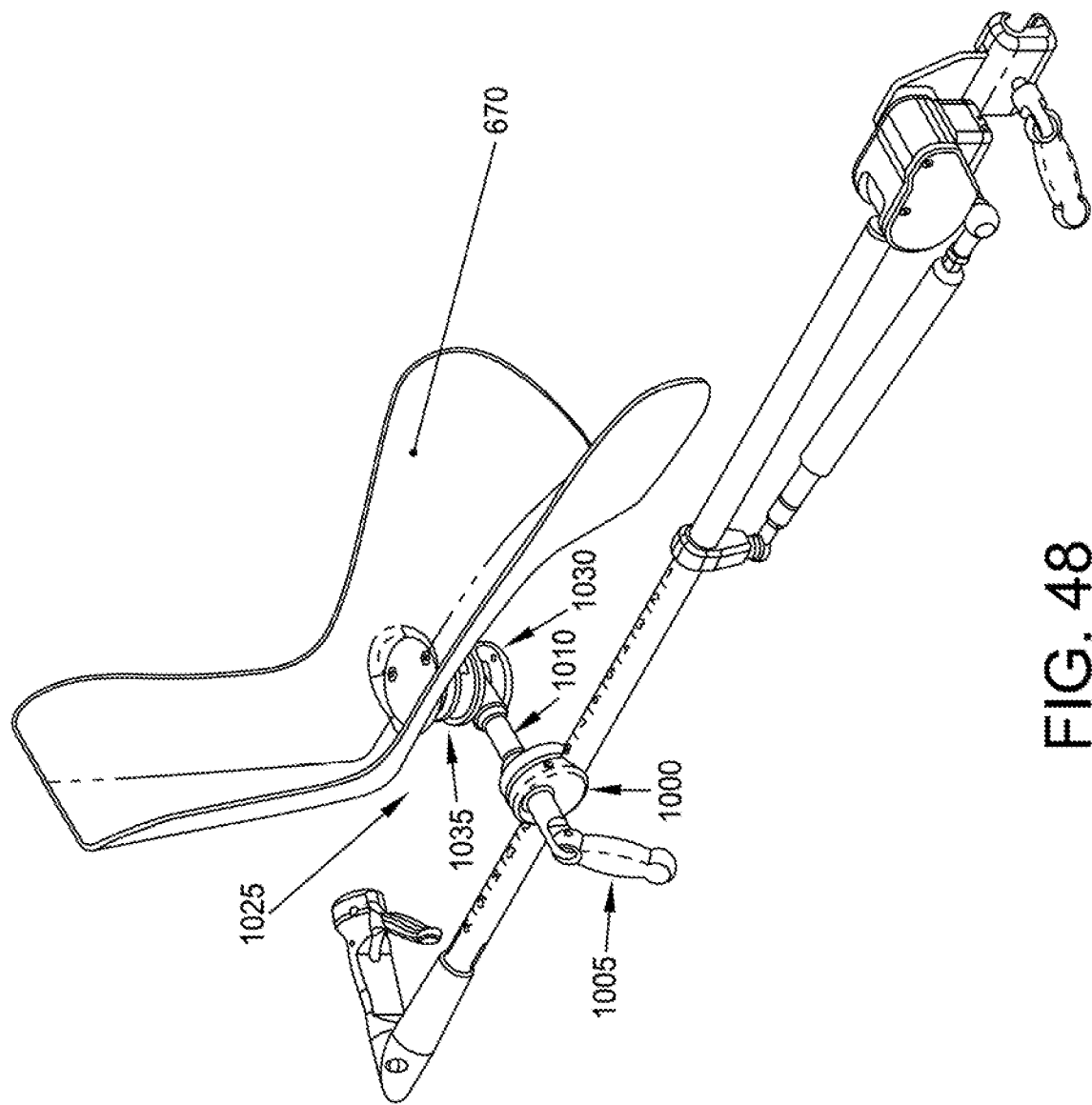
Figure 49:
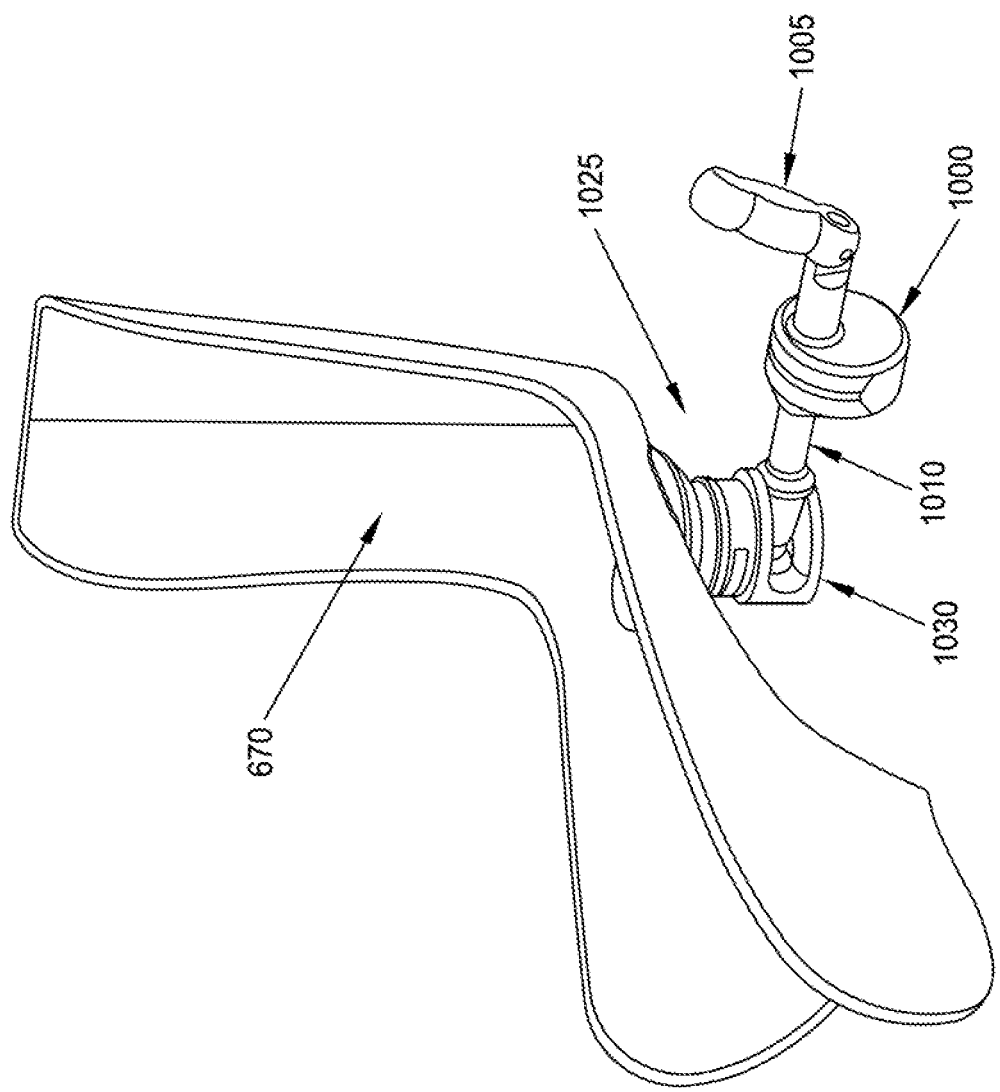
Figure 50:
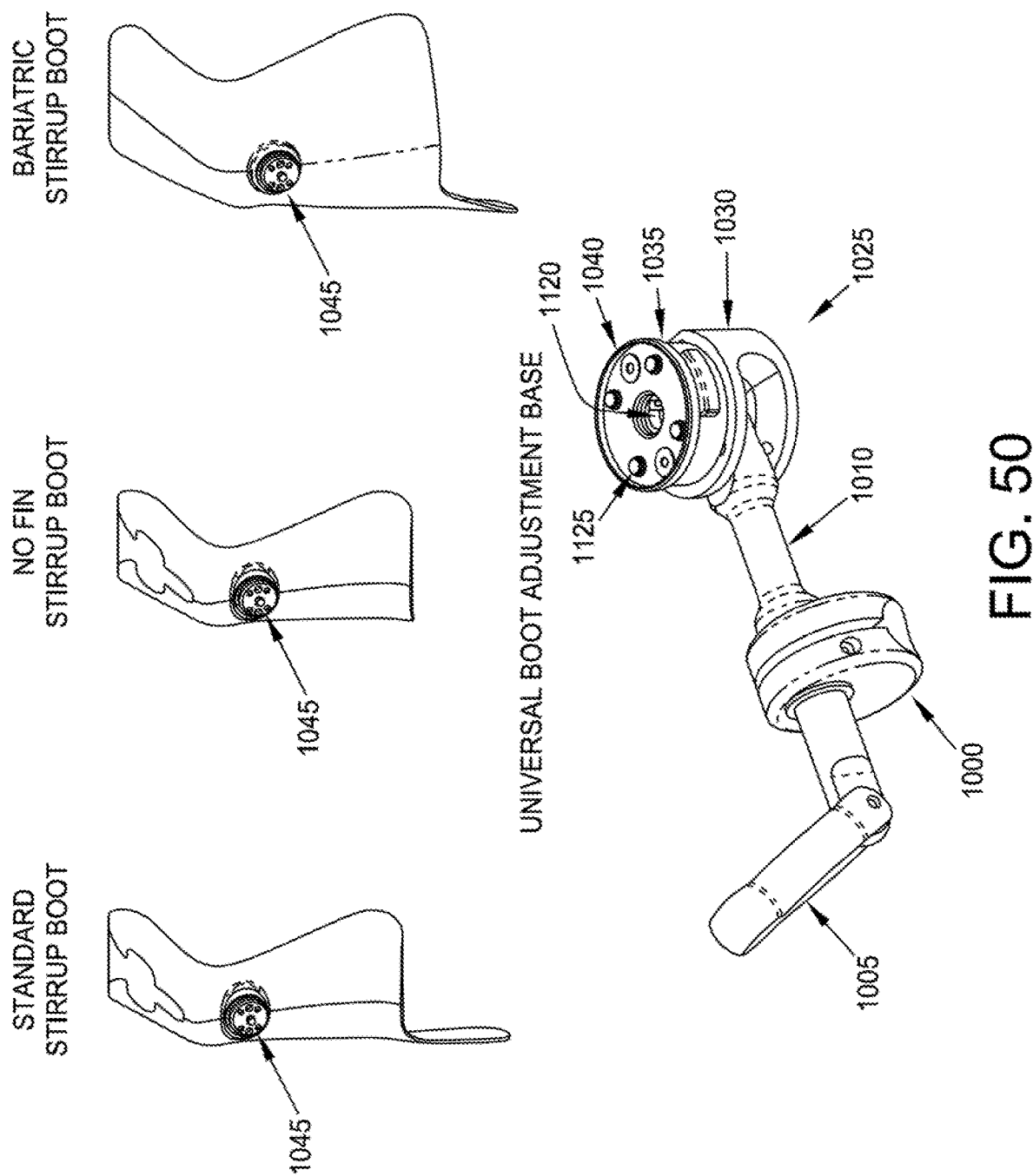
Figure 51:
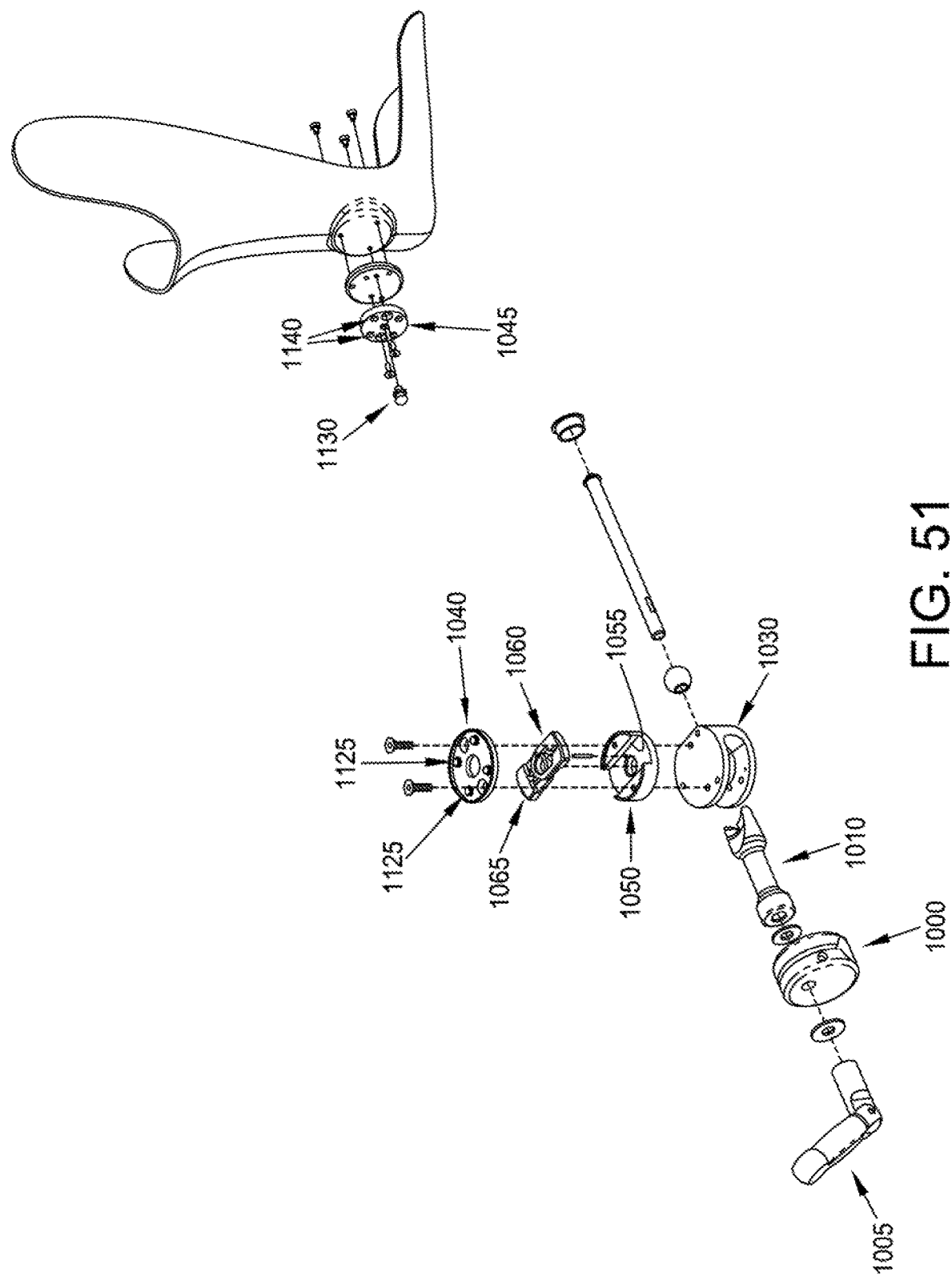

A bore 535 (FIG. 42) and counterbore 536 (FIG. 42) extend through bottom plate 510 (see FIG. 42). Bore 535 is of a first diameter from bottom surface 540 (FIG. 37) of bottom plate 510 until just below top surface 545 (FIG. 37) of bottom plate 510, and counterbore 536 is of a second, larger diameter. Bore 535 is threaded to engage a tension set screw (see below).

Figure 37:
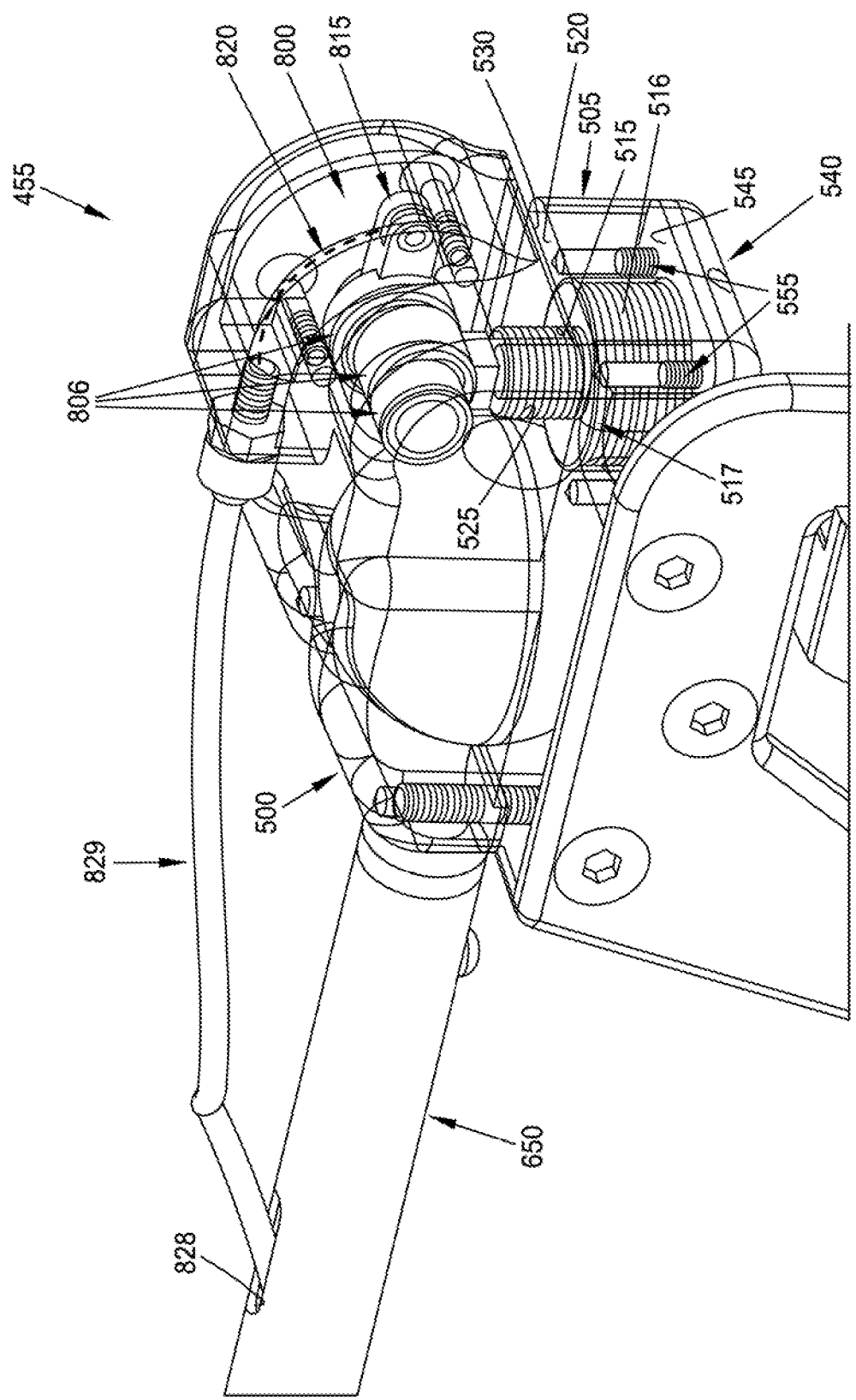
FIG. 37 is another schematic view of the mount assembly and the proximal end of the leg support assembly of the adjustable leg holder shown in FIG. 30.
Figure 38:
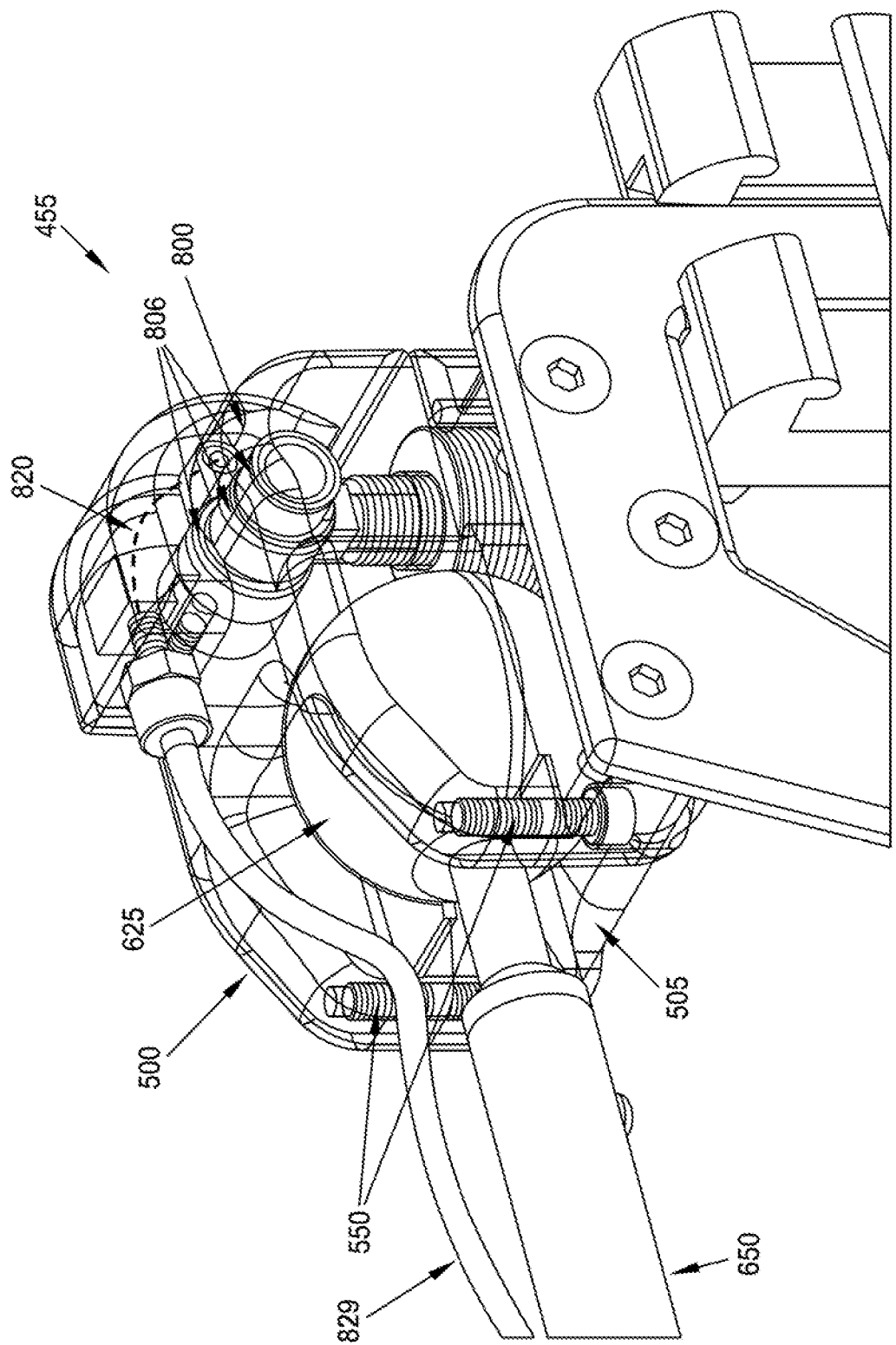
FIG. 38 is another schematic view of the mount assembly and the proximal end of the leg support assembly of the adjustable leg holder shown in FIG. 30.
Figure 39:
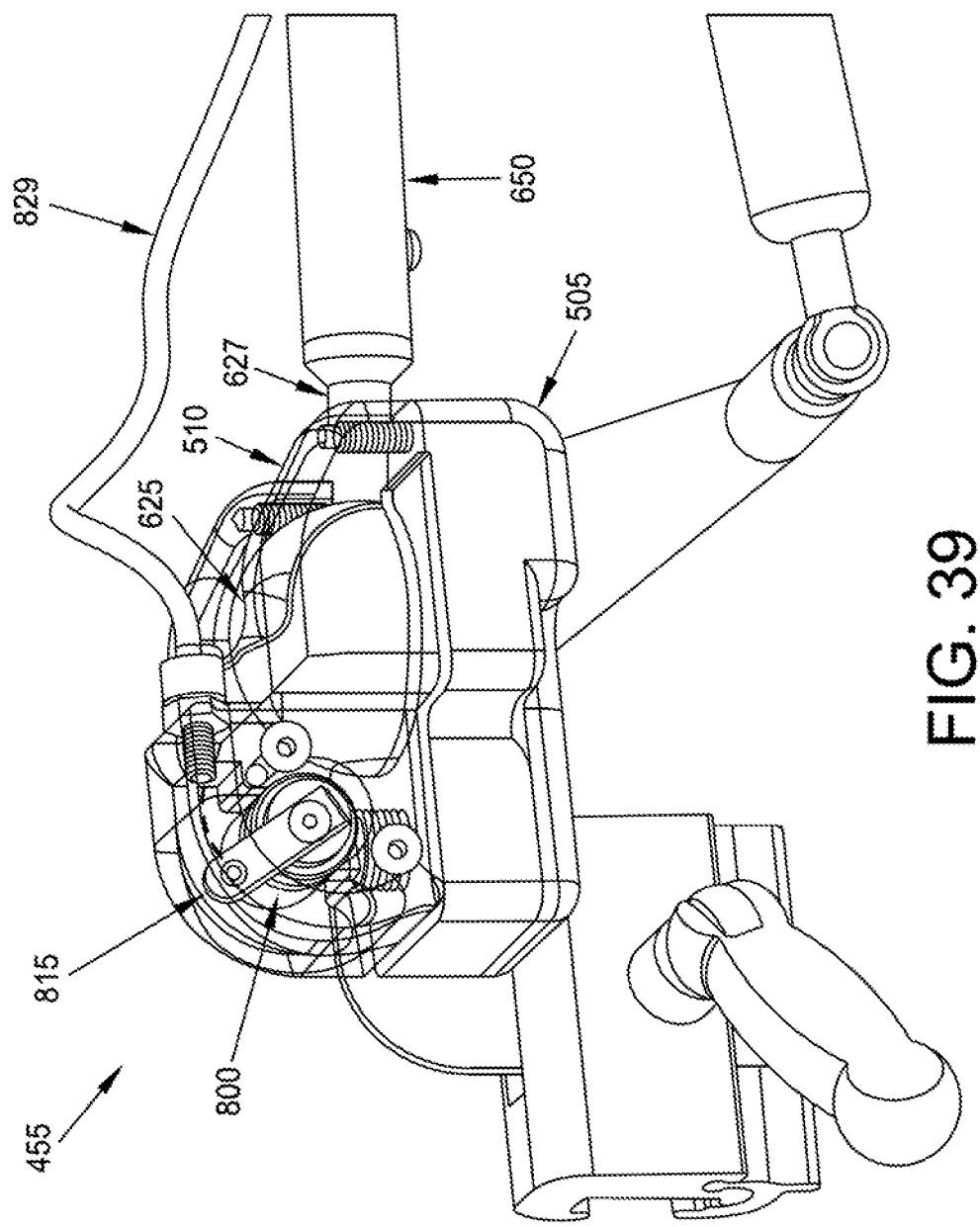
FIG. 39 is another schematic view of the mount assembly and the proximal end of the leg support assembly of the adjustable leg holder shown in FIG. 30.
Figure 40:
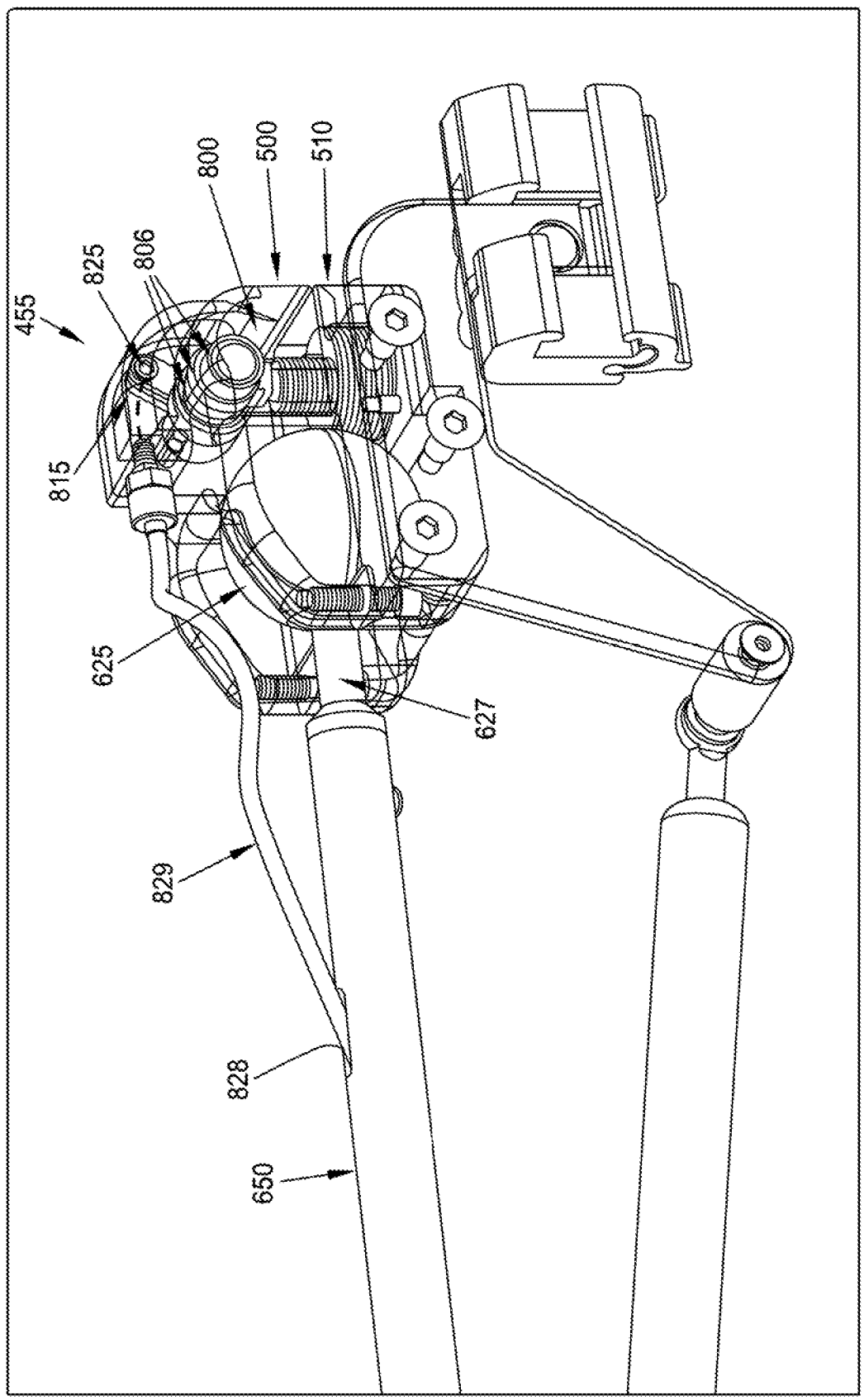
FIG. 40 is another schematic view of the mount assembly and the proximal end of the leg support assembly of the adjustable leg holder shown in FIG. 30.

Upper jaw 500 and lower jaw 505 are joined together at one side of clamping assembly 455 by screws 550 (FIG. 38). Lower plate 510 is joined to lower jaw 505 by screws 555 (FIG. 37).

2B. Leg Support Assembly

Turning now to FIGS. 30-33, leg support assembly 415 generally comprises a support rod 650 (FIG. 30) having a proximal end and a distal end, a semi-ball 625 (FIG. 30) mounted to the proximal end of support rod 650, and a handle 660 (FIG. 30) and an actuating element or lever 665 (FIG. 30) mounted to the distal end of support rod 650. Semi-ball 625 comprises an outer surface 626 (FIG. 30) following a spheroidal geometry, and a neck 627 (FIG. 30) extending along the longitudinal axis of the semi-ball. Semi-ball 625 is fixedly attached to the proximal end of support rod 650 (e.g., by a bolt which extends into neck 627).

Leg support assembly 415 also comprises a stirrup boot 670 (FIG. 30) for receiving the lower leg and foot of a patient. Boot 670 may be mounted on slidable adjuster 675 (FIG. 30), which is itself slidably mounted on support rod 650 intermediate its proximal and distal ends. Slidable adjuster 675 allows boot 670 to be moved along the length of support rod 650 so as to accommodate the anatomy of differently-sized patients.

Figure 30:
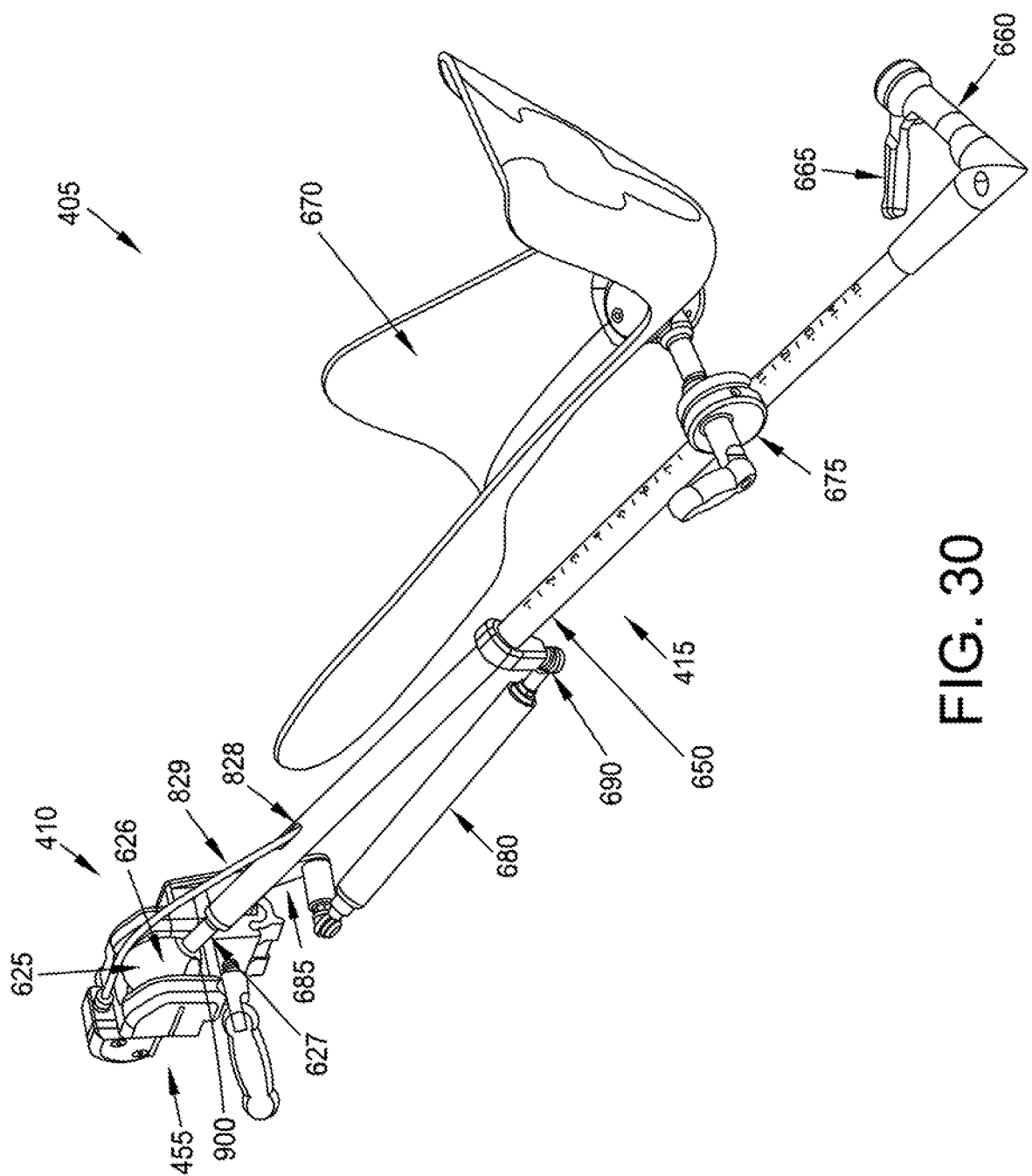
FIG. 30 is a schematic view of another adjustable leg holder formed in accordance with the present invention.
Figure 31:
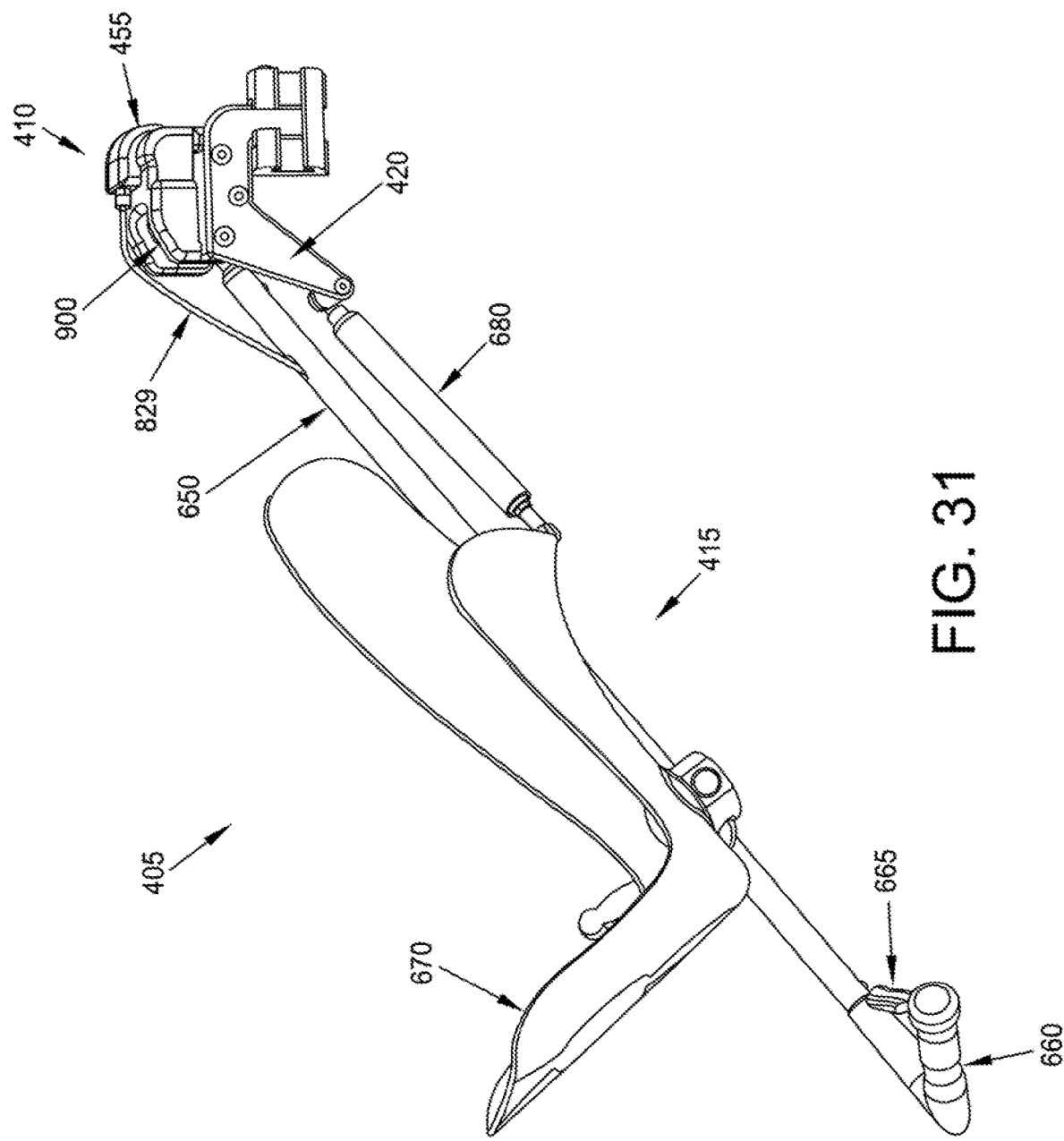
FIG. 31 is another schematic view of the adjustable leg holder shown in FIG. 30.
Figure 32:
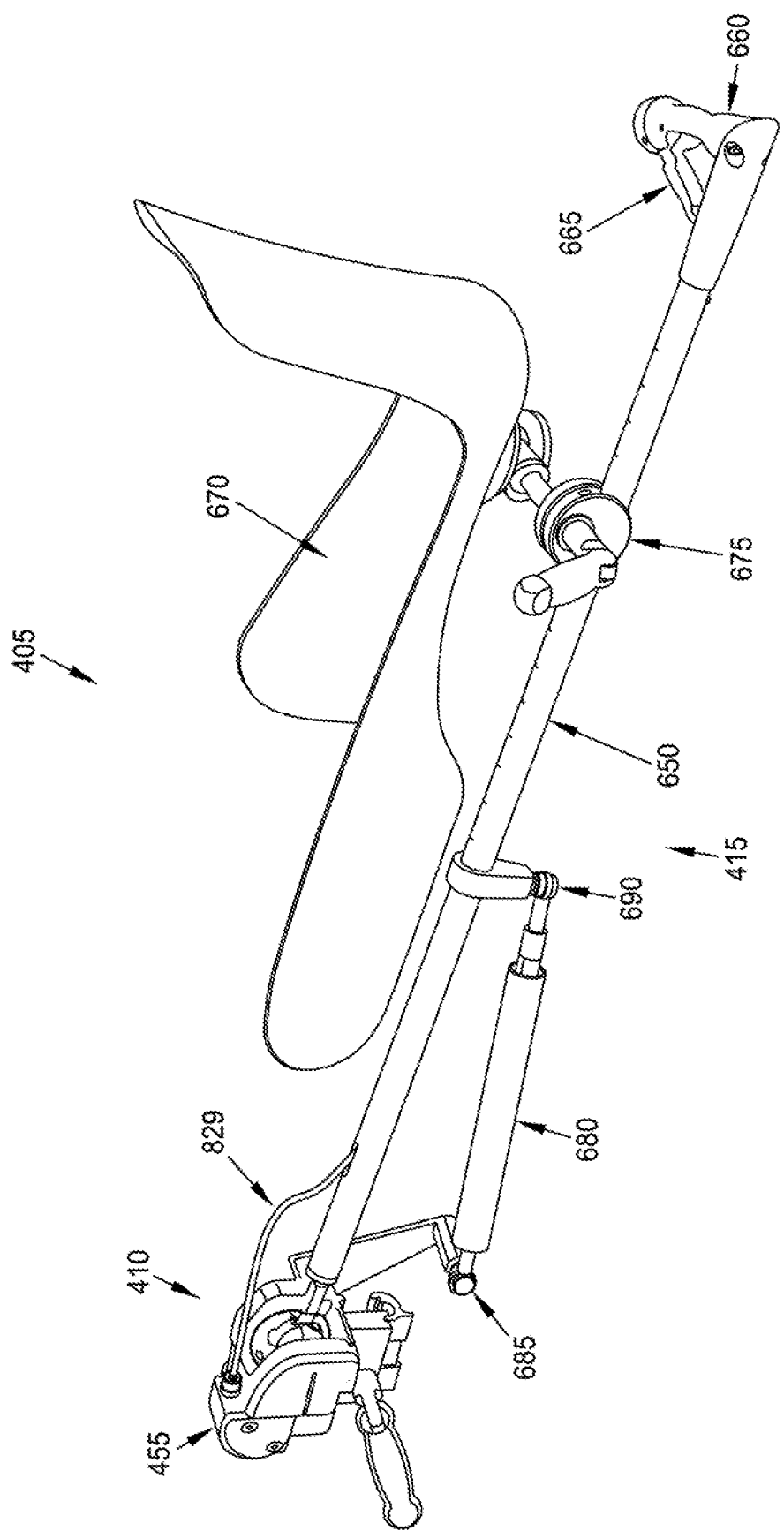
FIG. 32 is another schematic view of the adjustable leg holder shown in FIG. 30.
Figure 33:
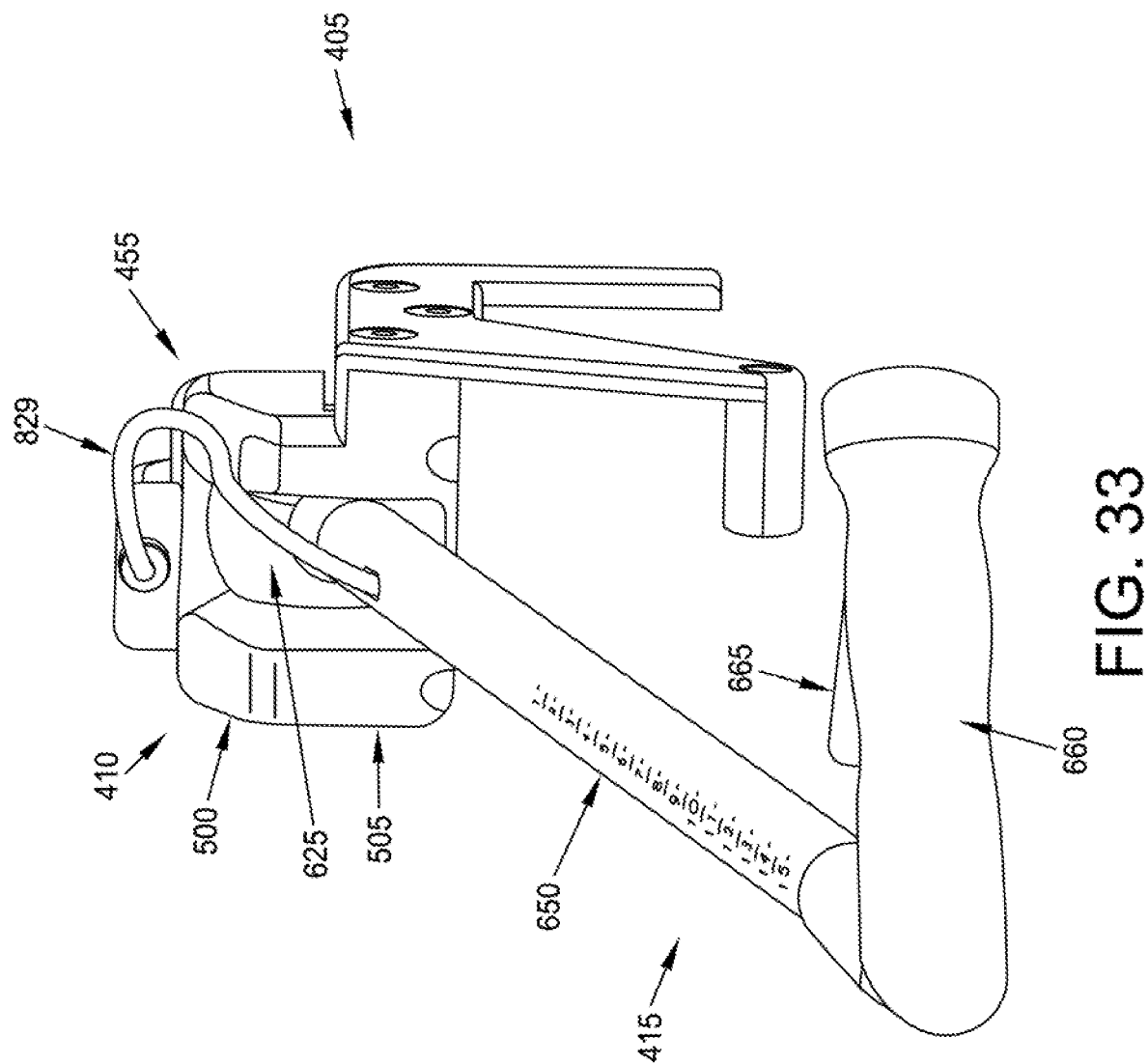
FIG. 33 is another schematic view of the adjustable leg holder shown in FIG. 30.

Leg support assembly 415 preferably also comprises a gas cylinder 680 (FIG. 30). The proximal end of gas cylinder 680 is mounted to distal leg 685 (FIG. 30) of mounting bracket 420 and the distal end of gas cylinder 680 is mounted to a collar 690 (FIG. 30) which is fixedly mounted to support rod 650. The air pressure inside gas cylinder 680 is preferably set so as to approximately offset the combined weight of leg support assembly 415 and a patient's leg so as to render movement of the apparatus relatively easy during use. In the present device, gas cylinder 680 may also be used to limit the travel in the lithotomy dimension, in the sense that clamping assembly 455 can move in the high lithotomy direction until gas cylinder 680 reaches its full extension length and clamping assembly 455 can move in the low lithotomy dimension until it reaches its full compression length. Accordingly, the force exerted by gas cylinder 680 allows a physician to easily move leg support assembly 415 (with a patient's leg disposed thereon) with one hand during use.

2C. Clamping Element

Figure 41:
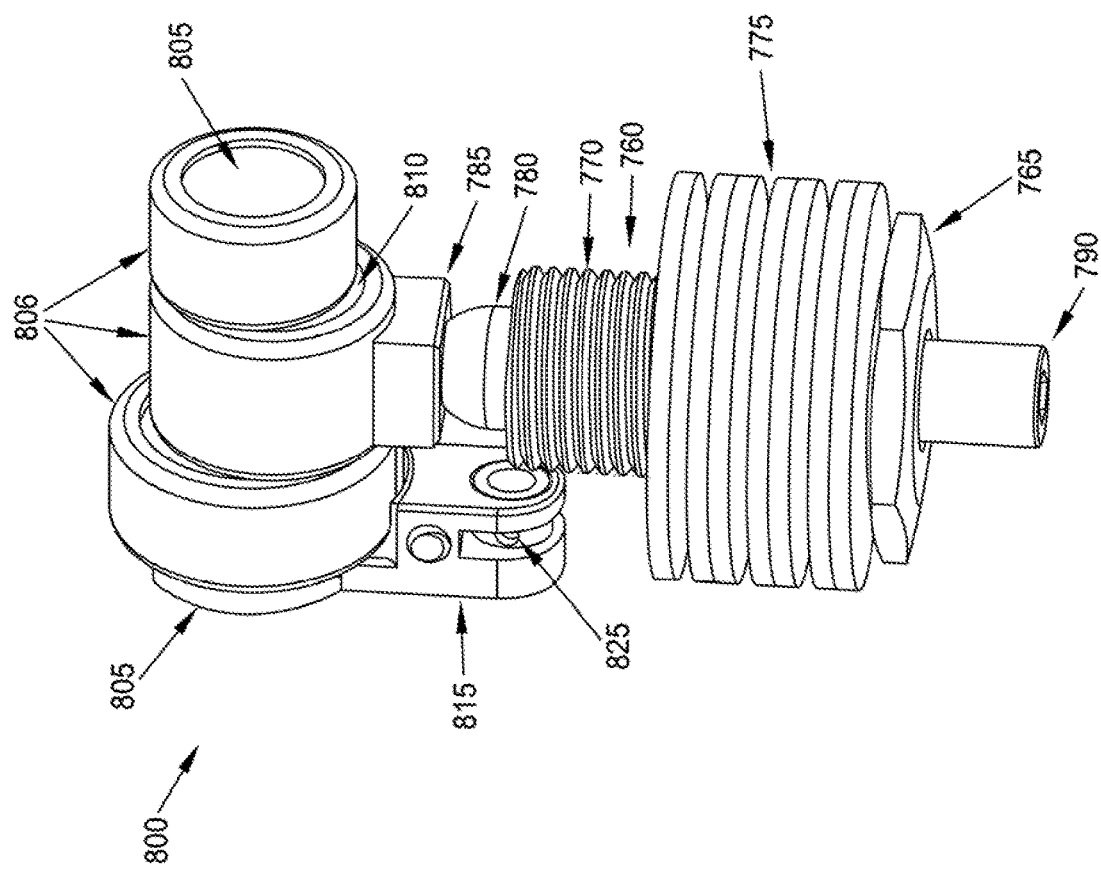
FIG. 41 is a schematic view of the cam mechanism and other selected internal components of the clamping assembly of the mount assembly of the adjustable leg holder shown in FIG. 30.

Turning now to FIGS. 41 and 42, there is shown a spring compression bolt 760 (FIG. 41) having a head 765 (FIG. 41) and a shaft 770 (FIG. 41). Spring compression bolt 760 passes through bore 515 and counterbore 516 of lower jaw 505. A portion of shaft 770 is threaded. Spring compression bolt 760 is configured with a central bore 763 (FIG. 42) extending therethrough. Shaft 770 of spring compression bolt 760 is threadably engaged in cavity 525 of upper jaw 500, whereby to secure spring compression bolt 760 to upper jaw 500. Head 765 of spring compression bolt 760 partially resides in counterbore 516 of lower jaw 505 and in counterbore 536 of bottom plate 510.

Counterbore 516 in lower jaw 505 is sized to accommodate spring element 775 (FIG. 41), which is arranged concentrically around shaft 770 of spring compression bolt 760. Spring element 775 is captured in counterbore 516 in lower jaw 505, between head 765 of spring compression bolt 760 and annular shoulder 517 created where counterbore 516 meets bore 515. See FIG. 42.

On account of the foregoing construction, spring element 775 normally biases head 765 of spring compression bolt 760 away from top surface 520 of lower jaw 505; inasmuch as the opposite threaded end of spring compression bolt 760 is secured to upper jaw 500, this action normally draws upper jaw 500 and lower jaw 505 together, whereby to draw the concave gripping surface 511 of upper jaw 500 and the concave gripping surface 512 of lower jaw 505 onto spheroidal outer surface 626 of semi-ball 625. In this way, clamping assembly 455 is spring-biased so that it normally grips semi-ball 625.

Spring release pin 780 (FIG. 41) extends through central bore 763 of spring compression bolt 760. The top end of spring release pin 780 stands proud of spring compression bolt 760. The top end of spring release pin 780 may have a hemispherical shape configured to mate with the bottom surface of a cam bearing block 785 (FIG. 41) (see below) which may have a complementary hemispherical cavity. Spring release pin 780 terminates in the bottom end of shaft 770 of spring compression bolt 760 just above head 765 of spring compression bolt 760.

Bottom plate 510 receives a tension set screw 790 (FIG. 41). Tension set screw 790 is threadably engaged in bore 535 of bottom plate 510 and engages the lower end of spring release pin 780, as will hereinafter be discussed.

2D. Cam Mechanism

Looking still at FIGS. 41 and 42, there is shown a cam mechanism 800 (FIG. 41) for selectively opening clamping assembly 455. Cam mechanism 800 is disposed in upper jaw 500 (upper jaw 500 is omitted from FIG. 41 for clarity) and comprises a cam 805 (FIG. 41) which is received in bearings 806 (FIG. 41). Cam 805 contains an eccentric 810 (FIG. 41) which exerts a downward force on cam bearing block 785 when cam 805 is rotated, as will hereinafter be discussed. Cam arm 815 (FIG. 41) is configured to receive one end of cable 820 (FIG. 37) at cable anchor 825 (FIG. 41). The other end of cable 820 is connected to actuating element or lever 665. Cam arm 815 is fixedly connected to cam 805.

As will hereinafter be discussed, when cable 820 is anchored to cam arm 815 and cable 820 is pulled (i.e., by pulling on actuating element or lever 665), it causes cam arm 815 to move, whereby to cause cam 805 to rotate. The rotation of cam 805, and the corresponding rotation of eccentric 810, causes eccentric 810 to push down on cam bearing block 785, which then pushes down on spring release pin 780. As will hereinafter be discussed, this action causes upper jaw 500 and lower jaw 505 to separate, whereby to allow semi-ball 625 and any appendages attached thereto (e.g., support rod 650) to move relative to semi-ball 625 (and hence relative to the surgical table to which clamping assembly 455 is attached).

Cam arm 815 is moved by the action of cable 820, which may be similar in construction to a brake cable, and generally comprises outer jacket 826 (FIG. 36) and an inner cable 827 (FIG. 36), although the exact configuration may be altered without changing the intention of this invention. It should be appreciated that cable 820 extends proximally from the distal end of support rod 650. More particularly, cable 820 is connected to actuating element or lever 665 located at the distal end of support rod 650 and extends proximally along the interior of support rod 650 until cable 820 reaches a portal 828 (FIG. 30) formed in support rod 650 just distal to the proximal end of support rod 650. A small portion 829 (FIG. 30) of cable 820 extends between portal 828 of support rod 650 and clamping assembly 455.

The provision of cable 820 as an actuating means, rather than providing a solid actuating means such as a rod, is advantageous, inasmuch as the cable allows the force applied to cam arm 815 to be routed in almost any direction desired by the physician.

Thus, the cable may route the force around bends and corners and allow the positioning of cable actuating element or lever 665 in a more comfortable and/or advantageous position for the physician. In one preferred embodiment of the invention, cable 820 is routed from cable anchor 825, through upper jaw 500, into support rod 650 via portal 828 (FIG. 37), and then back through support rod 650 to handle 660.

Actuating element or lever 665 itself may be configured in the manner of a brake lever, and, like cam arm 815, provides a force multiplier that, by decreasing the force necessary to open spring element 775 and thus release the clamping force of upper jaw 500 and lower jaw 505 from semi-ball 625, improves the action of the device for the physician.

It is important to realize that when tension is applied to cable 820 by the physician through actuating element or lever 665, cam arm 815 applies a rotational force to cam 805 which forces lower jaw 505 to separate (against the biasing force of spring element 775) from upper jaw 500, whereby to cause clamping assembly 455 to open. This action releases the clamping force of concave gripping surface 511 of upper jaw 500 and the concave gripping surface 512 of lower jaw 505 on semi-ball 625, which then allows clamping assembly 455 to move about any and/or all of the axes of semi-ball 625.

2E. Further Details Regarding Opening and Closing of the Clamping Assembly

When eccentric 810 is not exerting force on cam bearing block 785 (i.e., when clamping assembly 455 is in its resting or non-actuated state), clamping assembly 455 is clamped around semi-ball 625. The force exerted on semi-ball 625 by upper jaw 500 and lower jaw 505 of clamping element 455 is sufficient to prevent relative movement between semi-ball 625 and clamping assembly 455 (and hence, sufficient to maintain leg support assembly 415 in position vis-à-vis mount assembly 410).

More particularly, when clamping assembly 455 is in its resting or non-actuated state, spring element 775 is exerting a force on spring compression bolt 760 which pulls upper jaw 500 and lower jaw 505 toward one another. This force urges the concave gripping surface 511 of upper jaw 500 and the concave gripping surface 512 of lower jaw 505 against the spheroidal outer surface 626 of semi-ball 625. The force exerted on semi-ball 625 by concave gripping surface 511 of upper jaw 500 and concave gripping surface 512 of lower jaw 505 is sufficient to prevent relative movement between clamping assembly 455 and semi-ball 625. Thus, support rod 650 and all of the components attached thereto (e.g., boot 670) are similarly prevented from moving relative to semi-ball 625, resulting in the immobilization of leg support assembly 415 with respect to the surgical table.

When cam mechanism 800 is actuated (e.g., by pulling actuating element or lever 665), lower jaw 505 is forced (against the bias of spring element 775) to move away from upper jaw 500, thereby permitting semi-ball 625 (and the components attached thereto) to move relative to clamping assembly 455.

More particularly, cam mechanism 800 is actuated by rotating cam 805 (e.g., by pulling cable 820, which is connected to cam arm 815, which is connected to cam 805). When cam 805 is rotated, eccentric component 810 of cam 805 exerts a downward force on cam bearing block 785, which in turn exerts a downward force on spring release pin 780. This motion is represented by Arrow 1 shown in FIG. 42.

As previously discussed, spring release pin 780 runs through central bore 763 of spring compression bolt 760, and the downward force on spring release pin 780 causes it to contact and exert a downward force on tension set screw 790. Inasmuch as tension set screw 790 is fixed to bottom plate 510, the downward motion of spring release pin 780 applies a downward force to bottom plate 510. This motion is represented by Arrow 2 shown in FIG. 42.

The downward force applied to bottom plate 510 by spring release pin 780 is transmitted to lower jaw 505 by virtue of screws 555 which connect bottom plate 510 to lower jaw 505. This motion is represented by Arrow 3 shown in FIG. 42. As a result, lower jaw 505 is forced downward (against the bias of spring element 775) and hence away from upper jaw 500. This motion is represented by Arrow 4 shown in FIG. 42.

By increasing the distance between upper jaw 500 and lower jaw 505, concave gripping surface 511 of upper jaw 500 and concave gripping surface 512 of lower jaw 505 are each moved away from the spheroidal outer surface 626 of semi-ball 625. Accordingly, the force exerted by clamping assembly 455 on semi-ball 625 is reduced, allowing relative movement between the two components as discussed above.

Clamping assembly 455 may be restored to its initial state (i.e., that which prohibits relative movement between semi-ball 625 and clamping assembly 455) by discontinuing the application of force to the cam mechanism 800 (e.g., by discontinuing the application of force to cable 820 via actuating element or lever 665). By discontinuing the application of force to cam mechanism 800, the force exerted by cam 805 on spring release pin 780 will be overcome by the force exerted by spring element 775 (i.e., on head 765 of spring compression bolt 760 and annular shoulder 517 at the intersection of bore 515 and counterbore 516), which in turn exerts an upward force on lower jaw 505. This has the effect of reducing the distance between upper jaw 500 and lower jaw 505 and allowing clamping assembly 455 to again fit tightly around semi-ball 625, thereby preventing relative movement therebetween.

In addition, as lower jaw 505 and bottom plate 510 return upward, tension set screw 790 exerts an upward force on spring release pin 780, which accordingly pushes cam bearing block 785 upward and rotates cam 805 back to its initial position, with eccentric 810 not exerting downward force on cam bearing block 785.

2F. Use of the Second Embodiment of the Invention

Looking now at FIGS. 30-33, to achieve a controlled simulation of a ball-and-socket arrangement of mechanical elements, the present invention uses the truncated or semi-ball 625 gripped by upper jaw 500 and lower jaw 505, i.e., gripped between concave gripping surface 511 of upper jaw 500 and concave gripping surface 512 of lower jaw 505 that fit around the spheroidal outer surface 626 of semi-ball 625 in a concentric manner.

The range of rotational movement that the device can make around the semi-ball's longitudinal axis is controlled by the compressed and extended length of gas cylinder 680.

The device can move rotationally about two additional axes that are at right angles to each other, and to the previously-described longitudinal axis of semi-ball 625.

These additional rotational motions can be thought of as "pitch" and "yaw".

The "roll", "pitch" and "yaw" movements of clamping assembly 455 about semi-ball 625 correspond to the supination/pronation, lithotomy and abduction/adduction movement of the assembled device.

As discussed above, the ability of semi-ball 625 to rotate about clamping assembly 455 is controlled by upper jaw 500 and lower jaw 505 which act as a clamp around the semi-ball. It should be appreciated that the degree to which leg support assembly 415 can "pitch" or "yaw" relative to mount assembly 410 can be limited by the configuration of recess 900 formed between upper jaw 500 and lower jaw 505. By way of example but not limitation, it should be appreciated that the degree to which leg support assembly 415 can "pitch" or "yaw" relative to mount assembly 410 is a function of how far neck 627 of leg support assembly 415 can move within recess 900 before being limited by contact with either upper jaw 500 or lower jaw 505. More particularly, movement of leg support assembly 415 in the lithotomy direction (i.e., "pitch") is limited by the extent to which neck 627 can move up and down within recess 900 without contacting upper jaw 500 or lower jaw 505. Similarly, movement of leg support assembly 415 in the abduction/adduction directions (i.e., "yaw") is limited by the extent to which neck 627 can move side to side within recess 900 without contacting upper jaw 500 or lower jaw 505.

Normally upper jaw 500 and lower jaw 505 are held in the clamping position about semi-ball 625 by spring element 775 as previously discussed.

It will be understood that any spring configuration of sufficient force will prevent clamping assembly 455 from turning about any of the axes of semi-ball 625. Spring element 775 shown herein is intended to be illustrative and not limiting, and may be altered in many ways without changing the intention of this invention.

Thus it will be seen that the present invention provides a stirrup-type leg holder 405, wherein the stirrup-type leg holder comprises a mounting bracket 420 for attachment to a surgical table; a clamping assembly 455 for attachment to mounting bracket 420; the clamping assembly 455 comprising upper jaw 500 and lower jaw 505 for clamping engagement about a semi-ball 625 fixedly mounted to the proximal end of a support rod 450; and a stirrup boot 670 mounted to clamping assembly 455 via support rod 450. A release mechanism is provided to selectively release clamping assembly 455 (i.e., to release semi-ball 625 from clamping assembly 455) so as to allow stirrup boot 670 to be repositioned relative to clamping assembly 455 (and hence repositioned relative to the surgical table). The release mechanism comprises an actuating mechanism (e.g., a handle 660 and actuating element or lever 665) which controls a cam mechanism 800 which can force upper jaw 500 and lower jaw 505 apart, against the bias of spring element 775, whereby to allow upper jaw 500 and lower jaw 505 to release semi-ball 625, and hence allow the position of stirrup boot 670 to be adjusted relative to the surgical table. Gas cylinder 680 is also provided to assist in positioning the leg support assembly 415 relative to the surgical table.

In the foregoing description, mount assembly 410 is described as comprising a mounting bracket 420 and a clamping assembly 455 for releasably engaging a semi-ball 625, wherein semi-ball 625 comprises an outer surface 626 following a spheroidal geometry, and a neck 627 extending along the longitudinal axis of the semi-ball. However, it should be appreciated that if desired, semi-ball 625 may be replaced by a different mounting element comprising an outer surface 626 following a spheroidal geometry, e.g., a substantially complete sphere, etc. Furthermore, if desired, neck 627 may be omitted and semi-ball 625 (and/or such alternative mounting element, e.g., a substantially complete sphere) may be mounted directly to support rod 450.

It will be appreciated that numerous benefits are obtained by using the novel leg holder 405 of the present invention. First and foremost, the ball-and-socket type connection between mount assembly 410 and leg support assembly 415 allows for a greater range of motion along more axes of rotation, allowing the physician to place a patient's leg in the optimal position for a particular procedure. As a result, the physician is provided with a better operating environment, increasing the likelihood of better patient outcomes.

It should also be appreciated that the novel leg holder 405 may be reconfigured as a limb holder to provide support for different limbs, e.g., it may be reconfigured to provide support for the arms of a patient.

The present invention may also be used in connection with patient supports other than surgical tables, e.g., it may be used with gurneys, hospital beds, chairs, etc., and the present invention may be used for procedures other than surgical procedures, e.g., it may be used for examination procedures, physical therapy, etc.

3. Quick-Connect Universal Boot Mount

With the novel stirrup-type leg holder 5 discussed above, boot 70 is mounted to support rod 50 via slidable adjuster 75, and with the novel stirrup-type leg holder 405 discussed above, boot 670 is mounted to support rod 650 via slidable adjuster 675. It should be appreciated that the manner of mounting boot 70 to support rod 50 is the same as the manner of mounting boot 670 to support rod 450; therefore, for clarity of discussion, the present invention will now be discussed in the context of mounting boot 670 to support rod 650 via slidable adjuster 675, however, it should be appreciated that the present invention is also applicable to the mounting of boot 70 to support rod 50 and/or to any stirrup-type leg holder having a boot adjustably mounted thereto.

More particularly, and looking now at FIGS. 43-46, boot 670 is mounted to support rod 650 via slidable adjuster 675. Slidable adjuster 675 comprises a sliding element 1000 which is mounted in sliding disposition to support rod 650. Sliding element 1000 preferably comprises a locking handle 1005 for selectively securing sliding element 1000 in a selected position on support rod 650 (i.e., for securing sliding element 1000 to support rod 650 after sliding element 1000 has been moved to a desired position). A shaft 1010 extends away from sliding element 1000 substantially perpendicular to the longitudinal axis of support rod 650. A boot mount 1015 is mounted to the free end of shaft 1010. Boot 670 is mounted to boot mount 1015 by passing a plurality of screws 1020 through boot 670 and into a plurality of corresponding threaded holes 1022 formed in boot mount 1015. In one form of the present invention, three screws 1020 are used to mount boot 670 to boot mount 1015.

When it is desired to replace a given boot 670 with a different boot 670 (e.g., to use another boot which might better accommodate the anatomy of a particular patient, to replace a damaged boot, to provide a boot better suited for a particular surgical procedure, etc.), screws 1020 are removed (i.e., unscrewed), boot 670 is removed from boot mount 1015, and the replacement boot 670 is mounted to boot mount 1015 by passing screws 1020 through the replacement boot 670 and into the threaded holes 1022 formed in boot mount 1015, whereby to mount boot 670 to boot mount 1015.

However, it has been found that it can be time-consuming and hence inconvenient to remove screws 1020, and to re-insert screws 1020, every time that boot 670 is to be exchanged for another boot 670. Thus there is a need for a novel quick-connect universal boot mount which simplifies the process of removing a given boot 670 from boot mount 1015 (and hence from leg holder 405) and also simplifies the process of mounting a replacement boot 670 to boot mount 1015 (and hence to leg holder 405).

To this end, and looking now at FIGS. 47-53, there is shown a novel quick-connect universal boot mount 1025. Quick-connect universal boot mount 1025 comprises a base 1030 for mounting to the free end of shaft 1010, a releasable locking mechanism 1035 which is mounted to base 1030 (FIG. 50), and a mounting plate 1040 (FIG. 50) mounted to releasable locking mechanism 1035 for releasably mating with a counterpart boot mounting plate 1045 (FIG. 50) which is, in turn, secured to boot 670, as will hereinafter be discussed in greater detail.

Base 1030 is preferably selectively pivotable relative to shaft 1010 and may be mounted to the free end of shaft 1010 in various ways that will be apparent to those skilled in the art in view of the present disclosure.

Locking mechanism 1035 (FIGS. 50-53) preferably comprises a housing 1050 having a slot 1055 passing diametrically therethrough; and a first key 1060 and a second key 1065 which are slidably disposed within slot 1055 of housing 1050. First key 1060 comprises a heel 1070 (FIGS. 52 and 53), a toe 1075 and a keyway 1080 passing through first key 1060 intermediate heel 1070 and toe 1075. Second key 1065 comprises a heel 1085, a toe 1090 and a keyway 1095 passing through second key 1065 intermediate heel 1085 and toe 1090. First key 1060 and second key 1065 are slidably connected to one another, with their outward motion being limited via a pin 1098 which is fixed to housing 1050 and which extends through a slot 1100 in first key 1060 and through a slot 1105 in second key 1065. In other words, first key 1060 and second key 1065 are able to move within slot 1055 relative to one another over a limited distance (i.e., a distance limited by pin 1098 and slots 1100, 1105).

A first spring 1110 is disposed between toe 1075 of first key 1060 and heel 1085 of second key 1065. A second spring 1115 is disposed between toe 1090 of second key 1065 and heel 1070 of first key 1060. As a result of this construction, first key 1060 and second key 1065 are spring-biased away from one another (i.e., to the extent permitted by the disposition of pin 1095 in slots 1100, 1105) such that keyway 1080 of first key 1060 and keyway 1095 of second key 1065 have little or no overlap with one another when first key 1060 and second key 1065 are in their spring-biased state. However, when heel 1070 of first key 1060 and heel 1085 of second key 1065 are both pushed inwardly against the power of springs 1110, 1115, keyways 1080, 1095 have substantial overlap with one another.

Mounting plate 1040 (FIGS. 51-53) comprises a central opening 1120 which is vertically aligned with keyway 1080 of first key 1060 and with keyway 1095 of second key 1065 when an inwardly-directed force is applied to heel 1070 of first key 1060 and to heel 1085 of second key 1065 so as to create substantial overlap between keyways 1080, 1095. Mounting plate 1040 also comprises a plurality of upwardly-projecting pins 1125 for engaging a plurality of holes formed in boot mounting plate 1045, as will hereinafter be discussed in greater detail.

Boot mounting plate 1045 (FIG. 51), which is, in turn, secured to boot 670, comprises a projection 1130 extending away from boot mounting plate 1045. Projection 1130 is sized to be received in central opening 1120 of mounting plate 1040 (and keyways 1080, 1095 of locking mechanism 1035 when keyways 1080, 1095 have substantial overlap with one another). Projection 1130 preferably comprises a reduced-diameter section 1135 located near its proximal end. Boot mounting plate 1045 also comprises a plurality of holes 1140 which are sized to receive the plurality of upwardly-projecting pins 1125 formed on mounting plate 1040, whereby to provide proper alignment between boot 670 and quick connect universal boot mount 1025 (and also to prevent rotation of boot mounting plate 1045 relative to mounting plate 1040, and hence, to prevent rotation of boot 670 relative to quick connect universal boot mount 1025).

When it is desired to mount a boot 670 to universal boot mount 1025, the user pushes heel 1070 of first key 1060 and heel 1085 of second key 1065 inwardly against the power of springs 1110, 1115, so as to create substantial overlap between keyways 1080, 1095 (which substantial overlap is aligned with central opening 1120 of mounting plate 1040). Boot mounting plate 1045 (carrying boot 670 mounted thereto) is aligned with mounting plate 1040 and the components moved into contact such that projection 1130 enters central opening 1120 in mounting plate 1040 and the substantial overlap between keyways 1080, 1095, and so that the plurality of upwardly projecting pins 1125 formed on mounting plate 1040 are aligned with, and enter, the plurality of holes 1140 formed on boot mounting plate 1045. Heels 1070, 1085 are then released so that first key 1060 and second key 1065 are biased away from each other under the power of springs 1110, 1115. This causes toe 1075 of first key 1060 to move laterally into reduced-diameter section 1135 of projection 1130, and toe 1090 of second key 1065 to move laterally into reduced-diameter section 1135 of projection 1130, whereby to lock projection 1130 of boot mounting plate 1045 to universal boot mount 1025 (and hence to lock boot 670 to universal boot mount 1025).

When boot 670 is to be replaced by another boot 670 (see FIG. 50, which shows three exemplary stirrup boots), the first boot 670 is removed from quick connect universal boot mount 1025 by pushing heel 1070 of first key 1060 and heel 1085 of second key 1065 inwardly against the power of springs 1110, 1115, and then pulling on the currently-mounted boot 670 so as to remove projection 1130 from central opening 1120 of mounting plate 1040 (and so as to remove holes 1140 of boot mounting plate 1045 from upwardly-projecting pins 1125 of mounting plate 1040). A replacement boot 670 can then be mounted to quick-connect universal boot mount 1025 by pushing heel 1070 of first key 1060 and heel 1085 of second key 1065 inwardly against the power of springs 1110, 1115, so as to create substantial overlap between keyways 1080, 1095 (which substantial overlap is aligned with central opening 1120 of mounting plate 1040). The boot mounting plate 1045 of the replacement boot 670 is then aligned with mounting plate 1040 and the components moved into contact such that projection 1130 enters central opening 1120 in mounting plate 1040 and the substantial overlap between keyways 1080, 1095, and so that the plurality of upwardly projecting pins 1125 formed on mounting plate 1040 are aligned with, and enter, the plurality of holes 1140 formed on boot mounting plate 1045. Heels 1070, 1085 are then released so that first key 1060 and second key 1065 are biased away from each other under the power of springs 1110, 1115. This causes toe 1075 of first key 1060 to move laterally into reduced-diameter section 1135 of projection 1130, and toe 1090 of second key 1065 to move laterally into reduced-diameter section 1135 of projection 1130, whereby to lock projection 1130 of boot mounting plate 1045 to universal boot mount 1025 (and hence to lock boot 670 to universal boot mount 1025).

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A surgical boot mount for mounting a surgical boot to a support rod of a limb holder, the surgical boot mount comprising:
    a boot mounting plate;
    a projection having a first section and a second section, wherein the first section is attached to the boot mounting plate, wherein the first section comprises a first diameter and the second section comprises a second diameter, and further wherein the second diameter is larger than the first diameter; and
    a releasable locking mechanism configured to be mounted to the support rod of the limb holder, wherein the releasable locking mechanism comprises:
        a first key comprising a first keyway and a second key comprising a second keyway, wherein the second key is slidably connected to the first key, wherein the first key and the second key are biased away from one another, wherein the first keyway and the second keyway overlap to form an opening at least as large as the second diameter of the projection when an inwardly-directed force is applied to the first key and the second key so as to overcome the bias, and further wherein the opening is reduced to a size smaller than the second diameter of the projection when the inwardly-directed force is released from the first key and the second key; and
        a pin fixed to the releasable locking mechanism and extending through a first slot in the first key and a second slot in the second key so as to limit motion between the first key and the second key.

2. The surgical boot mount according to claim 1 further comprising a base for mounting the releasable locking mechanism to the support rod of the limb holder.

3. The surgical boot mount according to claim 1 wherein the releasable locking mechanism comprises a housing having a slot passing diametrically therethrough, and further wherein the first key and the second key are disposed in the slot.

4. The surgical boot mount according to claim 3 wherein the first key and the second key are both movable relative to the housing.

5. The surgical boot mount according to claim 1 wherein the releasable locking mechanism comprises at least one spring for biasing the first key away from the second key.

6. The surgical boot mount according to claim 1 further comprising a base mounting plate mounted to the releasable locking mechanism, wherein the boot mounting plate releasably mates with the base mounting plate, and further wherein the base mounting plate comprises a central opening aligned with the first keyway and the second keyway.

7. The surgical boot mount according to claim 6 wherein the base mounting plate comprises at least one upwardly-projecting pin, and further wherein the boot mounting plate comprises at least one hole for mating with the at least one upwardly-projecting pin.

8. A method of mounting a surgical boot to a support rod of a limb holder, the method comprising:
    providing a surgical boot mount, the surgical boot mount comprising:
        a boot mounting plate;
        a projection having a first section and a second section, wherein the first section is attached to the boot mounting plate, wherein the first section comprises a first diameter and the second section comprises a second diameter, and further wherein the second diameter is larger than the first diameter; and
        a releasable locking mechanism configured to be mounted to the support rod of the limb holder, wherein the releasable locking mechanism comprises:
            a first key comprising a first keyway and a second key comprising a second keyway, wherein the second key is slidably connected to the first key, and further wherein the first key and the second key are biased away from one another; and
            a pin fixed to the releasable locking mechanism and extending through a first slot in the first key and a second slot in the second key so as to limit motion between the first key and the second key;
    applying an inwardly-directed force to the first key and the second key so as overcome the bias and cause the first keyway and the second keyway to overlap to form an opening at least as large as the second diameter of the projection;
    inserting the projection into the opening;
    releasing the inwardly-directed force from the first key and the second key so that the opening is reduced to a smaller size than the second diameter of the projection, whereby to mount the surgical boot to the support rod of the limb holder.

9. The method according to claim 8 wherein the surgical boot mount further comprises a base for mounting the releasable locking mechanism to the support rod of the limb holder.

10. The method according to claim 8 wherein the releasable locking mechanism comprises a housing having a slot passing diametrically therethrough, and further wherein the first key and the second key are disposed in the slot.

11. The method according to claim 8 wherein the releasable locking mechanism comprises at least one spring for biasing the first key away from the second key.

12. The method according to claim 8 wherein the surgical boot mount further comprises a base mounting plate mounted to the releasable locking mechanism, wherein the boot mounting plate releasably mates with the base mounting plate, and further wherein the base mounting plate comprises a central opening aligned with the first keyway and the second keyway.

13. The method according to claim 12 wherein the base mounting plate comprises at least one upwardly-projecting pin, and further wherein the boot mounting plate comprises at least one hole for mating with the at least one upwardly-projecting pin.

14. The method according to claim 12 further comprising mounting the surgical boot to the boot mounting plate.

15. The method according to claim 14 wherein the surgical boot is mounted to the boot mounting plate before the boot mounting plate is mounted to the base mounting plate.

16. The method according to claim 14 wherein the surgical boot is mounted to the boot mounting plate after the boot mounting plate is connected to the base mounting plate.

* * * * *